US012655187B2

(12) United States Patent
Wang

(10) Patent No.: US 12,655,187 B2
(45) Date of Patent: Jun. 16, 2026

(54) PEPTIDE IMMUNOGENS TARGETING CALCITONIN GENE-RELATED PEPTIDE (CGRP) AND FORMULATIONS THEREOF FOR PREVENTION AND TREATMENT OF MIGRAINE

(71) Applicant: UNITED NEUROSCIENCE LIMITED, Dublin (IE)

(72) Inventor: Chang Yi Wang, Cold Spring Harbor, NY (US)

(73) Assignee: United Neuroscience Limited, Dublin (IE)

( * ) Notice: Subject to any disclaimer, the term of this patent is extended or adjusted under 35 U.S.C. 154(b) by 1307 days.

(21) Appl. No.: 17/420,002

(22) PCT Filed: Dec. 31, 2019

(86) PCT No.: PCT/US2019/069117
§ 371 (c)(1),
(2) Date: Jun. 30, 2021

(87) PCT Pub. No.: WO2020/142522
PCT Pub. Date: Jul. 9, 2020

(65) Prior Publication Data
US 2022/0073582 A1 Mar. 10, 2022

Related U.S. Application Data

(60) Provisional application No. 62/787,102, filed on Dec. 31, 2018.

(51) Int. Cl.
*A61K 39/00* (2006.01)
*A61K 39/39* (2006.01)
(Continued)

(52) U.S. Cl.
CPC ........ *C07K 14/585* (2013.01); *A61K 39/0005* (2013.01); *A61K 39/39* (2013.01);
(Continued)

(58) Field of Classification Search
None
See application file for complete search history.

(56) References Cited

U.S. PATENT DOCUMENTS 6,559,282 B1 5/2003 Wang
2004/0009897 A1 1/2004 Sokoll
(Continued)

FOREIGN PATENT DOCUMENTS

DE        19732944 A1 * 2/1999 ....... C07K 14/57527
WO    WO-9728272 A1 * 8/1997 ............. C07K 14/31
(Continued)

OTHER PUBLICATIONS

WIPO translation of DE19732944 (Year: 1999).*
(Continued)

*Primary Examiner* — M Franco G Salvoza
(74) *Attorney, Agent, or Firm* — Foley Hoag LLP; Maya Elbert

(57) ABSTRACT

The present disclosure is directed to peptide immunogen constructs targeting portions of Calcitonin Gene-Related Peptide (CGRP), compositions containing the constructs, antibodies elicited by the constructs, and methods for making and using the constructs and compositions thereof. The disclosed peptide immunogen constructs have more than about 30 amino acids and contain (a) a B cell epitope having about more than about 7 contiguous amino acid residues from the CGRP receptor binding or activation regions of the full-length CGRP protein; (b) a heterologous Th epitope; and (c) an optional heterologous spacer. The disclosed CGRP peptide immunogen constructs stimulate the genera-
(Continued)

Immunogenicity Studies of CGRP Peptide Immunogen Constructs in Guinea Pigs

Immunogenicity Studies of CGRP Peptide Immunogen Constructs in Guinea Pigs tion of highly specific antibodies directed CGRP for the prevention and/or treatment of migraine.

7 Claims, 8 Drawing Sheets

Specification includes a Sequence Listing.

(51) Int. Cl.
| | |
|---|---|
| *A61P 25/06* | (2006.01) |
| *C07K 14/585* | (2006.01) |
| *C07K 16/18* | (2006.01) |

(52) U.S. Cl.
CPC .............. *A61P 25/06* (2018.01); *C07K 16/18* (2013.01); *A61K 2039/55561* (2013.01); *C07K 2319/33* (2013.01)

(56) References Cited

U.S. PATENT DOCUMENTS

| | | |
|---|---|---|
| 2004/0247612 A1 | 12/2004 | Wang |
| 2005/0106137 A1 | 5/2005 | Grimes |
| 2011/0171243 A1 | 7/2011 | Mandler et al. |
| 2014/0271690 A1 | 9/2014 | Wang |

FOREIGN PATENT DOCUMENTS

| | | | | |
|---|---|---|---|---|
| WO | WO-0069900 A2 | * | 11/2000 | ............. A61K 38/38 |
| WO | WO-02096350 A2 | * | 12/2002 | ............. A61P 25/28 |
| WO | WO-2007/054809 A2 | | 5/2007 | |
| WO | WO-2007/076336 A1 | | 7/2007 | |
| WO | WO-2014/143087 A1 | | 9/2014 | |
| WO | WO-2015127416 A1 | * | 8/2015 | ........... A61K 31/166 |
| WO | WO-2016/062720 A1 | | 4/2016 | |
| WO | WO-2018/232369 A1 | | 12/2018 | |
| WO | WO-2020/142522 A2 | | 7/2020 | |

OTHER PUBLICATIONS

Sprenger et al., "Current Prophylactic Medications for Migraine and Their Potential Mechanisms of Action," Neurotherapeutics, 15: 313-323 (Year: 2018).*

Edvinsson et al., "CGRP as the target of new migraine therapies—successful translation from bench to clinic", Nature Reviews Neurology, Nature Publishing Group UK, London, vol. 14, No. 6, Apr. 24, 2018 (Apr. 24, 2018), pp. 338-350.

Frobert et al., "A sensitive sandwich enzyme immunoassay for calcitonin gene-related peptide (CGRP): Characterization and application", Peptides 20 (1999):275-284.

Supplementary European Search Report for EP Application No. 19906797.6 dated Oct. 28, 2022.

Written Opinion and Declaration of Non-Establishment of International Search Report for International Application No. PCT/US2019/069117 dated Mar. 18, 2020.

Dirks, "Brain Tumor Stem Cells: Bringing Order to the Chaos of Brain Cancer," Journal of Clinical Oncology 26.17 (2008): 2916-2924.

Lopez-Lazaro, "The migration ability of stem cells can explain the existence of cancer of unknown primary site. Rethinking metastasis," Oncoscience 2.5 (2015): 467-475.

Mabey, "Epidemiology of sexually transmitted infections: worldwide," Medicine 42.6 (2014): 287-290.

Tran et al., "Survival comparison between glioblastoma multiforme and other incurable cancers," Journal of Clinical Neuroscience 17.4 (2010): 417-421.

Wu et al., "Expression and purification of chimeric peptide comprising EGFR B-cell epitope and measles virus fusion protein T-cell epitope in *Escherichia coli*," Protein Expression and Purification 88.1 (2012): 7-12.

* cited by examiner

Figure 1.
Clustal O(1.2.4) alignment of CGRP sequences from multiple Species

| Species | Sequence | SEQ ID NO |
|---|---|---|
| Human | ACDTATCVTHRLAGLLSRSGGVVKNNFVPTNVGSKAF | 1 |
| Marmoset | ACDTATCVTHRLAGLLSRSGGMVKNNFVPTNVGSEAF | 2 |
| Rat | SCNTATCVTHRLAGLLSRSGGVVKDNFVPTNVGSEAF | 3 |
| Mouse | SCNTATCVTHRLAGLLSRSGGVVKDNFVPTNVGSEAF | 3 |
| Horse | SCNTATCVTHRLAGLLSRSGGVVKSNFVPTNVGSEAF | 182 |
| Chicken | ACNTATCVTHRLADFLSRSGGVGKNNFVPTNVGSKAF | 183 |
| Pig | SCNTATCVTHRLAGLLSRSGGMVKSNFVPTNVGSEAF | 184 |
| Sheep | SCNTATCVTHRLAGLLSRSGGVVKSNFVPTDVGSEAF | 185 |
| Cow | SCNTATCVTHRLAGLLSRSGGVVKSNFVPTNVGSQAF | 186 |
| Dog | SCNTATCVTHRLAGLLSRSGGVVKNNFVPTNVGSEAF | 187 |
| Opossum | GCNTATCVTHRLADFLSRSGGVAKSDFVPTNVGAKAF | 188 |
| Geckko | ACNTATCVTHRLADFLSRSGGVGKSNFVPTNVGAKAF | 189 |
| Frog | SCIDTSTCATQRLADFLSRSGGIGSPDFVPTDVSANSF | 190 |
| Pufferfish | ACNTATCVTHRLADFLSRSGGMGNSNFVPTNVGAKAF | 191 |
| Flounder | GCNTSTCVTHRLADFLLSRSGGLGYNNFVPTNVGAQAF | 192 |
| Goldfish | ACNTATCVTHRLADFLSRSGGIGSSKFVPTNVGSQAF | 193 |
| Salmon | ACNTATCVTHRLADFLSRSGGMGNSNFVPTNVGSKAF | 194 |
| Medalea | ACNTATCVTHRLADFLSRSGGLGHSNFVPTNVGAQAF | 195 |
| Zebrafish | ACNTATCVTHRLADFLSRSGGIGSSDFVPTNVGSQAF | 196 |

Pathways From Discovery to Commercialization of High Precision Designer Vaccine Technology

Immunogenicity Studies of CGRP Peptide Immunogen Constructs in Guinea Pigs

Immunogenicity Studies of CGRP Peptide Immunogen Constructs in Guinea Pigs

Figure 4.

Neutralization Activities (expressed as IC50 of % cAMP)of Purified Antibodies from Guinea Pig Immune Sera of Representative CGRP Peptide Immunogen Constructs

| SEQ NO: | IC50 (µg/ml) |
|---|---|
| 116 (1-10) | >20 |
| 117 (1-10) | >20 |
| 118 (1-10) | >20 |
| 124 (1-15) | 4.44 |
| 125 (1-18) | 2.20 |
| 126 (1-20) | 4.63 |
| 127 (1-25) | 1.83 |

| SEQ NO: | IC50 (µg/mL) |
|---|---|
| 128 (8-18) | >20 |
| 129 (8-18) | 8.73 |
| 131 (11-25) | 1.19 |
| 133 (11-30) | 5.42 |
| 135 (11-33) | 14.14 |
| 137 (11-35) | 2.60 |

SEQ NO: 116
SEQ NO: 117
SEQ NO: 118
SEQ NO: 124
SEQ NO: 125
SEQ NO: 126
SEQ NO: 127

SEQ NO: 128
SEQ NO: 129
SEQ NO: 131
SEQ NO: 133
SEQ NO: 135
SEQ NO: 137

N-Terminal cAMP level (%)

IgG con. (µg/ml)

Central Region cAMP level (%)

IgG con. (µg/ml)

Neutralization Activities (expressed as IC50 of % cAMP) of Purified Antibodies from Guinea Pig Immune Sera of Representative CGRP Peptide Immunogen Constructs

| SEQ NO: | IC50 (µg/mL) |
|---|---|
| 119 (31-37) | 11.24 |
| 120 (28-37) | 5.76 |
| 121 (25-37) | 2.51 |
| 122 (18-37) | 2.60 |
| 123 (εKKKK11-37) | 2.05 |
| 130 (εK11-37) | 0.60 |
| 139 (εKKKK15-37) | 10.1 |
| 150 (rat εKKKK11-37) | 1.15 |

Immunogenicity Study of Representative CGRP Peptide Immunogen Constructs in Mice Representative CGRP Peptide Immunogen Constructs and Formulations thereof in a Proof of Concept Study in Mice for treatment of Migraine by measuring Capsaicin-induced dermal blood flow

SEQUENCE LISTING

<160> NUMBER OF SEQ ID NOS: 196

<210> SEQ ID NO 1
<211> LENGTH: 37
<212> TYPE: PRT
<213> ORGANISM: Homo sapiens
<220> FEATURE:
<221> NAME/KEY: PEPTIDE
<222> LOCATION: (1)..(37)
<223> OTHER INFORMATION: Human alpha-CGRP 1-37

<400> SEQUENCE: 1

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35

<210> SEQ ID NO 2
<211> LENGTH: 37
<212> TYPE: PRT
<213> ORGANISM: Callithrix jacchus
<220> FEATURE:
<221> NAME/KEY: PEPTIDE
<222> LOCATION: (1)..(37)
<223> OTHER INFORMATION: Marmoset alpha-CGRP 1-37

<400> SEQUENCE: 2

Ala Cys Asp Thr Ala Thr Cys Val Thr His Arg Leu Ala Gly Leu Leu
1               5                   10                  15

```
Ser Arg Ser Gly Gly Met Val Lys Asn Asn Phe Val Pro Thr Asn Val
            20                  25                  30

Gly Ser Glu Ala Phe
        35

<210> SEQ ID NO 3
<211> LENGTH: 37
<212> TYPE: PRT
<213> ORGANISM: Rattus norvegicus
<220> FEATURE:
<221> NAME/KEY: PEPTIDE
<222> LOCATION: (1)..(37)
<223> OTHER INFORMATION: Rat/Mouse alpha-CGRP 1-37

<400> SEQUENCE: 3

Ser Cys Asn Thr Ala Thr Cys Val Thr His Arg Leu Ala Gly Leu Leu
1               5                   10                  15

Ser Arg Ser Gly Gly Val Val Lys Asp Asn Phe Val Pro Thr Asn Val
            20                  25                  30

Gly Ser Glu Ala Phe
        35

<210> SEQ ID NO 4
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 1-10

<400> SEQUENCE: 4

Ala Cys Asp Thr Ala Thr Cys Val Thr His
1               5                   10

<210> SEQ ID NO 5
<211> LENGTH: 7
<212> TYPE: PRT
<213> ORGANISM: Homo sapiens
<220> FEATURE:
<221> NAME/KEY: PEPTIDE
<222> LOCATION: (1)..(7)
<223> OTHER INFORMATION: alpha-CGRP 31-37

<400> SEQUENCE: 5

Asn Val Gly Ser Lys Ala Phe
1               5

<210> SEQ ID NO 6
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 28-37

<400> SEQUENCE: 6

Val Pro Thr Asn Val Gly Ser Lys Ala Phe
1               5                   10

<210> SEQ ID NO 7
<211> LENGTH: 13
<212> TYPE: PRT
<213> ORGANISM: Homo sapiens
<220> FEATURE:
```

```
<221> NAME/KEY: PEPTIDE
<222> LOCATION: (1)..(13)
<223> OTHER INFORMATION: alpha-CGRP 25-37

<400> SEQUENCE: 7

Asn Asn Phe Val Pro Thr Asn Val Gly Ser Lys Ala Phe
1               5                   10

<210> SEQ ID NO 8
<211> LENGTH: 20
<212> TYPE: PRT
<213> ORGANISM: Homo sapiens
<220> FEATURE:
<221> NAME/KEY: PEPTIDE
<222> LOCATION: (1)..(20)
<223> OTHER INFORMATION: alpha-CGRP 18-37

<400> SEQUENCE: 8

Arg Ser Gly Gly Val Val Lys Asn Asn Phe Val Pro Thr Asn Val Gly
1               5                   10                  15

Ser Lys Ala Phe
            20

<210> SEQ ID NO 9
<211> LENGTH: 27
<212> TYPE: PRT
<213> ORGANISM: Homo sapiens
<220> FEATURE:
<221> NAME/KEY: PEPTIDE
<222> LOCATION: (1)..(27)
<223> OTHER INFORMATION: alpha-CGRP 11-37

<400> SEQUENCE: 9

Arg Leu Ala Gly Leu Leu Ser Arg Ser Gly Gly Val Val Lys Asn Asn
1               5                   10                  15

Phe Val Pro Thr Asn Val Gly Ser Lys Ala Phe
            20                  25

<210> SEQ ID NO 10
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: alpha-CGRP 1-15

<400> SEQUENCE: 10

Ala Cys Asp Thr Ala Thr Cys Val Thr His Arg Leu Ala Gly Leu
1               5                   10                  15

<210> SEQ ID NO 11
<211> LENGTH: 18
<212> TYPE: PRT
<213> ORGANISM: Homo sapiens
<220> FEATURE:
<221> NAME/KEY: PEPTIDE
<222> LOCATION: (1)..(18)
<223> OTHER INFORMATION: alpha-CGRP 1-18

<400> SEQUENCE: 11

Ala Cys Asp Thr Ala Thr Cys Val Thr His Arg Leu Ala Gly Leu Leu
1               5                   10                  15

Ser Arg

<210> SEQ ID NO 12
```

-continued

```
<211> LENGTH: 20
<212> TYPE: PRT
<213> ORGANISM: Homo sapiens
<220> FEATURE:
<221> NAME/KEY: PEPTIDE
<222> LOCATION: (1)..(20)
<223> OTHER INFORMATION: alpha-CGRP 1-20

<400> SEQUENCE: 12

Ala Cys Asp Thr Ala Thr Cys Val Thr His Arg Leu Ala Gly Leu Leu
1               5                   10                  15

Ser Arg Ser Gly
            20

<210> SEQ ID NO 13
<211> LENGTH: 25
<212> TYPE: PRT
<213> ORGANISM: Homo sapiens
<220> FEATURE:
<221> NAME/KEY: PEPTIDE
<222> LOCATION: (1)..(25)
<223> OTHER INFORMATION: alpha-CGRP 1-25

<400> SEQUENCE: 13

Ala Cys Asp Thr Ala Thr Cys Val Thr His Arg Leu Ala Gly Leu Leu
1               5                   10                  15

Ser Arg Ser Gly Gly Val Val Lys Asn
            20                  25

<210> SEQ ID NO 14
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: alpha-CGRP 8-18

<400> SEQUENCE: 14

Val Thr His Arg Leu Ala Gly Leu Leu Ser Arg
1               5                   10

<210> SEQ ID NO 15
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: alpha-CGRP 11-25

<400> SEQUENCE: 15

Arg Leu Ala Gly Leu Leu Ser Arg Ser Gly Gly Val Val Lys Asn
1               5                   10                  15

<210> SEQ ID NO 16
<211> LENGTH: 20
<212> TYPE: PRT
<213> ORGANISM: Homo sapiens
<220> FEATURE:
<221> NAME/KEY: PEPTIDE
<222> LOCATION: (1)..(20)
<223> OTHER INFORMATION: alpha-CGRP 11-30

<400> SEQUENCE: 16

Arg Leu Ala Gly Leu Leu Ser Arg Ser Gly Gly Val Val Lys Asn Asn
1               5                   10                  15
```

```
Phe Val Pro Thr
            20

<210> SEQ ID NO 17
<211> LENGTH: 23
<212> TYPE: PRT
<213> ORGANISM: Homo sapiens
<220> FEATURE:
<221> NAME/KEY: PEPTIDE
<222> LOCATION: (1)..(23)
<223> OTHER INFORMATION: alpha-CGRP 11-33

<400> SEQUENCE: 17

Arg Leu Ala Gly Leu Leu Ser Arg Ser Gly Gly Val Val Lys Asn Asn
1               5                   10                  15

Phe Val Pro Thr Asn Val Gly
            20

<210> SEQ ID NO 18
<211> LENGTH: 25
<212> TYPE: PRT
<213> ORGANISM: Homo sapiens
<220> FEATURE:
<221> NAME/KEY: PEPTIDE
<222> LOCATION: (1)..(25)
<223> OTHER INFORMATION: alpha-CGRP 11-35

<400> SEQUENCE: 18

Arg Leu Ala Gly Leu Leu Ser Arg Ser Gly Gly Val Val Lys Asn Asn
1               5                   10                  15

Phe Val Pro Thr Asn Val Gly Ser Lys
            20                  25

<210> SEQ ID NO 19
<211> LENGTH: 23
<212> TYPE: PRT
<213> ORGANISM: Homo sapiens
<220> FEATURE:
<221> NAME/KEY: PEPTIDE
<222> LOCATION: (1)..(23)
<223> OTHER INFORMATION: alpha-CGRP 15-37

<400> SEQUENCE: 19

Leu Leu Ser Arg Ser Gly Gly Val Val Lys Asn Asn Phe Val Pro Thr
1               5                   10                  15

Asn Val Gly Ser Lys Ala Phe
            20

<210> SEQ ID NO 20
<211> LENGTH: 18
<212> TYPE: PRT
<213> ORGANISM: Homo sapiens
<220> FEATURE:
<221> NAME/KEY: PEPTIDE
<222> LOCATION: (1)..(18)
<223> OTHER INFORMATION: alpha-CGRP 20-37

<400> SEQUENCE: 20

Gly Gly Val Val Lys Asn Asn Phe Val Pro Thr Asn Val Gly Ser Lys
1               5                   10                  15

Ala Phe

<210> SEQ ID NO 21
<211> LENGTH: 16
<212> TYPE: PRT
<213> ORGANISM: Homo sapiens
```

```
<220> FEATURE:
<221> NAME/KEY: PEPTIDE
<222> LOCATION: (1)..(16)
<223> OTHER INFORMATION: alpha-CGRP 22-37

<400> SEQUENCE: 21

Val Val Lys Asn Asn Phe Val Pro Thr Asn Val Gly Ser Lys Ala Phe
1               5                   10                  15

<210> SEQ ID NO 22
<211> LENGTH: 8
<212> TYPE: PRT
<213> ORGANISM: Homo sapiens
<220> FEATURE:
<221> NAME/KEY: PEPTIDE
<222> LOCATION: (1)..(8)
<223> OTHER INFORMATION: alpha-CGRP 11-18

<400> SEQUENCE: 22

Arg Leu Ala Gly Leu Leu Ser Arg
1               5

<210> SEQ ID NO 23
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: alpha-CGRP 5-18

<400> SEQUENCE: 23

Ala Thr Cys Val Thr His Arg Leu Ala Gly Leu Leu Ser Arg
1               5                   10

<210> SEQ ID NO 24
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: alpha-CGRP 4-16

<400> SEQUENCE: 24

Thr Ala Thr Cys Val Thr His Arg Leu Ala Gly Leu Leu
1               5                   10

<210> SEQ ID NO 25
<211> LENGTH: 27
<212> TYPE: PRT
<213> ORGANISM: Rattus norvegicus
<220> FEATURE:
<221> NAME/KEY: PEPTIDE
<222> LOCATION: (1)..(27)
<223> OTHER INFORMATION: Rat alpha-CGRP 11-37

<400> SEQUENCE: 25

Arg Leu Ala Gly Leu Leu Ser Arg Ser Gly Gly Val Val Lys Asp Asn
1               5                   10                  15

Phe Val Pro Thr Asn Val Gly Ser Glu Ala Phe
            20                  25

<210> SEQ ID NO 26
<211> LENGTH: 10
<212> TYPE: PRT
<213> ORGANISM: Homo sapiens
<220> FEATURE:
```

<221> NAME/KEY: PEPTIDE
<222> LOCATION: (1)..(10)
<223> OTHER INFORMATION: alpha-CGRP -9 - 1

<400> SEQUENCE: 26

Gly Ser Arg Ile Ile Ala Gln Lys Arg Ala
1               5                   10

<210> SEQ ID NO 27
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP -8 - 2

<400> SEQUENCE: 27

Ser Arg Ile Ile Ala Gln Lys Arg Ala Cys
1               5                   10

<210> SEQ ID NO 28
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP -7 - 3

<400> SEQUENCE: 28

Arg Ile Ile Ala Gln Lys Arg Ala Cys Asp
1               5                   10

<210> SEQ ID NO 29
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP -6 - 4

<400> SEQUENCE: 29

Ile Ile Ala Gln Lys Arg Ala Cys Asp Thr
1               5                   10

<210> SEQ ID NO 30
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP -5 - 5

<400> SEQUENCE: 30

Ile Ala Gln Lys Arg Ala Cys Asp Thr Ala
1               5                   10

<210> SEQ ID NO 31
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP -4 - 6

```
<400> SEQUENCE: 31

Ala Gln Lys Arg Ala Cys Asp Thr Ala Thr
1               5                   10

<210> SEQ ID NO 32
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP -3 - 7

<400> SEQUENCE: 32

Gln Lys Arg Ala Cys Asp Thr Ala Thr Cys
1               5                   10

<210> SEQ ID NO 33
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP -2 - 8

<400> SEQUENCE: 33

Lys Arg Ala Cys Asp Thr Ala Thr Cys Val
1               5                   10

<210> SEQ ID NO 34
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP -1 - 9

<400> SEQUENCE: 34

Arg Ala Cys Asp Thr Ala Thr Cys Val Thr
1               5                   10

<210> SEQ ID NO 35
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 1 - 10

<400> SEQUENCE: 35

Ala Cys Asp Thr Ala Thr Cys Val Thr His
1               5                   10

<210> SEQ ID NO 36
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 2 - 11

<400> SEQUENCE: 36

Cys Asp Thr Ala Thr Cys Val Thr His Arg
1               5                   10
```

```
<210> SEQ ID NO 37
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 3 - 12

<400> SEQUENCE: 37

Asp Thr Ala Thr Cys Val Thr His Arg Leu
1               5                   10

<210> SEQ ID NO 38
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 4 - 13

<400> SEQUENCE: 38

Thr Ala Thr Cys Val Thr His Arg Leu Ala
1               5                   10

<210> SEQ ID NO 39
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 5 - 14

<400> SEQUENCE: 39

Ala Thr Cys Val Thr His Arg Leu Ala Gly
1               5                   10

<210> SEQ ID NO 40
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 6 - 15

<400> SEQUENCE: 40

Thr Cys Val Thr His Arg Leu Ala Gly Leu
1               5                   10

<210> SEQ ID NO 41
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 7 - 16

<400> SEQUENCE: 41

Cys Val Thr His Arg Leu Ala Gly Leu Leu
1               5                   10

<210> SEQ ID NO 42
<211> LENGTH: 10
```

```
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 8 - 17

<400> SEQUENCE: 42

Val Thr His Arg Leu Ala Gly Leu Leu Ser
1               5                   10

<210> SEQ ID NO 43
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 9 - 18

<400> SEQUENCE: 43

Thr His Arg Leu Ala Gly Leu Leu Ser Arg
1               5                   10

<210> SEQ ID NO 44
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 10 - 19

<400> SEQUENCE: 44

His Arg Leu Ala Gly Leu Leu Ser Arg Ser
1               5                   10

<210> SEQ ID NO 45
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 11 - 20

<400> SEQUENCE: 45

Arg Leu Ala Gly Leu Leu Ser Arg Ser Gly
1               5                   10

<210> SEQ ID NO 46
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 12 - 21

<400> SEQUENCE: 46

Leu Ala Gly Leu Leu Ser Arg Ser Gly Gly
1               5                   10

<210> SEQ ID NO 47
<211> LENGTH: 10
<212> TYPE: PRT
<213> ORGANISM: Homo sapiens
<220> FEATURE:
<221> NAME/KEY: PEPTIDE
```

```
<222> LOCATION: (1)..(10)
<223> OTHER INFORMATION: alpha-CGRP 13 - 22

<400> SEQUENCE: 47

Ala Gly Leu Leu Ser Arg Ser Gly Gly Val
1               5                   10

<210> SEQ ID NO 48
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 14 - 23

<400> SEQUENCE: 48

Gly Leu Leu Ser Arg Ser Gly Gly Val Val
1               5                   10

<210> SEQ ID NO 49
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 15 - 24

<400> SEQUENCE: 49

Leu Leu Ser Arg Ser Gly Gly Val Val Lys
1               5                   10

<210> SEQ ID NO 50
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 16 - 25

<400> SEQUENCE: 50

Leu Ser Arg Ser Gly Gly Val Val Lys Asn
1               5                   10

<210> SEQ ID NO 51
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 17 - 26

<400> SEQUENCE: 51

Ser Arg Ser Gly Gly Val Val Lys Asn Asn
1               5                   10

<210> SEQ ID NO 52
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 18 - 27

<400> SEQUENCE: 52
```

-continued

```
Arg Ser Gly Gly Val Val Lys Asn Asn Phe
1               5                   10

<210> SEQ ID NO 53
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 19 - 28

<400> SEQUENCE: 53

Ser Gly Gly Val Val Lys Asn Asn Phe Val
1               5                   10

<210> SEQ ID NO 54
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 20 - 29

<400> SEQUENCE: 54

Gly Gly Val Val Lys Asn Asn Phe Val Pro
1               5                   10

<210> SEQ ID NO 55
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 21 - 30

<400> SEQUENCE: 55

Gly Val Val Lys Asn Asn Phe Val Pro Thr
1               5                   10

<210> SEQ ID NO 56
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 22 - 31

<400> SEQUENCE: 56

Val Val Lys Asn Asn Phe Val Pro Thr Asn
1               5                   10

<210> SEQ ID NO 57
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 23 - 32

<400> SEQUENCE: 57

Val Lys Asn Asn Phe Val Pro Thr Asn Val
1               5                   10
```

```
<210> SEQ ID NO 58
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 24 - 33

<400> SEQUENCE: 58

Lys Asn Asn Phe Val Pro Thr Asn Val Gly
1               5                   10

<210> SEQ ID NO 59
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 25 - 34

<400> SEQUENCE: 59

Asn Asn Phe Val Pro Thr Asn Val Gly Ser
1               5                   10

<210> SEQ ID NO 60
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 26 - 35

<400> SEQUENCE: 60

Asn Phe Val Pro Thr Asn Val Gly Ser Lys
1               5                   10

<210> SEQ ID NO 61
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 27 - 36

<400> SEQUENCE: 61

Phe Val Pro Thr Asn Val Gly Ser Lys Ala
1               5                   10

<210> SEQ ID NO 62
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 28 - 37

<400> SEQUENCE: 62

Val Pro Thr Asn Val Gly Ser Lys Ala Phe
1               5                   10

<210> SEQ ID NO 63
<211> LENGTH: 10
<212> TYPE: PRT
```

```
<213> ORGANISM: Homo sapiens
<220> FEATURE:
<221> NAME/KEY: PEPTIDE
<222> LOCATION: (1)..(10)
<223> OTHER INFORMATION: alpha-CGRP 29 - 38

<400> SEQUENCE: 63

Pro Thr Asn Val Gly Ser Lys Ala Phe Gly
1               5                   10

<210> SEQ ID NO 64
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 30 - 39

<400> SEQUENCE: 64

Thr Asn Val Gly Ser Lys Ala Phe Gly Arg
1               5                   10

<210> SEQ ID NO 65
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 31 - 40

<400> SEQUENCE: 65

Asn Val Gly Ser Lys Ala Phe Gly Arg Arg
1               5                   10

<210> SEQ ID NO 66
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 32 - 41

<400> SEQUENCE: 66

Val Gly Ser Lys Ala Phe Gly Arg Arg Arg
1               5                   10

<210> SEQ ID NO 67
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 33 - 42

<400> SEQUENCE: 67

Gly Ser Lys Ala Phe Gly Arg Arg Arg Arg
1               5                   10

<210> SEQ ID NO 68
<211> LENGTH: 10
<212> TYPE: PRT
<213> ORGANISM: Homo sapiens
<220> FEATURE:
<221> NAME/KEY: PEPTIDE
<222> LOCATION: (1)..(10)
```

-continued

```
<223> OTHER INFORMATION: alpha-CGRP 34 - 43

<400> SEQUENCE: 68

Ser Lys Ala Phe Gly Arg Arg Arg Arg Asp
1               5                   10

<210> SEQ ID NO 69
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 35 - 44

<400> SEQUENCE: 69

Lys Ala Phe Gly Arg Arg Arg Arg Asp Leu
1               5                   10

<210> SEQ ID NO 70
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: alpha-CGRP 36 - 45

<400> SEQUENCE: 70

Ala Phe Gly Arg Arg Arg Arg Asp Leu Gln
1               5                   10

<210> SEQ ID NO 71
<211> LENGTH: 6
<212> TYPE: PRT
<213> ORGANISM: Artificial Sequence
<220> FEATURE:
<223> OTHER INFORMATION: Synthetic Peptide - Spacer
<220> FEATURE:
<221> NAME/KEY: PEPTIDE
<222> LOCATION: (1)..(6)
<223> OTHER INFORMATION: Flexible Hinge Spacer
<220> FEATURE:
<221> NAME/KEY: SITE
<222> LOCATION: (3)..(3)
<223> OTHER INFORMATION: Xaa is any amino acid, preferably Asp
<220> FEATURE:
<221> NAME/KEY: SITE
<222> LOCATION: (5)..(5)
<223> OTHER INFORMATION: Xaa is any amino acid, preferably Asp

<400> SEQUENCE: 71

Pro Pro Xaa Pro Xaa Pro
1               5

<210> SEQ ID NO 72
<211> LENGTH: 4
<212> TYPE: PRT
<213> ORGANISM: Artificial Sequence
<220> FEATURE:
<223> OTHER INFORMATION: Synthetic Peptide - Spacer
<220> FEATURE:
<221> NAME/KEY: SITE
<222> LOCATION: (1)..(1)
<223> OTHER INFORMATION: epsilon-K
<220> FEATURE:
<221> NAME/KEY: PEPTIDE
<222> LOCATION: (1)..(4)
<223> OTHER INFORMATION: epsilon-K-KKK as a spacer

<400> SEQUENCE: 72
```

Lys Lys Lys Lys
1

<210> SEQ ID NO 73
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(4)
<223> OTHER INFORMATION: KKK-epsilon-K Spacer
<220> FEATURE:
<221> NAME/KEY: SITE
<222> LOCATION: (1)..(4)
<223> OTHER INFORMATION: epsilon K

<400> SEQUENCE: 73

Lys Lys Lys Lys
1

<210> SEQ ID NO 74
<211> LENGTH: 17
<212> TYPE: PRT
<213> ORGANISM: Clostridium tetani
<220> FEATURE:
<221> NAME/KEY: PEPTIDE
<222> LOCATION: (1)..(17)
<223> OTHER INFORMATION: Clostridium tetani 1 Th

<400> SEQUENCE: 74

Lys Lys Gln Tyr Ile Lys Ala Asn Ser Lys Phe Ile Gly Ile Thr Glu
1               5                   10                  15

Leu

<210> SEQ ID NO 75
<211> LENGTH: 15
<212> TYPE: PRT
<213> ORGANISM: Measles virus
<220> FEATURE:
<221> NAME/KEY: PEPTIDE
<222> LOCATION: (1)..(15)
<223> OTHER INFORMATION: MvF1 Th

<400> SEQUENCE: 75

Leu Ser Glu Ile Lys Gly Val Ile Val His Arg Leu Glu Gly Val
1               5                   10                  15

<210> SEQ ID NO 76
<211> LENGTH: 24
<212> TYPE: PRT
<213> ORGANISM: Bordetella pertussis
<220> FEATURE:
<221> NAME/KEY: PEPTIDE
<222> LOCATION: (1)..(24)
<223> OTHER INFORMATION: Bordetella pertussis Th

<400> SEQUENCE: 76

Gly Ala Tyr Ala Arg Cys Pro Asn Gly Thr Arg Ala Leu Thr Val Ala
1               5                   10                  15

Glu Leu Arg Gly Asn Ala Glu Leu
            20

<210> SEQ ID NO 77
<211> LENGTH: 17
<212> TYPE: PRT

```
<213> ORGANISM: Clostridium tetani
<220> FEATURE:
<221> NAME/KEY: PEPTIDE
<222> LOCATION: (1)..(17)
<223> OTHER INFORMATION: Clostridium tetani 2 Th

<400> SEQUENCE: 77

Trp Val Arg Asp Ile Ile Asp Asp Phe Thr Asn Glu Ser Ser Gln Lys
1               5                   10                  15

Thr

<210> SEQ ID NO 78
<211> LENGTH: 23
<212> TYPE: PRT
<213> ORGANISM: diphtheria bacilli
<220> FEATURE:
<221> NAME/KEY: PEPTIDE
<222> LOCATION: (1)..(23)
<223> OTHER INFORMATION: Diphtheria Th

<400> SEQUENCE: 78

Asp Ser Glu Thr Ala Asp Asn Leu Glu Lys Thr Val Ala Ala Leu Ser
1               5                   10                  15

Ile Leu Pro Gly His Gly Cys
            20

<210> SEQ ID NO 79
<211> LENGTH: 21
<212> TYPE: PRT
<213> ORGANISM: Plasmodium falciparum
<220> FEATURE:
<221> NAME/KEY: PEPTIDE
<222> LOCATION: (1)..(21)
<223> OTHER INFORMATION: Plasmodium falciparum Th

<400> SEQUENCE: 79

Asp His Glu Lys Lys His Ala Lys Met Glu Lys Ala Ser Ser Val Phe
1               5                   10                  15

Asn Val Val Asn Ser
            20

<210> SEQ ID NO 80
<211> LENGTH: 17
<212> TYPE: PRT
<213> ORGANISM: Schistosoma mansoni
<220> FEATURE:
<221> NAME/KEY: PEPTIDE
<222> LOCATION: (1)..(17)
<223> OTHER INFORMATION: Schistosoma mansoni Th

<400> SEQUENCE: 80

Lys Trp Phe Lys Thr Asn Ala Pro Asn Gly Val Asp Glu Lys His Arg
1               5                   10                  15

His

<210> SEQ ID NO 81
<211> LENGTH: 25
<212> TYPE: PRT
<213> ORGANISM: Cholera Toxin
<220> FEATURE:
<221> NAME/KEY: PEPTIDE
<222> LOCATION: (1)..(25)
<223> OTHER INFORMATION: Cholera Toxin Th

<400> SEQUENCE: 81

Ala Leu Asn Ile Trp Asp Arg Phe Asp Val Phe Cys Thr Leu Gly Ala
```

-continued

```
1               5               10              15

Thr Thr Gly Tyr Leu Lys Gly Asn Ser
                20              25

<210> SEQ ID NO 82
<211> LENGTH: 15
<212> TYPE: PRT
<213> ORGANISM: Measles virus
<220> FEATURE:
<221> NAME/KEY: PEPTIDE
<222> LOCATION: (1)..(15)
<223> OTHER INFORMATION: MvF 2 Th

<400> SEQUENCE: 82

Ile Ser Glu Ile Lys Gly Val Ile Val His Lys Ile Glu Gly Ile
1               5               10              15

<210> SEQ ID NO 83
<211> LENGTH: 22
<212> TYPE: PRT
<213> ORGANISM: Artificial Sequence
<220> FEATURE:
<223> OTHER INFORMATION: KKKMvF3 Th epitope

<400> SEQUENCE: 83

Lys Lys Lys Ile Ser Ile Ser Glu Ile Lys Gly Val Ile Val His Lys
1               5               10              15

Ile Glu Gly Ile Leu Phe
            20

<210> SEQ ID NO 84
<211> LENGTH: 22
<212> TYPE: PRT
<213> ORGANISM: Artificial Sequence
<220> FEATURE:
<223> OTHER INFORMATION: KKKMvF3 Th epitope

<400> SEQUENCE: 84

Lys Lys Lys Ile Ser Ile Thr Glu Ile Arg Thr Val Ile Val Thr Arg
1               5               10              15

Ile Glu Thr Ile Leu Phe
            20

<210> SEQ ID NO 85
<211> LENGTH: 22
<212> TYPE: PRT
<213> ORGANISM: Measles virus
<220> FEATURE:
<221> NAME/KEY: PEPTIDE
<222> LOCATION: (1)..(22)
<223> OTHER INFORMATION: KKKMvF 3 Th
<220> FEATURE:
<221> NAME/KEY: SITE
<222> LOCATION: (7)..(7)
<223> OTHER INFORMATION: S or T
<220> FEATURE:
<221> NAME/KEY: SITE
<222> LOCATION: (10)..(10)
<223> OTHER INFORMATION: K or R
<220> FEATURE:
<221> NAME/KEY: SITE
<222> LOCATION: (11)..(11)
<223> OTHER INFORMATION: G or T
<220> FEATURE:
<221> NAME/KEY: SITE
<222> LOCATION: (15)..(15)
<223> OTHER INFORMATION: H or T
<220> FEATURE:
<221> NAME/KEY: SITE
```

```
<222> LOCATION: (16)..(16)
<223> OTHER INFORMATION: K or R
<220> FEATURE:
<221> NAME/KEY: SITE
<222> LOCATION: (19)..(19)
<223> OTHER INFORMATION: G or T

<400> SEQUENCE: 85

Lys Lys Lys Ile Ser Ile Xaa Glu Ile Xaa Xaa Val Ile Val Xaa Xaa
1               5                   10                  15

Ile Glu Xaa Ile Leu Phe
            20

<210> SEQ ID NO 86
<211> LENGTH: 18
<212> TYPE: PRT
<213> ORGANISM: Artificial Sequence
<220> FEATURE:
<223> OTHER INFORMATION: HBsAg1 Th epitope

<400> SEQUENCE: 86

Lys Lys Lys Leu Phe Leu Leu Thr Lys Leu Leu Thr Leu Pro Gln Ser
1               5                   10                  15

Leu Asp

<210> SEQ ID NO 87
<211> LENGTH: 18
<212> TYPE: PRT
<213> ORGANISM: Artificial Sequence
<220> FEATURE:
<223> OTHER INFORMATION: HBsAg1 Th epitope

<400> SEQUENCE: 87

Arg Arg Arg Ile Lys Ile Ile Thr Arg Ile Ile Thr Ile Pro Leu Ser
1               5                   10                  15

Ile Arg

<210> SEQ ID NO 88
<211> LENGTH: 18
<212> TYPE: PRT
<213> ORGANISM: Artificial Sequence
<220> FEATURE:
<223> OTHER INFORMATION: HBsAg1 Th epitope

<400> SEQUENCE: 88

Lys Lys Lys Val Arg Val Val Thr Lys Val Val Thr Val Pro Ile Ser
1               5                   10                  15

Val Asp

<210> SEQ ID NO 89
<211> LENGTH: 18
<212> TYPE: PRT
<213> ORGANISM: Artificial Sequence
<220> FEATURE:
<223> OTHER INFORMATION: HBsAg1 Th epitope

<400> SEQUENCE: 89

Lys Lys Lys Phe Phe Phe Phe Thr Lys Phe Phe Thr Phe Pro Val Ser
1               5                   10                  15

Phe Asp

<210> SEQ ID NO 90
<211> LENGTH: 18
<212> TYPE: PRT
```

-continued

```
<213> ORGANISM: Artificial Sequence
<220> FEATURE:
<223> OTHER INFORMATION: HBsAg1 Th epitope

<400> SEQUENCE: 90

Lys Lys Lys Leu Phe Leu Leu Thr Lys Leu Leu Thr Leu Pro Phe Ser
1               5                   10                  15

Leu Asp

<210> SEQ ID NO 91
<211> LENGTH: 18
<212> TYPE: PRT
<213> ORGANISM: Hepatitis B virus
<220> FEATURE:
<221> NAME/KEY: PEPTIDE
<222> LOCATION: (1)..(18)
<223> OTHER INFORMATION: HBsAg 1 Th
<220> FEATURE:
<221> NAME/KEY: SITE
<222> LOCATION: (1)..(1)
<223> OTHER INFORMATION: K or R
<220> FEATURE:
<221> NAME/KEY: SITE
<222> LOCATION: (2)..(2)
<223> OTHER INFORMATION: K or R
<220> FEATURE:
<221> NAME/KEY: SITE
<222> LOCATION: (3)..(3)
<223> OTHER INFORMATION: K or R
<220> FEATURE:
<221> NAME/KEY: SITE
<222> LOCATION: (4)..(4)
<223> OTHER INFORMATION: L or I or V or F
<220> FEATURE:
<221> NAME/KEY: SITE
<222> LOCATION: (5)..(5)
<223> OTHER INFORMATION: F or K or R
<220> FEATURE:
<221> NAME/KEY: SITE
<222> LOCATION: (6)..(6)
<223> OTHER INFORMATION: L or I or V or F
<220> FEATURE:
<221> NAME/KEY: SITE
<222> LOCATION: (7)..(7)
<223> OTHER INFORMATION: L or I or V or F
<220> FEATURE:
<221> NAME/KEY: SITE
<222> LOCATION: (9)..(9)
<223> OTHER INFORMATION: K or R
<220> FEATURE:
<221> NAME/KEY: SITE
<222> LOCATION: (10)..(10)
<223> OTHER INFORMATION: L or I or V or F
<220> FEATURE:
<221> NAME/KEY: SITE
<222> LOCATION: (11)..(11)
<223> OTHER INFORMATION: L or I or V or F
<220> FEATURE:
<221> NAME/KEY: SITE
<222> LOCATION: (13)..(13)
<223> OTHER INFORMATION: L or I or V or F
<220> FEATURE:
<221> NAME/KEY: SITE
<222> LOCATION: (15)..(15)
<223> OTHER INFORMATION: Q or L or I or V or F
<220> FEATURE:
<221> NAME/KEY: SITE
<222> LOCATION: (17)..(17)
<223> OTHER INFORMATION: L or I or V or F
<220> FEATURE:
<221> NAME/KEY: SITE
<222> LOCATION: (18)..(18)
<223> OTHER INFORMATION: D or R

<400> SEQUENCE: 91
```

-continued

```
Xaa Xaa Xaa Xaa Xaa Xaa Xaa Thr Xaa Xaa Xaa Thr Xaa Pro Xaa Ser
1               5                   10                  15

Xaa Xaa

<210> SEQ ID NO 92
<211> LENGTH: 19
<212> TYPE: PRT
<213> ORGANISM: Artificial Sequence
<220> FEATURE:
<223> OTHER INFORMATION: MvF4 Th epitope (UBITh3)

<400> SEQUENCE: 92

Ile Ser Ile Ser Glu Ile Lys Gly Val Ile Val His Lys Ile Glu Thr
1               5                   10                  15

Ile Leu Phe

<210> SEQ ID NO 93
<211> LENGTH: 19
<212> TYPE: PRT
<213> ORGANISM: Artificial Sequence
<220> FEATURE:
<223> OTHER INFORMATION: MvF4 Th epitope (UBITh3)

<400> SEQUENCE: 93

Ile Ser Ile Thr Glu Ile Arg Thr Val Ile Val Thr Arg Ile Glu Thr
1               5                   10                  15

Ile Leu Phe

<210> SEQ ID NO 94
<211> LENGTH: 19
<212> TYPE: PRT
<213> ORGANISM: Measles virus
<220> FEATURE:
<221> NAME/KEY: PEPTIDE
<222> LOCATION: (1)..(19)
<223> OTHER INFORMATION: MvF 4 Th
<220> FEATURE:
<221> NAME/KEY: SITE
<222> LOCATION: (4)..(4)
<223> OTHER INFORMATION: S or T
<220> FEATURE:
<221> NAME/KEY: SITE
<222> LOCATION: (7)..(7)
<223> OTHER INFORMATION: K or R
<220> FEATURE:
<221> NAME/KEY: SITE
<222> LOCATION: (8)..(8)
<223> OTHER INFORMATION: G or T
<220> FEATURE:
<221> NAME/KEY: SITE
<222> LOCATION: (12)..(12)
<223> OTHER INFORMATION: H or T
<220> FEATURE:
<221> NAME/KEY: SITE
<222> LOCATION: (13)..(13)
<223> OTHER INFORMATION: K or R

<400> SEQUENCE: 94

Ile Ser Ile Xaa Glu Ile Xaa Xaa Val Ile Val Xaa Xaa Ile Glu Thr
1               5                   10                  15

Ile Leu Phe

<210> SEQ ID NO 95
<211> LENGTH: 18
<212> TYPE: PRT
<213> ORGANISM: Artificial Sequence
<220> FEATURE:
<223> OTHER INFORMATION: HBsAg2 Th epitope
```

<400> SEQUENCE: 95

Lys Lys Lys Ile Ile Thr Ile Thr Arg Ile Ile Thr Ile Pro Gln Ser
1               5                   10                  15

Leu Asp

<210> SEQ ID NO 96
<211> LENGTH: 18
<212> TYPE: PRT
<213> ORGANISM: Artificial Sequence
<220> FEATURE:
<223> OTHER INFORMATION: HBsAg2 Th epitope

<400> SEQUENCE: 96

Lys Lys Lys Phe Phe Leu Leu Thr Arg Ile Leu Thr Ile Ile Thr Thr
1               5                   10                  15

Ile Asp

<210> SEQ ID NO 97
<211> LENGTH: 18
<212> TYPE: PRT
<213> ORGANISM: Hepatitis B virus
<220> FEATURE:
<221> NAME/KEY: PEPTIDE
<222> LOCATION: (1)..(18)
<223> OTHER INFORMATION: HBsAg 2 Th
<220> FEATURE:
<221> NAME/KEY: SITE
<222> LOCATION: (4)..(4)
<223> OTHER INFORMATION: I or F
<220> FEATURE:
<221> NAME/KEY: SITE
<222> LOCATION: (5)..(5)
<223> OTHER INFORMATION: I or F
<220> FEATURE:
<221> NAME/KEY: SITE
<222> LOCATION: (6)..(6)
<223> OTHER INFORMATION: T or L
<220> FEATURE:
<221> NAME/KEY: SITE
<222> LOCATION: (7)..(7)
<223> OTHER INFORMATION: I or L
<220> FEATURE:
<221> NAME/KEY: SITE
<222> LOCATION: (11)..(11)
<223> OTHER INFORMATION: I or L
<220> FEATURE:
<221> NAME/KEY: SITE
<222> LOCATION: (14)..(14)
<223> OTHER INFORMATION: P or I
<220> FEATURE:
<221> NAME/KEY: SITE
<222> LOCATION: (15)..(15)
<223> OTHER INFORMATION: Q or T
<220> FEATURE:
<221> NAME/KEY: SITE
<222> LOCATION: (16)..(16)
<223> OTHER INFORMATION: S or T
<220> FEATURE:
<221> NAME/KEY: SITE
<222> LOCATION: (17)..(17)
<223> OTHER INFORMATION: L or I

<400> SEQUENCE: 97

Lys Lys Lys Xaa Xaa Xaa Xaa Thr Arg Ile Xaa Thr Ile Xaa Xaa Xaa
1               5                   10                  15

Xaa Asp

<210> SEQ ID NO 98
<211> LENGTH: 19

-continued

```
<212> TYPE: PRT
<213> ORGANISM: Measles virus
<220> FEATURE:
<221> NAME/KEY: PEPTIDE
<222> LOCATION: (1)..(19)
<223> OTHER INFORMATION: MvF 5 Th

<400> SEQUENCE: 98

Ile Ser Ile Thr Glu Ile Lys Gly Val Ile Val His Arg Ile Glu Thr
1               5                   10                  15

Ile Leu Phe

<210> SEQ ID NO 99
<211> LENGTH: 18
<212> TYPE: PRT
<213> ORGANISM: Hepatitis B virus
<220> FEATURE:
<221> NAME/KEY: PEPTIDE
<222> LOCATION: (1)..(18)
<223> OTHER INFORMATION: HBsAg 3 Th

<400> SEQUENCE: 99

Lys Lys Lys Ile Ile Thr Ile Thr Arg Ile Ile Thr Ile Ile Thr Thr
1               5                   10                  15

Ile Asp

<210> SEQ ID NO 100
<211> LENGTH: 11
<212> TYPE: PRT
<213> ORGANISM: Influenza virus
<220> FEATURE:
<221> NAME/KEY: PEPTIDE
<222> LOCATION: (1)..(11)
<223> OTHER INFORMATION: Influenza Matrix protein 1 _1 Th
<220> FEATURE:
<221> NAME/KEY: PEPTIDE
<222> LOCATION: (1)..(11)
<223> OTHER INFORMATION: Influenza Matrix protein 1_1 Th

<400> SEQUENCE: 100

Phe Val Phe Thr Leu Thr Val Pro Ser Glu Arg
1               5                   10

<210> SEQ ID NO 101
<211> LENGTH: 15
<212> TYPE: PRT
<213> ORGANISM: Influenza virus
<220> FEATURE:
<221> NAME/KEY: PEPTIDE
<222> LOCATION: (1)..(15)
<223> OTHER INFORMATION: Influenza Matrix protein 1_2 Th

<400> SEQUENCE: 101

Ser Gly Pro Leu Lys Ala Glu Ile Ala Gln Arg Leu Glu Asp Val
1               5                   10                  15

<210> SEQ ID NO 102
<211> LENGTH: 9
<212> TYPE: PRT
<213> ORGANISM: Influenza virus
<220> FEATURE:
<221> NAME/KEY: PEPTIDE
<222> LOCATION: (1)..(9)
<223> OTHER INFORMATION: Influenza Non-structural protein 1 Th

<400> SEQUENCE: 102

Asp Arg Leu Arg Arg Asp Gln Lys Ser
1               5
```

-continued

```
<210> SEQ ID NO 103
<211> LENGTH: 19
<212> TYPE: PRT
<213> ORGANISM: Epstein-Barr virus
<220> FEATURE:
<221> NAME/KEY: PEPTIDE
<222> LOCATION: (1)..(19)
<223> OTHER INFORMATION: EBV BHRF1 Th

<400> SEQUENCE: 103

Ala Gly Leu Thr Leu Ser Leu Leu Val Ile Cys Ser Tyr Leu Phe Ile
1               5                   10                  15

Ser Arg Gly

<210> SEQ ID NO 104
<211> LENGTH: 15
<212> TYPE: PRT
<213> ORGANISM: Clostridium tetani
<220> FEATURE:
<221> NAME/KEY: PEPTIDE
<222> LOCATION: (1)..(15)
<223> OTHER INFORMATION: Clostridium tetani TT1 Th

<400> SEQUENCE: 104

Gln Tyr Ile Lys Ala Asn Ser Lys Phe Ile Gly Ile Thr Glu Leu
1               5                   10                  15

<210> SEQ ID NO 105
<211> LENGTH: 20
<212> TYPE: PRT
<213> ORGANISM: Epstein-Barr virus
<220> FEATURE:
<221> NAME/KEY: PEPTIDE
<222> LOCATION: (1)..(20)
<223> OTHER INFORMATION: EBV EBNA-1 Th

<400> SEQUENCE: 105

Pro Gly Pro Leu Arg Glu Ser Ile Val Cys Tyr Phe Met Val Phe Leu
1               5                   10                  15

Gln Thr His Ile
            20

<210> SEQ ID NO 106
<211> LENGTH: 21
<212> TYPE: PRT
<213> ORGANISM: Clostridium tetani
<220> FEATURE:
<221> NAME/KEY: PEPTIDE
<222> LOCATION: (1)..(21)
<223> OTHER INFORMATION: Clostridium tetani  TT2 Th

<400> SEQUENCE: 106

Phe Asn Asn Phe Thr Val Ser Phe Trp Leu Arg Val Pro Lys Val Ser
1               5                   10                  15

Ala Ser His Leu Glu
            20

<210> SEQ ID NO 107
<211> LENGTH: 16
<212> TYPE: PRT
<213> ORGANISM: Clostridium tetani
<220> FEATURE:
<221> NAME/KEY: PEPTIDE
<222> LOCATION: (1)..(16)
<223> OTHER INFORMATION: Clostridium tetani TT3 Th
```

-continued

```
<400> SEQUENCE: 107

Lys Phe Ile Ile Lys Arg Tyr Thr Pro Asn Asn Glu Ile Asp Ser Phe
1               5                   10                  15

<210> SEQ ID NO 108
<211> LENGTH: 16
<212> TYPE: PRT
<213> ORGANISM: Clostridium tetani
<220> FEATURE:
<221> NAME/KEY: PEPTIDE
<222> LOCATION: (1)..(16)
<223> OTHER INFORMATION: Clostridium tetani  TT4 Th

<400> SEQUENCE: 108

Val Ser Ile Asp Lys Phe Arg Ile Phe Cys Lys Ala Leu Asn Pro Lys
1               5                   10                  15

<210> SEQ ID NO 109
<211> LENGTH: 18
<212> TYPE: PRT
<213> ORGANISM: Epstein-Barr virus
<220> FEATURE:
<221> NAME/KEY: PEPTIDE
<222> LOCATION: (1)..(18)
<223> OTHER INFORMATION: EBV CP Th

<400> SEQUENCE: 109

Val Pro Gly Leu Tyr Ser Pro Cys Arg Ala Phe Phe Asn Lys Glu Glu
1               5                   10                  15

Leu Leu

<210> SEQ ID NO 110
<211> LENGTH: 14
<212> TYPE: PRT
<213> ORGANISM: Human cytomegalovirus
<220> FEATURE:
<221> NAME/KEY: PEPTIDE
<222> LOCATION: (1)..(14)
<223> OTHER INFORMATION: HCMV IE1 Th

<400> SEQUENCE: 110

Asp Lys Arg Glu Met Trp Met Ala Cys Ile Lys Glu Leu His
1               5                   10

<210> SEQ ID NO 111
<211> LENGTH: 15
<212> TYPE: PRT
<213> ORGANISM: Epstein-Barr virus
<220> FEATURE:
<221> NAME/KEY: PEPTIDE
<222> LOCATION: (1)..(15)
<223> OTHER INFORMATION: EBV GP340 Th

<400> SEQUENCE: 111

Thr Gly His Gly Ala Arg Thr Ser Thr Glu Pro Thr Thr Asp Tyr
1               5                   10                  15

<210> SEQ ID NO 112
<211> LENGTH: 13
<212> TYPE: PRT
<213> ORGANISM: Epstein-Barr virus
<220> FEATURE:
<221> NAME/KEY: PEPTIDE
<222> LOCATION: (1)..(13)
<223> OTHER INFORMATION: EBV BPLF1 Th

<400> SEQUENCE: 112
```

-continued

```
Lys Glu Leu Lys Arg Gln Tyr Glu Lys Lys Leu Arg Gln
1               5                   10
```

<210> SEQ ID NO 113
<211> LENGTH: 11
<212> TYPE: PRT
<213> ORGANISM: Epstein-Barr virus
<220> FEATURE:
<221> NAME/KEY: PEPTIDE
<222> LOCATION: (1)..(11)
<223> OTHER INFORMATION: EBV EBNA-2 Th

<400> SEQUENCE: 113

```
Thr Val Phe Tyr Asn Ile Pro Pro Met Pro Leu
1               5                   10
```

<210> SEQ ID NO 114
<211> LENGTH: 15
<212> TYPE: PRT
<213> ORGANISM: Hepatitis B virus
<220> FEATURE:
<221> NAME/KEY: PEPTIDE
<222> LOCATION: (1)..(15)
<223> OTHER INFORMATION: HBsAg4 Th (UBITh4)

<400> SEQUENCE: 114

```
Phe Phe Leu Leu Thr Arg Ile Leu Thr Ile Pro Gln Ser Leu Asp
1               5                   10                  15
```

<210> SEQ ID NO 115
<211> LENGTH: 25
<212> TYPE: PRT
<213> ORGANISM: Yersinia enterocolitica
<220> FEATURE:
<221> NAME/KEY: PEPTIDE
<222> LOCATION: (1)..(25)
<223> OTHER INFORMATION: Yersinia Invasin Th (Inv)

<400> SEQUENCE: 115

```
Ala Leu Asn Ile Trp Asp Arg Phe Asp Val Phe Cys Thr Leu Gly Ala
1               5                   10                  15

Thr Thr Gly Tyr Leu Lys Gly Asn Ser
            20                  25
```

<210> SEQ ID NO 116
<211> LENGTH: 33
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(33)
<223> OTHER INFORMATION: alpha-CGRP 1-10

<400> SEQUENCE: 116

```
Ile Ser Ile Thr Glu Ile Lys Gly Val Ile Val His Arg Ile Glu Thr
1               5                   10                  15
```

-continued

```
Ile Leu Phe Lys Lys Lys Lys Ala Cys Asp Thr Ala Thr Cys Val Thr
            20                  25                  30

His
```

<210> SEQ ID NO 117
<211> LENGTH: 33
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(10)
<223> OTHER INFORMATION: alpha-CGRP 1-10
<220> FEATURE:
<221> NAME/KEY: SITE
<222> LOCATION: (11)..(11)
<223> OTHER INFORMATION: epsilon K
<220> FEATURE:
<221> NAME/KEY: PEPTIDE
<222> LOCATION: (11)..(14)
<223> OTHER INFORMATION: KKK-epsilon K as a spacer
<220> FEATURE:
<221> NAME/KEY: PEPTIDE
<222> LOCATION: (15)..(33)
<223> OTHER INFORMATION: MvF5 Th (UBITh1)

<400> SEQUENCE: 117

```
Ala Cys Asp Thr Ala Thr Cys Val Thr His Lys Lys Lys Lys Ile Ser
1               5                   10                  15

Ile Thr Glu Ile Lys Gly Val Ile Val His Arg Ile Glu Thr Ile Leu
            20                  25                  30

Phe
```

<210> SEQ ID NO 118
<211> LENGTH: 56
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon K as a spacer
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(33)
<223> OTHER INFORMATION: alpha-CGRP 1-10
<220> FEATURE:
<221> NAME/KEY: PEPTIDE
<222> LOCATION: (34)..(37)
<223> OTHER INFORMATION: epsilon K-KKK as a spacer
<220> FEATURE:
<221> NAME/KEY: SITE
<222> LOCATION: (37)..(37)
<223> OTHER INFORMATION: epsilon K as a spacer
<220> FEATURE:
<221> NAME/KEY: PEPTIDE
<222> LOCATION: (38)..(56)
<223> OTHER INFORMATION: MvF5 Th (UBITh1)

<400> SEQUENCE: 118

```
Ile Ser Ile Thr Glu Ile Lys Gly Val Ile Val His Arg Ile Glu Thr
```

-continued

```
1               5                   10                  15

Ile Leu Phe Lys Lys Lys Lys Ala Cys Asp Thr Ala Thr Cys Val Thr
            20                  25                  30

His Lys Lys Lys Lys Ile Ser Ile Thr Glu Ile Lys Gly Val Ile Val
        35                  40                  45

His Arg Ile Glu Thr Ile Leu Phe
    50                  55

<210> SEQ ID NO 119
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(30)
<223> OTHER INFORMATION: alpha-CGRP 31-37

<400> SEQUENCE: 119

Ile Ser Ile Thr Glu Ile Lys Gly Val Ile Val His Arg Ile Glu Thr
1               5                   10                  15

Ile Leu Phe Lys Lys Lys Lys Asn Val Gly Ser Lys Ala Phe
            20                  25                  30

<210> SEQ ID NO 120
<211> LENGTH: 33
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(33)
<223> OTHER INFORMATION: alpha-CGRP 28-37

<400> SEQUENCE: 120

Ile Ser Ile Thr Glu Ile Lys Gly Val Ile Val His Arg Ile Glu Thr
1               5                   10                  15

Ile Leu Phe Lys Lys Lys Lys Val Pro Thr Asn Val Gly Ser Lys Ala
            20                  25                  30

Phe

<210> SEQ ID NO 121
```

<211> LENGTH: 36
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(36)
<223> OTHER INFORMATION: alpha-CGRP 25-37

<400> SEQUENCE: 121

Ile Ser Ile Thr Glu Ile Lys Gly Val Ile Val His Arg Ile Glu Thr
1               5                   10                  15

Ile Leu Phe Lys Lys Lys Lys Asn Asn Phe Val Pro Thr Asn Val Gly
            20                  25                  30

Ser Lys Ala Phe
        35

<210> SEQ ID NO 122
<211> LENGTH: 43
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(43)
<223> OTHER INFORMATION: alpha-CGRP 18-37

<400> SEQUENCE: 122

Ile Ser Ile Thr Glu Ile Lys Gly Val Ile Val His Arg Ile Glu Thr
1               5                   10                  15

Ile Leu Phe Lys Lys Lys Lys Arg Ser Gly Gly Val Val Lys Asn Asn
            20                  25                  30

Phe Val Pro Thr Asn Val Gly Ser Lys Ala Phe
        35                  40

<210> SEQ ID NO 123
<211> LENGTH: 50
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)

```
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(50)
<223> OTHER INFORMATION: alpha-CGRP 11-37

<400> SEQUENCE: 123

Ile Ser Ile Thr Glu Ile Lys Gly Val Ile Val His Arg Ile Glu Thr
1               5                   10                  15

Ile Leu Phe Lys Lys Lys Lys Arg Leu Ala Gly Leu Leu Ser Arg Ser
            20                  25                  30

Gly Gly Val Val Lys Asn Asn Phe Val Pro Thr Asn Val Gly Ser Lys
        35                  40                  45

Ala Phe
    50

<210> SEQ ID NO 124
<211> LENGTH: 38
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(15)
<223> OTHER INFORMATION: alpha-CGRP 1-15
<220> FEATURE:
<221> NAME/KEY: SITE
<222> LOCATION: (16)..(16)
<223> OTHER INFORMATION: epsilon K
<220> FEATURE:
<221> NAME/KEY: PEPTIDE
<222> LOCATION: (16)..(19)
<223> OTHER INFORMATION: KKK-epsilon K as a spacer
<220> FEATURE:
<221> NAME/KEY: PEPTIDE
<222> LOCATION: (20)..(38)
<223> OTHER INFORMATION: MvF5 Th (UBITh1)

<400> SEQUENCE: 124

Ala Cys Asp Thr Ala Thr Cys Val Thr His Arg Leu Ala Gly Leu Lys
1               5                   10                  15

Lys Lys Lys Ile Ser Ile Thr Glu Ile Lys Gly Val Ile Val His Arg
            20                  25                  30

Ile Glu Thr Ile Leu Phe
        35

<210> SEQ ID NO 125
<211> LENGTH: 41
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(18)
<223> OTHER INFORMATION: alpha-CGRP 1-18
<220> FEATURE:
<221> NAME/KEY: SITE
<222> LOCATION: (19)..(19)
<223> OTHER INFORMATION: epsilon K
<220> FEATURE:
<221> NAME/KEY: PEPTIDE
```

-continued

```
<222> LOCATION: (19)..(22)
<223> OTHER INFORMATION: KKK-epsilon K as a spacer
<220> FEATURE:
<221> NAME/KEY: PEPTIDE
<222> LOCATION: (23)..(41)
<223> OTHER INFORMATION: MvF5 Th (UBITh1)

<400> SEQUENCE: 125

Ala Cys Asp Thr Ala Thr Cys Val Thr His Arg Leu Ala Gly Leu Leu
1               5                   10                  15

Ser Arg Lys Lys Lys Lys Ile Ser Ile Thr Glu Ile Lys Gly Val Ile
            20                  25                  30

Val His Arg Ile Glu Thr Ile Leu Phe
        35                  40

<210> SEQ ID NO 126
<211> LENGTH: 43
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(20)
<223> OTHER INFORMATION: alpha-CGRP 1-20
<220> FEATURE:
<221> NAME/KEY: SITE
<222> LOCATION: (21)..(21)
<223> OTHER INFORMATION: epsilon K
<220> FEATURE:
<221> NAME/KEY: PEPTIDE
<222> LOCATION: (21)..(24)
<223> OTHER INFORMATION: KKK-epsilon K as a spacer
<220> FEATURE:
<221> NAME/KEY: PEPTIDE
<222> LOCATION: (24)..(43)
<223> OTHER INFORMATION: MvF5 Th (UBITh1)

<400> SEQUENCE: 126

Ala Cys Asp Thr Ala Thr Cys Val Thr His Arg Leu Ala Gly Leu Leu
1               5                   10                  15

Ser Arg Ser Gly Lys Lys Lys Lys Ile Ser Ile Thr Glu Ile Lys Gly
            20                  25                  30

Val Ile Val His Arg Ile Glu Thr Ile Leu Phe
        35                  40

<210> SEQ ID NO 127
<211> LENGTH: 48
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(25)
<223> OTHER INFORMATION: alpha-CGRP 1-25
<220> FEATURE:
<221> NAME/KEY: SITE
<222> LOCATION: (26)..(26)
<223> OTHER INFORMATION: epsilon K
<220> FEATURE:
<221> NAME/KEY: PEPTIDE
<222> LOCATION: (26)..(29)
<223> OTHER INFORMATION: KKK-epsilon K as a spacer
<220> FEATURE:
<221> NAME/KEY: PEPTIDE
<222> LOCATION: (30)..(48)
<223> OTHER INFORMATION: MvF5 Th (UBITh1)

<400> SEQUENCE: 127
```

```
Ala Cys Asp Thr Ala Thr Cys Val Thr His Arg Leu Ala Gly Leu Leu
1               5                   10                  15

Ser Arg Ser Gly Gly Val Val Lys Asn Lys Lys Lys Ile Ser Ile
            20                  25                  30

Thr Glu Ile Lys Gly Val Ile Val His Arg Ile Glu Thr Ile Leu Phe
        35                  40                  45
```

<210> SEQ ID NO 128
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(11)
<223> OTHER INFORMATION: alpha-CGRP 8-18
<220> FEATURE:
<221> NAME/KEY: SITE
<222> LOCATION: (12)..(12)
<223> OTHER INFORMATION: epsilon K
<220> FEATURE:
<221> NAME/KEY: PEPTIDE
<222> LOCATION: (12)..(15)
<223> OTHER INFORMATION: KKK-epsilon K as a spacer
<220> FEATURE:
<221> NAME/KEY: PEPTIDE
<222> LOCATION: (16)..(34)
<223> OTHER INFORMATION: MvF5 Th (UBITh1)

<400> SEQUENCE: 128

```
Val Thr His Arg Leu Ala Gly Leu Leu Ser Arg Lys Lys Lys Lys Ile
1               5                   10                  15

Ser Ile Thr Glu Ile Lys Gly Val Ile Val His Arg Ile Glu Thr Ile
            20                  25                  30

Leu Phe
```

<210> SEQ ID NO 129
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(34)
<223> OTHER INFORMATION: alpha-CGRP 8-18

<400> SEQUENCE: 129

```
Ile Ser Ile Thr Glu Ile Lys Gly Val Ile Val His Arg Ile Glu Thr
1               5                   10                  15

Ile Leu Phe Lys Lys Lys Lys Val Thr His Arg Leu Ala Gly Leu Leu
            20                  25                  30

Ser Arg
```

<210> SEQ ID NO 130

<211> LENGTH: 47
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (21)..(47)
<223> OTHER INFORMATION: alpha-CGRP 11-37

<400> SEQUENCE: 130

Ile Ser Ile Thr Glu Ile Lys Gly Val Ile Val His Arg Ile Glu Thr
1               5                   10                  15

Ile Leu Phe Lys Arg Leu Ala Gly Leu Leu Ser Arg Ser Gly Gly Val
            20                  25                  30

Val Lys Asn Asn Phe Val Pro Thr Asn Val Gly Ser Lys Ala Phe
        35                  40                  45

<210> SEQ ID NO 131
<211> LENGTH: 38
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(38)
<223> OTHER INFORMATION: alpha-CGRP 11-25

<400> SEQUENCE: 131

Ile Ser Ile Thr Glu Ile Lys Gly Val Ile Val His Arg Ile Glu Thr
1               5                   10                  15

Ile Leu Phe Lys Lys Lys Lys Arg Leu Ala Gly Leu Leu Ser Arg Ser
            20                  25                  30

Gly Gly Val Val Lys Asn
        35

<210> SEQ ID NO 132
<211> LENGTH: 38
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF 4 Th (UBITh3)
<220> FEATURE:
<221> NAME/KEY: SITE
<222> LOCATION: (4)..(4)
<223> OTHER INFORMATION: S or T

```
<220> FEATURE:
<221> NAME/KEY: SITE
<222> LOCATION: (7)..(7)
<223> OTHER INFORMATION: K or R
<220> FEATURE:
<221> NAME/KEY: SITE
<222> LOCATION: (8)..(8)
<223> OTHER INFORMATION: G or T
<220> FEATURE:
<221> NAME/KEY: SITE
<222> LOCATION: (12)..(12)
<223> OTHER INFORMATION: H or T
<220> FEATURE:
<221> NAME/KEY: SITE
<222> LOCATION: (13)..(13)
<223> OTHER INFORMATION: K or R
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(38)
<223> OTHER INFORMATION: alpha-CGRP 11-25

<400> SEQUENCE: 132

Ile Ser Ile Xaa Glu Ile Xaa Xaa Val Ile Val Xaa Xaa Ile Glu Thr
1               5                   10                  15

Ile Leu Phe Lys Lys Lys Lys Arg Leu Ala Gly Leu Leu Ser Arg Ser
            20                  25                  30

Gly Gly Val Val Lys Asn
        35

<210> SEQ ID NO 133
<211> LENGTH: 43
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(43)
<223> OTHER INFORMATION: alpha-CGRP 11-30

<400> SEQUENCE: 133

Ile Ser Ile Thr Glu Ile Lys Gly Val Ile Val His Arg Ile Glu Thr
1               5                   10                  15

Ile Leu Phe Lys Lys Lys Lys Arg Leu Ala Gly Leu Leu Ser Arg Ser
            20                  25                  30

Gly Gly Val Val Lys Asn Asn Phe Val Pro Thr
        35                  40

<210> SEQ ID NO 134
<211> LENGTH: 43
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF 4 Th (UBITh3)
<220> FEATURE:
<221> NAME/KEY: SITE
<222> LOCATION: (4)..(4)
<223> OTHER INFORMATION: S or T
<220> FEATURE:
<221> NAME/KEY: SITE
<222> LOCATION: (7)..(7)
<223> OTHER INFORMATION: K or R
<220> FEATURE:
<221> NAME/KEY: SITE
<222> LOCATION: (8)..(8)
<223> OTHER INFORMATION: G or T
<220> FEATURE:
<221> NAME/KEY: SITE
<222> LOCATION: (12)..(12)
<223> OTHER INFORMATION: H or T
<220> FEATURE:
<221> NAME/KEY: SITE
<222> LOCATION: (13)..(13)
<223> OTHER INFORMATION: K or R
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(43)
<223> OTHER INFORMATION: alpha-CGRP 11-30

<400> SEQUENCE: 134

Ile Ser Ile Xaa Glu Ile Xaa Xaa Val Ile Val Xaa Xaa Ile Glu Thr
1               5                   10                  15

Ile Leu Phe Lys Lys Lys Lys Arg Leu Ala Gly Leu Leu Ser Arg Ser
            20                  25                  30

Gly Gly Val Val Lys Asn Asn Phe Val Pro Thr
        35                  40

<210> SEQ ID NO 135
<211> LENGTH: 46
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(46)
<223> OTHER INFORMATION: alpha-CGRP 11-33

<400> SEQUENCE: 135

Ile Ser Ile Thr Glu Ile Lys Gly Val Ile Val His Arg Ile Glu Thr
1               5                   10                  15
```

-continued

```
Ile Leu Phe Lys Lys Lys Lys Arg Leu Ala Gly Leu Leu Ser Arg Ser
            20                  25                  30

Gly Gly Val Val Lys Asn Asn Phe Val Pro Thr Asn Val Gly
        35                  40                  45

<210> SEQ ID NO 136
<211> LENGTH: 46
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF 4 Th (UBITh3)
<220> FEATURE:
<221> NAME/KEY: SITE
<222> LOCATION: (4)..(4)
<223> OTHER INFORMATION: S or T
<220> FEATURE:
<221> NAME/KEY: SITE
<222> LOCATION: (7)..(7)
<223> OTHER INFORMATION: K or R
<220> FEATURE:
<221> NAME/KEY: SITE
<222> LOCATION: (8)..(8)
<223> OTHER INFORMATION: G or T
<220> FEATURE:
<221> NAME/KEY: SITE
<222> LOCATION: (12)..(12)
<223> OTHER INFORMATION: H or T
<220> FEATURE:
<221> NAME/KEY: SITE
<222> LOCATION: (13)..(13)
<223> OTHER INFORMATION: K or R
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(46)
<223> OTHER INFORMATION: alpha-CGRP 11-33

<400> SEQUENCE: 136

Ile Ser Ile Xaa Glu Ile Xaa Xaa Val Ile Val Xaa Xaa Ile Glu Thr
1               5                   10                  15

Ile Leu Phe Lys Lys Lys Lys Arg Leu Ala Gly Leu Leu Ser Arg Ser
            20                  25                  30

Gly Gly Val Val Lys Asn Asn Phe Val Pro Thr Asn Val Gly
        35                  40                  45

<210> SEQ ID NO 137
<211> LENGTH: 48
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
```

-continued

```
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(48)
<223> OTHER INFORMATION: alpha-CGRP 11-35

<400> SEQUENCE: 137

Ile Ser Ile Thr Glu Ile Lys Gly Val Ile Val His Arg Ile Glu Thr
1               5                   10                  15

Ile Leu Phe Lys Lys Lys Lys Arg Leu Ala Gly Leu Leu Ser Arg Ser
            20                  25                  30

Gly Gly Val Val Lys Asn Asn Phe Val Pro Thr Asn Val Gly Ser Lys
        35                  40                  45

<210> SEQ ID NO 138
<211> LENGTH: 48
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF 4 Th (UBITh3)
<220> FEATURE:
<221> NAME/KEY: SITE
<222> LOCATION: (4)..(4)
<223> OTHER INFORMATION: S or T
<220> FEATURE:
<221> NAME/KEY: SITE
<222> LOCATION: (7)..(7)
<223> OTHER INFORMATION: K or R
<220> FEATURE:
<221> NAME/KEY: SITE
<222> LOCATION: (8)..(8)
<223> OTHER INFORMATION: G or T
<220> FEATURE:
<221> NAME/KEY: SITE
<222> LOCATION: (12)..(12)
<223> OTHER INFORMATION: H or T
<220> FEATURE:
<221> NAME/KEY: SITE
<222> LOCATION: (13)..(13)
<223> OTHER INFORMATION: K or R
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(48)
<223> OTHER INFORMATION: alpha-CGRP 11-35

<400> SEQUENCE: 138

Ile Ser Ile Xaa Glu Ile Xaa Xaa Val Ile Val Xaa Xaa Ile Glu Thr
1               5                   10                  15

Ile Leu Phe Lys Lys Lys Lys Arg Leu Ala Gly Leu Leu Ser Arg Ser
            20                  25                  30

Gly Gly Val Val Lys Asn Asn Phe Val Pro Thr Asn Val Gly Ser Lys
        35                  40                  45

<210> SEQ ID NO 139
<211> LENGTH: 46
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(46)
<223> OTHER INFORMATION: alpha-CGRP 15-37

<400> SEQUENCE: 139

Ile Ser Ile Thr Glu Ile Lys Gly Val Ile Val His Arg Ile Glu Thr
1               5                   10                  15

Ile Leu Phe Lys Lys Lys Lys Leu Leu Ser Arg Ser Gly Gly Val Val
            20                  25                  30

Lys Asn Asn Phe Val Pro Thr Asn Val Gly Ser Lys Ala Phe
            35                  40                  45

<210> SEQ ID NO 140
<211> LENGTH: 46
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF 4 Th (UBITh3)
<220> FEATURE:
<221> NAME/KEY: SITE
<222> LOCATION: (4)..(4)
<223> OTHER INFORMATION: S or T
<220> FEATURE:
<221> NAME/KEY: SITE
<222> LOCATION: (7)..(7)
<223> OTHER INFORMATION: K or R
<220> FEATURE:
<221> NAME/KEY: SITE
<222> LOCATION: (8)..(8)
<223> OTHER INFORMATION: G or T
<220> FEATURE:
<221> NAME/KEY: SITE
<222> LOCATION: (12)..(12)
<223> OTHER INFORMATION: H or T
<220> FEATURE:
<221> NAME/KEY: SITE
<222> LOCATION: (13)..(13)
<223> OTHER INFORMATION: K or R
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(46)
<223> OTHER INFORMATION: alpha-CGRP 15-37

<400> SEQUENCE: 140

Ile Ser Ile Xaa Glu Ile Xaa Xaa Val Ile Val Xaa Xaa Ile Glu Thr
1               5                   10                  15

Ile Leu Phe Lys Lys Lys Lys Leu Leu Ser Arg Ser Gly Gly Val Val
```

-continued

```
              20              25              30

Lys Asn Asn Phe Val Pro Thr Asn Val Gly Ser Lys Ala Phe
        35              40              45
```

```
<210> SEQ ID NO 141
<211> LENGTH: 50
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF 4 Th (UBITh3)
<220> FEATURE:
<221> NAME/KEY: SITE
<222> LOCATION: (4)..(4)
<223> OTHER INFORMATION: S or T
<220> FEATURE:
<221> NAME/KEY: SITE
<222> LOCATION: (7)..(7)
<223> OTHER INFORMATION: K or R
<220> FEATURE:
<221> NAME/KEY: SITE
<222> LOCATION: (8)..(8)
<223> OTHER INFORMATION: G or T
<220> FEATURE:
<221> NAME/KEY: SITE
<222> LOCATION: (12)..(12)
<223> OTHER INFORMATION: H or T
<220> FEATURE:
<221> NAME/KEY: SITE
<222> LOCATION: (13)..(13)
<223> OTHER INFORMATION: K or R
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(50)
<223> OTHER INFORMATION: alpha-CGRP 11-37

<400> SEQUENCE: 141

Ile Ser Ile Xaa Glu Ile Xaa Xaa Val Ile Val Xaa Xaa Ile Glu Thr
1               5               10              15

Ile Leu Phe Lys Lys Lys Lys Arg Leu Ala Gly Leu Leu Ser Arg Ser
            20              25              30

Gly Gly Val Val Lys Asn Asn Phe Val Pro Thr Asn Val Gly Ser Lys
        35              40              45

Ala Phe
    50

<210> SEQ ID NO 142
<211> LENGTH: 41
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
```

-continued

```
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(41)
<223> OTHER INFORMATION: alpha-CGRP 20-37

<400> SEQUENCE: 142

Ile Ser Ile Thr Glu Ile Lys Gly Val Ile Val His Arg Ile Glu Thr
1               5                   10                  15

Ile Leu Phe Lys Lys Lys Lys Gly Gly Val Val Lys Asn Asn Phe Val
            20                  25                  30

Pro Thr Asn Val Gly Ser Lys Ala Phe
        35                  40

<210> SEQ ID NO 143
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(39)
<223> OTHER INFORMATION: alpha-CGRP 22-37

<400> SEQUENCE: 143

Ile Ser Ile Thr Glu Ile Lys Gly Val Ile Val His Arg Ile Glu Thr
1               5                   10                  15

Ile Leu Phe Lys Lys Lys Lys Val Val Lys Asn Asn Phe Val Pro Thr
            20                  25                  30

Asn Val Gly Ser Lys Ala Phe
        35

<210> SEQ ID NO 144
<211> LENGTH: 31
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(8)
<223> OTHER INFORMATION: alpha-CGRP 11-18
<220> FEATURE:
<221> NAME/KEY: SITE
<222> LOCATION: (9)..(9)
<223> OTHER INFORMATION: epsilon K
<220> FEATURE:
<221> NAME/KEY: PEPTIDE
<222> LOCATION: (9)..(12)
<223> OTHER INFORMATION: KKK-epsilon K as a spacer
<220> FEATURE:
<221> NAME/KEY: PEPTIDE
<222> LOCATION: (13)..(31)
<223> OTHER INFORMATION: MvF5 Th (UBITh1)

<400> SEQUENCE: 144
```

```
Arg Leu Ala Gly Leu Leu Ser Arg Lys Lys Lys Lys Ile Ser Ile Thr
1               5                   10                  15

Glu Ile Lys Gly Val Ile Val His Arg Ile Glu Thr Ile Leu Phe
            20                  25                  30

<210> SEQ ID NO 145
<211> LENGTH: 37
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(14)
<223> OTHER INFORMATION: alpha-CGRP 5-18
<220> FEATURE:
<221> NAME/KEY: SITE
<222> LOCATION: (15)..(15)
<223> OTHER INFORMATION: epsilon K
<220> FEATURE:
<221> NAME/KEY: PEPTIDE
<222> LOCATION: (15)..(18)
<223> OTHER INFORMATION: KKK-epsilon K as a spacer
<220> FEATURE:
<221> NAME/KEY: PEPTIDE
<222> LOCATION: (19)..(37)
<223> OTHER INFORMATION: MvF5 Th (UBITh1)

<400> SEQUENCE: 145

Ala Thr Cys Val Thr His Arg Leu Ala Gly Leu Leu Ser Arg Lys Lys
1               5                   10                  15

Lys Lys Ile Ser Ile Thr Glu Ile Lys Gly Val Ile Val His Arg Ile
            20                  25                  30

Glu Thr Ile Leu Phe
        35

<210> SEQ ID NO 146
<211> LENGTH: 36
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(13)
<223> OTHER INFORMATION: alpha-CGRP 4-16
<220> FEATURE:
<221> NAME/KEY: SITE
<222> LOCATION: (14)..(14)
<223> OTHER INFORMATION: epsilon K
<220> FEATURE:
<221> NAME/KEY: PEPTIDE
<222> LOCATION: (14)..(17)
<223> OTHER INFORMATION: KKK-epsilon K as a spacer
<220> FEATURE:
<221> NAME/KEY: PEPTIDE
<222> LOCATION: (18)..(36)
<223> OTHER INFORMATION: MvF5 Th (UBITh1)

<400> SEQUENCE: 146

Thr Ala Thr Cys Val Thr His Arg Leu Ala Gly Leu Leu Lys Lys Lys
1               5                   10                  15

Lys Ile Ser Ile Thr Glu Ile Lys Gly Val Ile Val His Arg Ile Glu
            20                  25                  30

Thr Ile Leu Phe
        35

<210> SEQ ID NO 147
```

-continued

```
<211> LENGTH: 33
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF 4 Th (UBITh3)
<220> FEATURE:
<221> NAME/KEY: SITE
<222> LOCATION: (4)..(4)
<223> OTHER INFORMATION: S or T
<220> FEATURE:
<221> NAME/KEY: SITE
<222> LOCATION: (7)..(7)
<223> OTHER INFORMATION: K or R
<220> FEATURE:
<221> NAME/KEY: SITE
<222> LOCATION: (8)..(8)
<223> OTHER INFORMATION: G or T
<220> FEATURE:
<221> NAME/KEY: SITE
<222> LOCATION: (12)..(12)
<223> OTHER INFORMATION: H or T
<220> FEATURE:
<221> NAME/KEY: SITE
<222> LOCATION: (13)..(13)
<223> OTHER INFORMATION: K or R
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(33)
<223> OTHER INFORMATION: alpha-CGRP 28-37

<400> SEQUENCE: 147

Ile Ser Ile Xaa Glu Ile Xaa Xaa Val Ile Val Xaa Xaa Ile Glu Thr
1               5                   10                  15

Ile Leu Phe Lys Lys Lys Lys Val Pro Thr Asn Val Gly Ser Lys Ala
            20                  25                  30

Phe

<210> SEQ ID NO 148
<211> LENGTH: 43
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(20)
<223> OTHER INFORMATION: alpha-CGRP 1-20
<220> FEATURE:
<221> NAME/KEY: PEPTIDE
<222> LOCATION: (21)..(24)
<223> OTHER INFORMATION: epsilon K-KKK as a spacer
<220> FEATURE:
<221> NAME/KEY: SITE
<222> LOCATION: (21)..(21)
<223> OTHER INFORMATION: epsilon-K
<220> FEATURE:
<221> NAME/KEY: PEPTIDE
<222> LOCATION: (25)..(43)
<223> OTHER INFORMATION: MvF4 Th (UBITh3)
<220> FEATURE:
<221> NAME/KEY: SITE
<222> LOCATION: (28)..(28)
<223> OTHER INFORMATION: S or T
```

```
<220> FEATURE:
<221> NAME/KEY: SITE
<222> LOCATION: (31)..(31)
<223> OTHER INFORMATION: K or R
<220> FEATURE:
<221> NAME/KEY: SITE
<222> LOCATION: (32)..(32)
<223> OTHER INFORMATION: G or T
<220> FEATURE:
<221> NAME/KEY: SITE
<222> LOCATION: (36)..(36)
<223> OTHER INFORMATION: H or T
<220> FEATURE:
<221> NAME/KEY: SITE
<222> LOCATION: (37)..(37)
<223> OTHER INFORMATION: K or R

<400> SEQUENCE: 148

Ala Cys Asp Thr Ala Thr Cys Val Thr His Arg Leu Ala Gly Leu Leu
1               5                   10                  15

Ser Arg Ser Gly Lys Lys Lys Lys Ile Ser Ile Xaa Glu Ile Xaa Xaa
            20                  25                  30

Val Ile Val Xaa Xaa Ile Glu Thr Ile Leu Phe
        35                  40

<210> SEQ ID NO 149
<211> LENGTH: 43
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF 4 Th (UBITh3)
<220> FEATURE:
<221> NAME/KEY: SITE
<222> LOCATION: (4)..(4)
<223> OTHER INFORMATION: S or T
<220> FEATURE:
<221> NAME/KEY: SITE
<222> LOCATION: (7)..(7)
<223> OTHER INFORMATION: K or R
<220> FEATURE:
<221> NAME/KEY: SITE
<222> LOCATION: (8)..(8)
<223> OTHER INFORMATION: G or T
<220> FEATURE:
<221> NAME/KEY: SITE
<222> LOCATION: (12)..(12)
<223> OTHER INFORMATION: H or T
<220> FEATURE:
<221> NAME/KEY: SITE
<222> LOCATION: (13)..(13)
<223> OTHER INFORMATION: K or R
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(43)
<223> OTHER INFORMATION: alpha-CGRP 1-20, cyclized

<400> SEQUENCE: 149

Ile Ser Ile Xaa Glu Ile Xaa Xaa Val Ile Val Xaa Xaa Ile Glu Thr
1               5                   10                  15

Ile Leu Phe Lys Lys Lys Lys Ala Cys Asp Thr Ala Thr Cys Val Thr
            20                  25                  30
```

```
His Arg Leu Ala Gly Leu Leu Ser Arg Ser Gly
        35                  40

<210> SEQ ID NO 150
<211> LENGTH: 50
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(50)
<223> OTHER INFORMATION: Rat alpha-CGRP 11-37

<400> SEQUENCE: 150

Ile Ser Ile Thr Glu Ile Lys Gly Val Ile Val His Arg Ile Glu Thr
1               5                   10                  15

Ile Leu Phe Lys Lys Lys Lys Arg Leu Ala Gly Leu Leu Ser Arg Ser
            20                  25                  30

Gly Gly Val Val Lys Asp Asn Phe Val Pro Thr Asn Val Gly Ser Glu
        35                  40                  45

Ala Phe
    50

<210> SEQ ID NO 151
<211> LENGTH: 50
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF 4 Th (UBITh3)
<220> FEATURE:
<221> NAME/KEY: SITE
<222> LOCATION: (4)..(4)
<223> OTHER INFORMATION: S or T
<220> FEATURE:
<221> NAME/KEY: SITE
<222> LOCATION: (7)..(7)
<223> OTHER INFORMATION: K or R
<220> FEATURE:
<221> NAME/KEY: SITE
<222> LOCATION: (8)..(8)
<223> OTHER INFORMATION: G or T
<220> FEATURE:
<221> NAME/KEY: SITE
<222> LOCATION: (12)..(12)
<223> OTHER INFORMATION: H or T
<220> FEATURE:
<221> NAME/KEY: SITE
<222> LOCATION: (13)..(13)
<223> OTHER INFORMATION: K or R
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
```

```
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(50)
<223> OTHER INFORMATION: Rat alpha-CGRP 11-37

<400> SEQUENCE: 151

Ile Ser Ile Xaa Glu Ile Xaa Xaa Val Ile Val Xaa Xaa Ile Glu Thr
1               5                   10                  15

Ile Leu Phe Lys Lys Lys Lys Arg Leu Ala Gly Leu Leu Ser Arg Ser
            20                  25                  30

Gly Gly Val Val Lys Asp Asn Phe Val Pro Thr Asn Val Gly Ser Glu
        35                  40                  45

Ala Phe
    50

<210> SEQ ID NO 152
<211> LENGTH: 36
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(17)
<223> OTHER INFORMATION: Clostridium tetani1 Th
<220> FEATURE:
<221> NAME/KEY: PEPTIDE
<222> LOCATION: (18)..(21)
<223> OTHER INFORMATION: epsilon K-KKK as a spacer
<220> FEATURE:
<221> NAME/KEY: SITE
<222> LOCATION: (18)..(18)
<223> OTHER INFORMATION: epsilon K
<220> FEATURE:
<221> NAME/KEY: PEPTIDE
<222> LOCATION: (22)..(36)
<223> OTHER INFORMATION: alpha-CGRP 11-25

<400> SEQUENCE: 152

Lys Lys Gln Tyr Ile Lys Ala Asn Ser Lys Phe Ile Gly Ile Thr Glu
1               5                   10                  15

Leu Lys Lys Lys Lys Arg Leu Ala Gly Leu Leu Ser Arg Ser Gly Gly
            20                  25                  30

Val Val Lys Asn
        35

<210> SEQ ID NO 153
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(15)
<223> OTHER INFORMATION: MvF1 Th
<220> FEATURE:
<221> NAME/KEY: PEPTIDE
<222> LOCATION: (16)..(19)
<223> OTHER INFORMATION: epsilon K-KKK as a spacer
<220> FEATURE:
<221> NAME/KEY: SITE
<222> LOCATION: (16)..(16)
<223> OTHER INFORMATION: epsilon K as a spacer
<220> FEATURE:
<221> NAME/KEY: PEPTIDE
<222> LOCATION: (20)..(34)
<223> OTHER INFORMATION: alpha-CGRP 11-25
```

<400> SEQUENCE: 153

Leu Ser Glu Ile Lys Gly Val Ile Val His Arg Leu Glu Gly Val Lys
1               5                   10                  15

Lys Lys Lys Arg Leu Ala Gly Leu Leu Ser Arg Ser Gly Gly Val Val
            20                  25                  30

Lys Asn

<210> SEQ ID NO 154
<211> LENGTH: 43
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(24)
<223> OTHER INFORMATION: Bordetella pertussis Th
<220> FEATURE:
<221> NAME/KEY: PEPTIDE
<222> LOCATION: (25)..(28)
<223> OTHER INFORMATION: Bordetella pertussis Th
<220> FEATURE:
<221> NAME/KEY: SITE
<222> LOCATION: (25)..(25)
<223> OTHER INFORMATION: epsilon K as a spacer
<220> FEATURE:
<221> NAME/KEY: PEPTIDE
<222> LOCATION: (29)..(43)
<223> OTHER INFORMATION: alpha-CGRP 11-25

<400> SEQUENCE: 154

Gly Ala Tyr Ala Arg Cys Pro Asn Gly Thr Arg Ala Leu Thr Val Ala
1               5                   10                  15

Glu Leu Arg Gly Asn Ala Glu Leu Lys Lys Lys Lys Arg Leu Ala Gly
            20                  25                  30

Leu Leu Ser Arg Ser Gly Gly Val Val Lys Asn
        35                  40

<210> SEQ ID NO 155
<211> LENGTH: 36
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(17)
<223> OTHER INFORMATION: Clostridium tetani2 Th
<220> FEATURE:
<221> NAME/KEY: PEPTIDE
<222> LOCATION: (18)..(21)
<223> OTHER INFORMATION: epsilon K-KKK as a spacer
<220> FEATURE:
<221> NAME/KEY: SITE
<222> LOCATION: (18)..(18)
<223> OTHER INFORMATION: epsilon K as a spacer
<220> FEATURE:
<221> NAME/KEY: PEPTIDE
<222> LOCATION: (22)..(36)
<223> OTHER INFORMATION: alpha-CGRP 11-25

<400> SEQUENCE: 155

Trp Val Arg Asp Ile Ile Asp Asp Phe Thr Asn Glu Ser Ser Gln Lys
1               5                   10                  15

Thr Lys Lys Lys Lys Arg Leu Ala Gly Leu Leu Ser Arg Ser Gly Gly
            20                  25                  30

Val Val Lys Asn

35

<210> SEQ ID NO 156
<211> LENGTH: 42
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(23)
<223> OTHER INFORMATION: Diphtheria Th
<220> FEATURE:
<221> NAME/KEY: PEPTIDE
<222> LOCATION: (24)..(27)
<223> OTHER INFORMATION: epsilon K-KKK as a spacer
<220> FEATURE:
<221> NAME/KEY: SITE
<222> LOCATION: (24)..(24)
<223> OTHER INFORMATION: epsilon K as a spacer
<220> FEATURE:
<221> NAME/KEY: PEPTIDE
<222> LOCATION: (28)..(42)
<223> OTHER INFORMATION: alpha-CGRP 11-25

<400> SEQUENCE: 156

Asp Ser Glu Thr Ala Asp Asn Leu Glu Lys Thr Val Ala Ala Leu Ser
1               5                   10                  15

Ile Leu Pro Gly His Gly Cys Lys Lys Lys Lys Arg Leu Ala Gly Leu
            20                  25                  30

Leu Ser Arg Ser Gly Gly Val Val Lys Asn
            35                  40

<210> SEQ ID NO 157
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(21)
<223> OTHER INFORMATION: Plasmodium falciparum Th
<220> FEATURE:
<221> NAME/KEY: PEPTIDE
<222> LOCATION: (22)..(25)
<223> OTHER INFORMATION: epsilon K-KKK as a spacer
<220> FEATURE:
<221> NAME/KEY: SITE
<222> LOCATION: (22)..(22)
<223> OTHER INFORMATION: epsilon K as a spacer
<220> FEATURE:
<221> NAME/KEY: PEPTIDE
<222> LOCATION: (26)..(40)
<223> OTHER INFORMATION: alpha-CGRP 11-25

<400> SEQUENCE: 157

Asp His Glu Lys Lys His Ala Lys Met Glu Lys Ala Ser Ser Val Phe
1               5                   10                  15

Asn Val Val Asn Ser Lys Lys Lys Arg Leu Ala Gly Leu Leu Ser
            20                  25                  30

Arg Ser Gly Gly Val Val Lys Asn
            35                  40

<210> SEQ ID NO 158
<211> LENGTH: 36
<212> TYPE: PRT
<213> ORGANISM: Artificial Sequence
<220> FEATURE:
<223> OTHER INFORMATION: Synthetic Peptide

```
<220> FEATURE:
<221> NAME/KEY: PEPTIDE
<222> LOCATION: (1)..(17)
<223> OTHER INFORMATION: Schistosoma mansoni Th
<220> FEATURE:
<221> NAME/KEY: PEPTIDE
<222> LOCATION: (18)..(21)
<223> OTHER INFORMATION: epsilon K-KKK as a spacer
<220> FEATURE:
<221> NAME/KEY: SITE
<222> LOCATION: (18)..(18)
<223> OTHER INFORMATION: epsilon K as a spacer
<220> FEATURE:
<221> NAME/KEY: PEPTIDE
<222> LOCATION: (22)..(36)
<223> OTHER INFORMATION: alpha-CGRP 11-25

<400> SEQUENCE: 158

Lys Trp Phe Lys Thr Asn Ala Pro Asn Gly Val Asp Glu Lys His Arg
1               5                   10                  15

His Lys Lys Lys Lys Arg Leu Ala Gly Leu Leu Ser Arg Ser Gly Gly
            20                  25                  30

Val Val Lys Asn
        35

<210> SEQ ID NO 159
<211> LENGTH: 44
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(25)
<223> OTHER INFORMATION: Cholera Toxin Th
<220> FEATURE:
<221> NAME/KEY: PEPTIDE
<222> LOCATION: (26)..(29)
<223> OTHER INFORMATION: epsilon K-KKK as a spacer
<220> FEATURE:
<221> NAME/KEY: SITE
<222> LOCATION: (26)..(26)
<223> OTHER INFORMATION: epsilon K as a spacer
<220> FEATURE:
<221> NAME/KEY: PEPTIDE
<222> LOCATION: (30)..(44)
<223> OTHER INFORMATION: alpha-CGRP 11-25

<400> SEQUENCE: 159

Ala Leu Asn Ile Trp Asp Arg Phe Asp Val Phe Cys Thr Leu Gly Ala
1               5                   10                  15

Thr Thr Gly Tyr Leu Lys Gly Asn Ser Lys Lys Lys Arg Leu Ala
            20                  25                  30

Gly Leu Leu Ser Arg Ser Gly Gly Val Val Lys Asn
        35                  40

<210> SEQ ID NO 160
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(15)
<223> OTHER INFORMATION: MvF2 Th
<220> FEATURE:
<221> NAME/KEY: PEPTIDE
<222> LOCATION: (16)..(19)
<223> OTHER INFORMATION: epsilon K-KKK as a spacer
<220> FEATURE:
```

```
<221> NAME/KEY: SITE
<222> LOCATION: (16)..(16)
<223> OTHER INFORMATION: epsilon K as a spacer
<220> FEATURE:
<221> NAME/KEY: PEPTIDE
<222> LOCATION: (20)..(34)
<223> OTHER INFORMATION: alpha-CGRP 11-25

<400> SEQUENCE: 160

Ile Ser Glu Ile Lys Gly Val Ile Val His Lys Ile Glu Gly Ile Lys
1               5                   10                  15

Lys Lys Lys Arg Leu Ala Gly Leu Leu Ser Arg Ser Gly Gly Val Val
            20                  25                  30

Lys Asn

<210> SEQ ID NO 161
<211> LENGTH: 41
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(22)
<223> OTHER INFORMATION: KKKMvF3 Th
<220> FEATURE:
<221> NAME/KEY: SITE
<222> LOCATION: (7)..(7)
<223> OTHER INFORMATION: S or T
<220> FEATURE:
<221> NAME/KEY: SITE
<222> LOCATION: (10)..(10)
<223> OTHER INFORMATION: K or R
<220> FEATURE:
<221> NAME/KEY: SITE
<222> LOCATION: (11)..(11)
<223> OTHER INFORMATION: G or T
<220> FEATURE:
<221> NAME/KEY: SITE
<222> LOCATION: (15)..(15)
<223> OTHER INFORMATION: H or T
<220> FEATURE:
<221> NAME/KEY: SITE
<222> LOCATION: (16)..(16)
<223> OTHER INFORMATION: K or R
<220> FEATURE:
<221> NAME/KEY: SITE
<222> LOCATION: (19)..(19)
<223> OTHER INFORMATION: G or T
<220> FEATURE:
<221> NAME/KEY: PEPTIDE
<222> LOCATION: (23)..(26)
<223> OTHER INFORMATION: epsilon K-KKK as a spacer
<220> FEATURE:
<221> NAME/KEY: SITE
<222> LOCATION: (23)..(23)
<223> OTHER INFORMATION: epsilon K as a spacer
<220> FEATURE:
<221> NAME/KEY: PEPTIDE
<222> LOCATION: (24)..(41)
<223> OTHER INFORMATION: alpha-CGRP 11-25

<400> SEQUENCE: 161

Lys Lys Lys Ile Ser Ile Xaa Glu Ile Xaa Xaa Val Ile Val Xaa Xaa
1               5                   10                  15

Ile Glu Xaa Ile Leu Phe Lys Lys Lys Arg Leu Ala Gly Leu Leu
            20                  25                  30

Ser Arg Ser Gly Gly Val Val Lys Asn
        35                  40

<210> SEQ ID NO 162
```

```
<211> LENGTH: 37
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(18)
<223> OTHER INFORMATION: HBsAg 1 Th
<220> FEATURE:
<221> NAME/KEY: SITE
<222> LOCATION: (1)..(1)
<223> OTHER INFORMATION: K or R
<220> FEATURE:
<221> NAME/KEY: SITE
<222> LOCATION: (2)..(2)
<223> OTHER INFORMATION: K or R
<220> FEATURE:
<221> NAME/KEY: SITE
<222> LOCATION: (3)..(3)
<223> OTHER INFORMATION: K or R
<220> FEATURE:
<221> NAME/KEY: SITE
<222> LOCATION: (4)..(4)
<223> OTHER INFORMATION: L or I or V or F
<220> FEATURE:
<221> NAME/KEY: SITE
<222> LOCATION: (5)..(5)
<223> OTHER INFORMATION: F or K or R
<220> FEATURE:
<221> NAME/KEY: SITE
<222> LOCATION: (6)..(6)
<223> OTHER INFORMATION: L or I or V or F
<220> FEATURE:
<221> NAME/KEY: SITE
<222> LOCATION: (7)..(7)
<223> OTHER INFORMATION: L or I or V or F
<220> FEATURE:
<221> NAME/KEY: SITE
<222> LOCATION: (9)..(9)
<223> OTHER INFORMATION: K or R
<220> FEATURE:
<221> NAME/KEY: SITE
<222> LOCATION: (10)..(10)
<223> OTHER INFORMATION: L or I or V or F
<220> FEATURE:
<221> NAME/KEY: SITE
<222> LOCATION: (11)..(11)
<223> OTHER INFORMATION: L or I or V or F
<220> FEATURE:
<221> NAME/KEY: SITE
<222> LOCATION: (13)..(13)
<223> OTHER INFORMATION: L or I or V or F
<220> FEATURE:
<221> NAME/KEY: SITE
<222> LOCATION: (15)..(15)
<223> OTHER INFORMATION: Q or L or I or V or F
<220> FEATURE:
<221> NAME/KEY: SITE
<222> LOCATION: (17)..(17)
<223> OTHER INFORMATION: L or I or V or F
<220> FEATURE:
<221> NAME/KEY: SITE
<222> LOCATION: (18)..(18)
<223> OTHER INFORMATION: D or R
<220> FEATURE:
<221> NAME/KEY: PEPTIDE
<222> LOCATION: (19)..(22)
<223> OTHER INFORMATION: epsilon K-KKK as a spacer
<220> FEATURE:
<221> NAME/KEY: SITE
<222> LOCATION: (19)..(19)
<223> OTHER INFORMATION: epsilon K as a spacer
<220> FEATURE:
<221> NAME/KEY: PEPTIDE
<222> LOCATION: (23)..(37)
<223> OTHER INFORMATION: alpha-CGRP 11-25

<400> SEQUENCE: 162
```

```
Xaa Xaa Xaa Xaa Xaa Xaa Xaa Thr Xaa Xaa Xaa Thr Xaa Pro Xaa Ser
1               5                   10                  15

Xaa Xaa Lys Lys Lys Lys Arg Leu Ala Gly Leu Leu Ser Arg Ser Gly
            20                  25                  30

Gly Val Val Lys Asn
        35
```

```
<210> SEQ ID NO 163
<211> LENGTH: 37
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(18)
<223> OTHER INFORMATION: HBsAg 2 Th
<220> FEATURE:
<221> NAME/KEY: SITE
<222> LOCATION: (4)..(4)
<223> OTHER INFORMATION: I or F
<220> FEATURE:
<221> NAME/KEY: SITE
<222> LOCATION: (5)..(5)
<223> OTHER INFORMATION: I or F
<220> FEATURE:
<221> NAME/KEY: SITE
<222> LOCATION: (6)..(6)
<223> OTHER INFORMATION: T or L
<220> FEATURE:
<221> NAME/KEY: SITE
<222> LOCATION: (7)..(7)
<223> OTHER INFORMATION: I or L
<220> FEATURE:
<221> NAME/KEY: SITE
<222> LOCATION: (11)..(11)
<223> OTHER INFORMATION: I or L
<220> FEATURE:
<221> NAME/KEY: SITE
<222> LOCATION: (14)..(14)
<223> OTHER INFORMATION: P or I
<220> FEATURE:
<221> NAME/KEY: SITE
<222> LOCATION: (15)..(15)
<223> OTHER INFORMATION: Q or T
<220> FEATURE:
<221> NAME/KEY: SITE
<222> LOCATION: (16)..(16)
<223> OTHER INFORMATION: S or T
<220> FEATURE:
<221> NAME/KEY: SITE
<222> LOCATION: (17)..(17)
<223> OTHER INFORMATION: L or I
<220> FEATURE:
<221> NAME/KEY: PEPTIDE
<222> LOCATION: (19)..(22)
<223> OTHER INFORMATION: epsilon K-KKK as a spacer
<220> FEATURE:
<221> NAME/KEY: SITE
<222> LOCATION: (19)..(19)
<223> OTHER INFORMATION: epsilon K as a spacer
<220> FEATURE:
<221> NAME/KEY: PEPTIDE
<222> LOCATION: (23)..(37)
<223> OTHER INFORMATION: alpha-CGRP 11-25

<400> SEQUENCE: 163

Lys Lys Lys Xaa Xaa Xaa Xaa Thr Arg Ile Xaa Thr Ile Xaa Xaa Xaa
1               5                   10                  15

Xaa Asp Lys Lys Lys Lys Arg Leu Ala Gly Leu Leu Ser Arg Ser Gly
            20                  25                  30

Gly Val Val Lys Asn
```

-continued

35

```
<210> SEQ ID NO 164
<211> LENGTH: 37
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(18)
<223> OTHER INFORMATION: HBsAg3 Th
<220> FEATURE:
<221> NAME/KEY: PEPTIDE
<222> LOCATION: (19)..(22)
<223> OTHER INFORMATION: epsilon K-KKK as a spacer
<220> FEATURE:
<221> NAME/KEY: SITE
<222> LOCATION: (19)..(19)
<223> OTHER INFORMATION: epsilon K
<220> FEATURE:
<221> NAME/KEY: PEPTIDE
<222> LOCATION: (23)..(37)
<223> OTHER INFORMATION: alpha-CGRP 11-25

<400> SEQUENCE: 164

Lys Lys Lys Ile Ile Thr Ile Thr Arg Ile Ile Thr Ile Ile Thr Thr
1               5                   10                  15

Ile Asp Lys Lys Lys Lys Arg Leu Ala Gly Leu Leu Ser Arg Ser Gly
            20                  25                  30

Gly Val Val Lys Asn
            35

<210> SEQ ID NO 165
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(11)
<223> OTHER INFORMATION: Influenza MP1_1 Th
<220> FEATURE:
<221> NAME/KEY: PEPTIDE
<222> LOCATION: (12)..(15)
<223> OTHER INFORMATION: epsilon K-KKK as a spacer
<220> FEATURE:
<221> NAME/KEY: SITE
<222> LOCATION: (12)..(12)
<223> OTHER INFORMATION: epsilon K as a spacer
<220> FEATURE:
<221> NAME/KEY: PEPTIDE
<222> LOCATION: (16)..(30)
<223> OTHER INFORMATION: alpha-CGRP 11-25

<400> SEQUENCE: 165

Phe Val Phe Thr Leu Thr Val Pro Ser Glu Arg Lys Lys Lys Lys Arg
1               5                   10                  15

Leu Ala Gly Leu Leu Ser Arg Ser Gly Gly Val Val Lys Asn
            20                  25                  30

<210> SEQ ID NO 166
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(15)
```

-continued

```
<223> OTHER INFORMATION: Influenza MP1_2 Th
<220> FEATURE:
<221> NAME/KEY: PEPTIDE
<222> LOCATION: (16)..(19)
<223> OTHER INFORMATION: epsilon K-KKK as a spacer
<220> FEATURE:
<221> NAME/KEY: SITE
<222> LOCATION: (16)..(16)
<223> OTHER INFORMATION: epsilon K as a spacer
<220> FEATURE:
<221> NAME/KEY: PEPTIDE
<222> LOCATION: (20)..(34)
<223> OTHER INFORMATION: alpha-CGRP 11-25

<400> SEQUENCE: 166

Ser Gly Pro Leu Lys Ala Glu Ile Ala Gln Arg Leu Glu Asp Val Lys
1               5                   10                  15

Lys Lys Lys Arg Leu Ala Gly Leu Leu Ser Arg Ser Gly Gly Val Val
            20                  25                  30

Lys Asn

<210> SEQ ID NO 167
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(9)
<223> OTHER INFORMATION: Influenza NSP1 Th
<220> FEATURE:
<221> NAME/KEY: PEPTIDE
<222> LOCATION: (10)..(13)
<223> OTHER INFORMATION: epsilon K-KKK as a spacer
<220> FEATURE:
<221> NAME/KEY: SITE
<222> LOCATION: (10)..(10)
<223> OTHER INFORMATION: epsilon K as a spacer
<220> FEATURE:
<221> NAME/KEY: PEPTIDE
<222> LOCATION: (14)..(28)
<223> OTHER INFORMATION: alpha-CGRP 11-25

<400> SEQUENCE: 167

Asp Arg Leu Arg Arg Asp Gln Lys Ser Lys Lys Lys Arg Leu Ala
1               5                   10                  15

Gly Leu Leu Ser Arg Ser Gly Gly Val Val Lys Asn
            20                  25

<210> SEQ ID NO 168
<211> LENGTH: 38
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: EBV BHRF1 Th
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: SITE
<222> LOCATION: (20)..(20)
<223> OTHER INFORMATION: epsilon K
<220> FEATURE:
<221> NAME/KEY: PEPTIDE
<222> LOCATION: (24)..(38)
<223> OTHER INFORMATION: alpha-CGRP 11-25
```

-continued

<400> SEQUENCE: 168

Ala Gly Leu Thr Leu Ser Leu Leu Val Ile Cys Ser Tyr Leu Phe Ile
1               5                   10                  15

Ser Arg Gly Lys Lys Lys Lys Arg Leu Ala Gly Leu Leu Ser Arg Ser
            20                  25                  30

Gly Gly Val Val Lys Asn
        35

<210> SEQ ID NO 169
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(15)
<223> OTHER INFORMATION: Clostridium tetani TT1 Th
<220> FEATURE:
<221> NAME/KEY: PEPTIDE
<222> LOCATION: (16)..(19)
<223> OTHER INFORMATION: epsilon K-KKK as a spacer
<220> FEATURE:
<221> NAME/KEY: SITE
<222> LOCATION: (16)..(16)
<223> OTHER INFORMATION: epsilon K as a spacer
<220> FEATURE:
<221> NAME/KEY: PEPTIDE
<222> LOCATION: (20)..(34)
<223> OTHER INFORMATION: alpha-CGRP 11-37

<400> SEQUENCE: 169

Gln Tyr Ile Lys Ala Asn Ser Lys Phe Ile Gly Ile Thr Glu Leu Lys
1               5                   10                  15

Lys Lys Lys Arg Leu Ala Gly Leu Leu Ser Arg Ser Gly Gly Val Val
            20                  25                  30

Lys Asn

<210> SEQ ID NO 170
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(20)
<223> OTHER INFORMATION: EBV EBNA-1 Th
<220> FEATURE:
<221> NAME/KEY: PEPTIDE
<222> LOCATION: (21)..(24)
<223> OTHER INFORMATION: epsilon K-KKK as a spacer
<220> FEATURE:
<221> NAME/KEY: SITE
<222> LOCATION: (21)..(21)
<223> OTHER INFORMATION: epsilon K as a spacer
<220> FEATURE:
<221> NAME/KEY: PEPTIDE
<222> LOCATION: (25)..(39)
<223> OTHER INFORMATION: alpha-CGRP 11-25

<400> SEQUENCE: 170

Pro Gly Pro Leu Arg Glu Ser Ile Val Cys Tyr Phe Met Val Phe Leu
1               5                   10                  15

Gln Thr His Ile Lys Lys Lys Lys Arg Leu Ala Gly Leu Leu Ser Arg
            20                  25                  30

Ser Gly Gly Val Val Lys Asn

-continued

35

<210> SEQ ID NO 171
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(21)
<223> OTHER INFORMATION: Clostridium tetani  TT2 Th
<220> FEATURE:
<221> NAME/KEY: PEPTIDE
<222> LOCATION: (22)..(25)
<223> OTHER INFORMATION: epsilon K-KKK as a spacer
<220> FEATURE:
<221> NAME/KEY: SITE
<222> LOCATION: (22)..(22)
<223> OTHER INFORMATION: epsilon K as a spacer
<220> FEATURE:
<221> NAME/KEY: PEPTIDE
<222> LOCATION: (26)..(40)
<223> OTHER INFORMATION: alpha-CGRP 11-25

<400> SEQUENCE: 171

Phe Asn Asn Phe Thr Val Ser Phe Trp Leu Arg Val Pro Lys Val Ser
1               5                   10                  15

Ala Ser His Leu Glu Lys Lys Lys Lys Arg Leu Ala Gly Leu Leu Ser
            20                  25                  30

Arg Ser Gly Gly Val Val Lys Asn
        35                  40

<210> SEQ ID NO 172
<211> LENGTH: 35
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(16)
<223> OTHER INFORMATION: Clostridium tetani TT3 Th
<220> FEATURE:
<221> NAME/KEY: PEPTIDE
<222> LOCATION: (17)..(20)
<223> OTHER INFORMATION: epsilon K-KKK as a spacer
<220> FEATURE:
<221> NAME/KEY: SITE
<222> LOCATION: (17)..(17)
<223> OTHER INFORMATION: epsilon K as a spacer
<220> FEATURE:
<221> NAME/KEY: PEPTIDE
<222> LOCATION: (21)..(35)
<223> OTHER INFORMATION: alpha-CGRP 11-25

<400> SEQUENCE: 172

Lys Phe Ile Ile Lys Arg Tyr Thr Pro Asn Asn Glu Ile Asp Ser Phe
1               5                   10                  15

Lys Lys Lys Lys Arg Leu Ala Gly Leu Leu Ser Arg Ser Gly Gly Val
            20                  25                  30

Val Lys Asn
        35

<210> SEQ ID NO 173
<211> LENGTH: 35
<212> TYPE: PRT
<213> ORGANISM: Artificial Sequence
<220> FEATURE:
<223> OTHER INFORMATION: Synthetic Peptide

```
<220> FEATURE:
<221> NAME/KEY: PEPTIDE
<222> LOCATION: (1)..(16)
<223> OTHER INFORMATION: Clostridium tetani  TT4 Th
<220> FEATURE:
<221> NAME/KEY: PEPTIDE
<222> LOCATION: (17)..(20)
<223> OTHER INFORMATION: epsilon K-KKK as a spacer
<220> FEATURE:
<221> NAME/KEY: SITE
<222> LOCATION: (17)..(17)
<223> OTHER INFORMATION: epsilon K as a spacer
<220> FEATURE:
<221> NAME/KEY: PEPTIDE
<222> LOCATION: (21)..(35)
<223> OTHER INFORMATION: alpha-CGRP 11-25

<400> SEQUENCE: 173

Val Ser Ile Asp Lys Phe Arg Ile Phe Cys Lys Ala Leu Asn Pro Lys
1               5                   10                  15

Lys Lys Lys Lys Arg Leu Ala Gly Leu Leu Ser Arg Ser Gly Gly Val
            20                  25                  30

Val Lys Asn
        35

<210> SEQ ID NO 174
<211> LENGTH: 37
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(18)
<223> OTHER INFORMATION: EBV CP Th
<220> FEATURE:
<221> NAME/KEY: PEPTIDE
<222> LOCATION: (19)..(22)
<223> OTHER INFORMATION: epsilon K-KKK as a spacer
<220> FEATURE:
<221> NAME/KEY: SITE
<222> LOCATION: (19)..(19)
<223> OTHER INFORMATION: epsilon K as a spacer
<220> FEATURE:
<221> NAME/KEY: PEPTIDE
<222> LOCATION: (23)..(37)
<223> OTHER INFORMATION: alpha-CGRP 11-25

<400> SEQUENCE: 174

Val Pro Gly Leu Tyr Ser Pro Cys Arg Ala Phe Phe Asn Lys Glu Glu
1               5                   10                  15

Leu Leu Lys Lys Lys Lys Arg Leu Ala Gly Leu Leu Ser Arg Ser Gly
            20                  25                  30

Gly Val Val Lys Asn
        35

<210> SEQ ID NO 175
<211> LENGTH: 33
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(14)
<223> OTHER INFORMATION: HCMV IE1 Th
<220> FEATURE:
<221> NAME/KEY: PEPTIDE
<222> LOCATION: (15)..(18)
<223> OTHER INFORMATION: epsilon K-KKK as a spacer
<220> FEATURE:
```

-continued

```
<221> NAME/KEY: SITE
<222> LOCATION: (15)..(15)
<223> OTHER INFORMATION: epsilon K as a spacer
<220> FEATURE:
<221> NAME/KEY: PEPTIDE
<222> LOCATION: (19)..(33)
<223> OTHER INFORMATION: alpha-CGRP 11-25

<400> SEQUENCE: 175

Asp Lys Arg Glu Met Trp Met Ala Cys Ile Lys Glu Leu His Lys Lys
1               5                   10                  15

Lys Lys Arg Leu Ala Gly Leu Leu Ser Arg Ser Gly Gly Val Val Lys
            20                  25                  30

Asn

<210> SEQ ID NO 176
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(15)
<223> OTHER INFORMATION: EBV GP340 Th
<220> FEATURE:
<221> NAME/KEY: PEPTIDE
<222> LOCATION: (16)..(19)
<223> OTHER INFORMATION: epsilon K-KKK as a spacer
<220> FEATURE:
<221> NAME/KEY: SITE
<222> LOCATION: (16)..(16)
<223> OTHER INFORMATION: epsilon K as a spacer
<220> FEATURE:
<221> NAME/KEY: PEPTIDE
<222> LOCATION: (20)..(34)
<223> OTHER INFORMATION: alpha-CGRP 11-25

<400> SEQUENCE: 176

Thr Gly His Gly Ala Arg Thr Ser Thr Glu Pro Thr Thr Asp Tyr Lys
1               5                   10                  15

Lys Lys Lys Arg Leu Ala Gly Leu Leu Ser Arg Ser Gly Gly Val Val
            20                  25                  30

Lys Asn

<210> SEQ ID NO 177
<211> LENGTH: 32
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(13)
<223> OTHER INFORMATION: EBV BPLF1 Th
<220> FEATURE:
<221> NAME/KEY: PEPTIDE
<222> LOCATION: (14)..(17)
<223> OTHER INFORMATION: epsilon K-KKK as a spacer
<220> FEATURE:
<221> NAME/KEY: SITE
<222> LOCATION: (14)..(14)
<223> OTHER INFORMATION: epsilon K as a spacer
<220> FEATURE:
<221> NAME/KEY: PEPTIDE
<222> LOCATION: (18)..(32)
<223> OTHER INFORMATION: alpha-CGRP 11-25

<400> SEQUENCE: 177

Lys Glu Leu Lys Arg Gln Tyr Glu Lys Lys Leu Arg Gln Lys Lys Lys
```

```
1                5               10              15

Lys Arg Leu Ala Gly Leu Leu Ser Arg Ser Gly Gly Val Val Lys Asn
         20              25              30
```

<210> SEQ ID NO 178
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(11)
<223> OTHER INFORMATION: EBV EBNA-2 Th
<220> FEATURE:
<221> NAME/KEY: PEPTIDE
<222> LOCATION: (12)..(15)
<223> OTHER INFORMATION: epsilon K-KKK as a spacer
<220> FEATURE:
<221> NAME/KEY: SITE
<222> LOCATION: (12)..(12)
<223> OTHER INFORMATION: epsilon K as a spacer
<220> FEATURE:
<221> NAME/KEY: PEPTIDE
<222> LOCATION: (16)..(30)
<223> OTHER INFORMATION: alpha-CGRP 11-25

<400> SEQUENCE: 178

```
Thr Val Phe Tyr Asn Ile Pro Pro Met Pro Leu Lys Lys Lys Lys Arg
1                5               10              15

Leu Ala Gly Leu Leu Ser Arg Ser Gly Gly Val Val Lys Asn
         20              25              30
```

<210> SEQ ID NO 179
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(15)
<223> OTHER INFORMATION: HBsAg4 Th
<220> FEATURE:
<221> NAME/KEY: PEPTIDE
<222> LOCATION: (16)..(19)
<223> OTHER INFORMATION: epsilon K-KKK as a spacer
<220> FEATURE:
<221> NAME/KEY: SITE
<222> LOCATION: (16)..(16)
<223> OTHER INFORMATION: epsilon K as a spacer
<220> FEATURE:
<221> NAME/KEY: PEPTIDE
<222> LOCATION: (20)..(34)
<223> OTHER INFORMATION: alpha-CGRP 11-25

<400> SEQUENCE: 179

```
Phe Phe Leu Leu Thr Arg Ile Leu Thr Ile Pro Gln Ser Leu Asp Lys
1                5               10              15

Lys Lys Lys Arg Leu Ala Gly Leu Leu Ser Arg Ser Gly Gly Val Val
         20              25              30

Lys Asn
```

<210> SEQ ID NO 180
<211> LENGTH: 35
<212> TYPE: PRT
<213> ORGANISM: Artificial Sequence
<220> FEATURE:
<223> OTHER INFORMATION: Synthetic Peptide
<220> FEATURE:

-continued

```
<221> NAME/KEY: PEPTIDE
<222> LOCATION: (1)..(16)
<223> OTHER INFORMATION: Yersinia Invasin Th
<220> FEATURE:
<221> NAME/KEY: PEPTIDE
<222> LOCATION: (17)..(20)
<223> OTHER INFORMATION: epsilon K-KKK as a spacer
<220> FEATURE:
<221> NAME/KEY: SITE
<222> LOCATION: (17)..(17)
<223> OTHER INFORMATION: epsilon K as a spacer
<220> FEATURE:
<221> NAME/KEY: PEPTIDE
<222> LOCATION: (21)..(35)
<223> OTHER INFORMATION: alpha-CGRP 11-25

<400> SEQUENCE: 180

Thr Ala Lys Ser Lys Lys Phe Pro Ser Tyr Thr Ala Thr Tyr Gln Phe
1               5                   10                  15

Lys Lys Lys Lys Arg Leu Ala Gly Leu Leu Ser Arg Ser Gly Gly Val
            20                  25                  30

Val Lys Asn
        35

<210> SEQ ID NO 181
<211> LENGTH: 55
<212> TYPE: PRT
<213> ORGANISM: Homo sapiens
<220> FEATURE:
<221> NAME/KEY: PEPTIDE
<222> LOCATION: (1)..(55)
<223> OTHER INFORMATION: alpha-CGRP (-9 to 46)

<400> SEQUENCE: 181

Gly Ser Arg Ile Ile Ala Gln Lys Arg Ala Cys Asp Thr Ala Thr Cys
1               5                   10                  15

Val Thr His Arg Leu Ala Gly Leu Leu Ser Arg Ser Gly Gly Val Val
            20                  25                  30

Lys Asn Asn Phe Val Pro Thr Asn Val Gly Ser Lys Ala Phe Gly Arg
        35                  40                  45

Arg Arg Arg Asp Leu Gln Ala
    50                  55

<210> SEQ ID NO 182
<211> LENGTH: 37
<212> TYPE: PRT
<213> ORGANISM: Equus caballus

<400> SEQUENCE: 182

Ser Cys Asn Thr Ala Thr Cys Val Thr His Arg Leu Ala Gly Leu Leu
1               5                   10                  15

Ser Arg Ser Gly Gly Val Val Lys Ser Asn Phe Val Pro Thr Asp Val
            20                  25                  30

Gly Ser Glu Ala Phe
        35

<210> SEQ ID NO 183
<211> LENGTH: 37
<212> TYPE: PRT
<213> ORGANISM: Gallus gallus

<400> SEQUENCE: 183

Ala Cys Asn Thr Ala Thr Cys Val Thr His Arg Leu Ala Asp Phe Leu
1               5                   10                  15
```

-continued

```
Ser Arg Ser Gly Gly Val Gly Lys Asn Asn Phe Val Pro Thr Asn Val
            20                  25                  30

Gly Ser Lys Ala Phe
        35

<210> SEQ ID NO 184
<211> LENGTH: 37
<212> TYPE: PRT
<213> ORGANISM: Sus scrofa

<400> SEQUENCE: 184

Ser Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asp Val
            20                  25                  30

Gly Ser Glu Ala Phe
        35

<210> SEQ ID NO 185
<211> LENGTH: 37
<212> TYPE: PRT
<213> ORGANISM: Ovis aries

<400> SEQUENCE: 185

Ser Cys Asn Thr Ala Thr Cys Val Thr His Arg Leu Ala Gly Leu Leu
1               5                   10                  15

Ser Arg Ser Gly Gly Val Val Lys Ser Asn Phe Val Pro Thr Asn Val
            20                  25                  30

Gly Ser Gln Ala Phe
        35

<210> SEQ ID NO 186
<211> LENGTH: 37
<212> TYPE: PRT
<213> ORGANISM: Bos taurus

<400> SEQUENCE: 186

Ser Cys Asn Thr Ala Thr Cys Val Thr His Arg Leu Ala Gly Leu Leu
1               5                   10                  15

Ser Arg Ser Gly Gly Val Val Lys Ser Asn Phe Val Pro Thr Asn Val
            20                  25                  30

Gly Ser Glu Ala Phe
        35

<210> SEQ ID NO 187
<211> LENGTH: 37
<212> TYPE: PRT
<213> ORGANISM: Canis lupus

<400> SEQUENCE: 187

Ser Cys Asn Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Glu Ala Phe
        35

<210> SEQ ID NO 188
<211> LENGTH: 37
<212> TYPE: PRT
<213> ORGANISM: Monodelphis domestica
```

```
<400> SEQUENCE: 188

Gly Cys Asn Thr Ala Thr Cys Val Thr His Arg Leu Ala Asp Phe Leu
1               5                   10                  15

Ser Arg Ser Gly Gly Val Ala Lys Ser Asp Phe Val Pro Thr Asn Val
            20                  25                  30

Gly Ala Lys Ala Phe
        35

<210> SEQ ID NO 189
<211> LENGTH: 37
<212> TYPE: PRT
<213> ORGANISM: Gekko gecko

<400> SEQUENCE: 189

Ala Cys Asn Thr Ala Thr Cys Val Thr His Arg Leu Ala Asp Phe Leu
1               5                   10                  15

Ser Arg Ser Gly Gly Val Gly Lys Ser Asn Phe Val Pro Thr Asn Val
            20                  25                  30

Gly Ala Lys Ala Phe
        35

<210> SEQ ID NO 190
<211> LENGTH: 37
<212> TYPE: PRT
<213> ORGANISM: Phyllomedusa bicolor

<400> SEQUENCE: 190

Ser Cys Asp Thr Ser Thr Cys Ala Thr Gln Arg Leu Ala Asp Phe Leu
1               5                   10                  15

Ser Arg Ser Gly Gly Ile Gly Ser Pro Asp Phe Val Pro Thr Asp Val
            20                  25                  30

Ser Ala Asn Ser Phe
        35

<210> SEQ ID NO 191
<211> LENGTH: 37
<212> TYPE: PRT
<213> ORGANISM: Artificial Sequence
<220> FEATURE:
<223> OTHER INFORMATION: Takifugu rubripes

<400> SEQUENCE: 191

Ala Cys Asn Thr Ala Thr Cys Val Thr His Arg Leu Ala Asp Phe Leu
1               5                   10                  15

Ser Arg Ser Gly Gly Met Gly Asn Ser Asn Phe Val Pro Thr Asn Val
            20                  25                  30

Gly Ala Lys Ala Phe
        35

<210> SEQ ID NO 192
<211> LENGTH: 37
<212> TYPE: PRT
<213> ORGANISM: Paralichthys olivaceus

<400> SEQUENCE: 192

Gly Cys Asn Thr Ser Thr Cys Val Thr His Arg Leu Ala Asp Leu Leu
1               5                   10                  15

Ser Arg Ser Gly Gly Leu Gly Tyr Asn Asn Phe Val Pro Thr Asn Val
            20                  25                  30
```

-continued

Gly Ala Gln Ala Phe
        35

<210> SEQ ID NO 193
<211> LENGTH: 37
<212> TYPE: PRT
<213> ORGANISM: Carassius auratus

<400> SEQUENCE: 193

Ala Cys Asn Thr Ala Thr Cys Val Thr His Arg Leu Ala Asp Phe Leu
1               5                   10                  15

Ser Arg Ser Gly Gly Ile Gly Ser Ser Lys Phe Val Pro Thr Asn Val
            20                  25                  30

Gly Ser Gln Ala Phe
        35

<210> SEQ ID NO 194
<211> LENGTH: 37
<212> TYPE: PRT
<213> ORGANISM: Salmo salar

<400> SEQUENCE: 194

Ala Cys Asn Thr Ala Thr Cys Val Thr His Arg Leu Ala Asp Phe Leu
1               5                   10                  15

Ser Arg Ser Gly Gly Met Gly Asn Ser Asn Phe Val Pro Thr Asn Val
            20                  25                  30

Gly Ser Lys Ala Phe
        35

<210> SEQ ID NO 195
<211> LENGTH: 37
<212> TYPE: PRT
<213> ORGANISM: Oryzias latipes

<400> SEQUENCE: 195

Ala Cys Asn Thr Ala Thr Cys Val Thr His Arg Leu Ala Asp Phe Leu
1               5                   10                  15

Ser Arg Ser Gly Gly Leu Gly His Ser Asn Phe Val Pro Thr Asn Val
            20                  25                  30

Gly Ala Gln Ala Phe
        35

<210> SEQ ID NO 196
<211> LENGTH: 37
<212> TYPE: PRT
<213> ORGANISM: Danio rerio

<400> SEQUENCE: 196

Ala Cys Asn Thr Ala Thr Cys Val Thr His Arg Leu Ala Asp Phe Leu
1               5                   10                  15

Ser Arg Ser Gly Gly Ile Gly Ser Ser Asp Phe Val Pro Thr Asn Val
            20                  25                  30

Gly Ser Gln Ala Phe
        35

PEPTIDE IMMUNOGENS TARGETING CALCITONIN GENE-RELATED PEPTIDE (CGRP) AND FORMULATIONS THEREOF FOR PREVENTION AND TREATMENT OF MIGRAINE

This application is a national phase entry under 35 U.S.C. § 371 of International Application Number PCT/US2019/069117, filed Dec. 31, 2019, entitled "PEPTIDE IMMUNOGENS TARGETING CALCITONIN GENE-RELATED PEPTIDE (CGRP) AND FORMULATIONS THEREOF FOR PREVENTION AND TREATMENT OF MIGRAINE", which claims the benefit of U.S. Provisional Application Ser. No. 62/787,102, filed Dec. 31, 2018, the entire contents of these prior applications are hereby incorporated by reference in their entireties as if fully set forth herein.

FIELD OF THE INVENTION

This disclosure relates to peptide immunogen constructs targeting Calcitonin Gene-Related Peptide (CGRP) and formulations thereof for prevention and treatment of migraine.

BACKGROUND OF THE INVENTION

Migraine is a common medical condition that affects as many as 37 million people in the US. It is considered a systemic illness, not just a headache. Recent research has demonstrated that changes may begin to occur in the brain as early as 24 hours before migraine symptoms begin. Migraine symptoms vary depending on the affected individual, but can include a severe throbbing headache, often on only one side of the head, nausea, vomiting, light sensitivity (photophobic), sound sensitivity (phonophobic), or combinations of these symptoms. These symptoms can persist even after the headache pain goes away.

There are a variety of migraine subtypes with symptoms that include weakness, numbness, visual changes or loss, vertigo, and difficulty speaking (some patients may appear as if they are having a stroke). The disability resulting from this chronic condition is tremendous, causing missed days of work and loss of ability to join family activities.

It is sometimes possible for people to use an "abortive" medication, which, when taken early, can arrest the migraine process. For many patients, a preventive medication can decrease both the frequency and the severity of the migraines. However, many of the medications that are used to prevent or treat migraines were developed primarily for other conditions: seizures, depression, high blood pressure, and muscle spasms, for example.

Researchers have been working for decades to develop a "targeted" preventive therapy specifically for migraine. Calcitonin gene-related peptide (CGRP) is a molecule that is synthesized in both peripheral and central neurons. It has been implicated in different pain processes, including migraine, and functions as a vasodilator. Abortive treatments for migraines focus on stopping CGRP from being activated at the start of a migraine. Small-molecule CGRP antagonist drugs have been shown to decrease migraine pain based on certain measures, but these antagonists can have serious side effects including liver toxicity.

Monoclonal antibodies that target the CGRP molecule have an inhibitory effect on the pain process and can be used as an abortive treatment. Monoclonal antibodies against CGRP can have a long half-life, which means that they can be administered less frequently than typical migraine medications that are taken daily (with the exception of botulinum toxin, which is injected every 90 days). Monoclonal antibodies for migraines can be injected under the skin monthly, and have thus far demonstrated a statistically significant decrease in days of migraine. Several different drug companies are developing these new antibodies for FDA approval.

Although such monoclonal anti-CGRP or anti-CGRP receptor antibodies may prove efficacious in immunotherapy of migraine, they are expensive and must be administered monthly to maintain sufficient suppression of serum and body fluid CGRP levels and the clinical benefits derived therefrom. Cost effective immunotherapeutic treatment targeting CGRP molecule through vaccination approach that is safe and well tolerated remains an exciting new intervention and development for migraine therapies.

There are a number of disadvantages and deficiencies associated with the classical peptide/hapten-carrier protein immunogen preparation method. For example, the preparation methods can involve complicated chemical coupling procedures, they use expensive pharmaceutical grade KLH or toxoid protein as the T helper cell carrier, most of the antibodies elicited by the protein immunogens are directed against the carrier protein and not the target B cell epitope(s), etc.

In view of the economic and practical disadvantages and limitations with monoclonal therapy and classical peptide/hapten-carrier protein preparations, there is clearly an unmet need to develop an efficacious immunotherapeutic composition capable of eliciting highly specific immune responses against the functional site(s) on CGRP, that can be easily administered to patients, that is able to be manufactured under stringent good manufacturing practices (GMP), and that is cost effective for worldwide application to treat patients suffering from migraine.

Two review articles that cite to additional supporting documents can be found for statements made in the above background section are hereby incorporated by reference in their entireties. The first article contains an updated review on CGRP and CGRP receptors (website: en.wikipedia.org/wiki/Calcitonin_gene-related_peptide), and the second article addresses the biology of CGRP signaling, key clinical evidence for the role of CGRP in migraine headache including the efficacy of CGRP-targeted treatment, the role of CGRP in the trigemino vascular system, and new insight into the central role of the trigeminal ganglion in the pathophysiology of migraine (Edvinsson, et al., 2018).

REFERENCES

1. CHANG, J. C. C., et al., "Adjuvant activity of incomplete Freund's adjuvant," Advanced Drug Delivery Reviews, 32(3):173-186 (1998)
2. "Calcitonin gene-related peptide," *Wikipedia, The Free Encyclopedia*, website address: en.wikipedia.org/wiki/Calcitonin_gene-related_peptide (accessed Dec. 30, 2018).
3. EDVINSSON, L., et al., "CGRP as the target of new migraine therapies—successful translation from bench to clinic", *Nat. Rev. Neurol.*, 14(6):338-350 (2018)
4. FIELDS, G. B., et al., Chapter 3 in Synthetic Peptides: A User's Guide, ed. Grant, W.H. Freeman & Co., New York, NY, p. 77 (1992).
5. RUSSELL, F. A., et al., "Calcitonin gene-related peptide: physiology and pathophysiology", *Physiol. Rev.*, 94(4): 1099-1142 (2014)

6. TAJTI, J., et al., "Messenger molecules and receptor mRNA in the human trigeminal ganglion", *J. Auton. Nerv. Syst.* 28; 76(2-3):176-83 (1999)

7. TRAGGIAI, E., et al., "An efficient method to make human monoclonal antibodies from memory B cells: potent neutralization of SARS coronavirus", *Nature Medicine,* 10:871-875 (2004).

8. WATKINS, H. A., et al., "Structure-activity relationships for a-calcitonin gene-related peptide", *Br. J. Pharmacol.,* 170(7):1308-22 (2013)

SUMMARY OF THE INVENTION

The present disclosure is directed to portions of the Calcitonin Gene-Related Peptide (CGRP) that can be used as B cell epitopes. The present disclosure is also directed to peptide immunogen constructs containing B cell epitopes from CGRP, compositions containing the peptide immunogen constructs, methods of making and using the peptide immunogen constructs, and antibodies produced by the peptide immunogen constructs.

One aspect of the present disclosure is directed to portions of CGRP from different organisms as B cell epitopes in peptide immunogen constructs, as well as formulations thereof, that can be used for the prevention and/or treatment of migraine. The disclosed CGRP peptide immunogen constructs (SEQ ID NOs: 116-127 and 130-180) have 30 or more total amino acids and contain a functional B cell epitope peptide having about 7 to about 30 amino acids (SEQ ID NOs: 4-13, 15-19, and 20-24 of Table 1) derived from CGRP from human, marmoset, or rat/mouse (i.e., SEQ ID NOs: 1-3, respectively). The functional B cell epitope peptide can be linked through an optional heterologous spacer to a heterologous T helper cell (Th) epitope peptide derived from pathogen proteins (e.g., SEQ ID NOs: 74-115), to form the disclosed peptide immunogen construct.

The disclosed CGRP peptide immunogen constructs can contain a CGRP B cell epitope peptide having about 7 to about 30 amino acids. The B cell epitope peptide can be derived from the CGRP receptor binding region (e.g., SEQ ID NOs: 5-9 and 15-22, shown in Table 1) located at the C-terminal and central regions of the CGRP molecule. The B cell epitope peptide can also be derived from the CGRP receptor activation site around a cyclic C2-C7 loop (e.g. SEQ ID NOs: 4, 10-13 and 23-24, shown in Table 1) located at the N-terminal and central regions of the CGRP molecule. The designed CGRP B cell epitope peptide can be linked to a heterologous Th epitope derived from a pathogenic protein (e.g., SEQ ID NOs: 74-115 of Table 2) at either the N- or C-terminus of the CGRP peptide. The B cell and Th epitopes act together to stimulate the generation of highly specific antibodies cross-reactive with full-length CGRP (SEQ ID NO:1-3) of various species.

In certain embodiments, the heterologous Th epitopes employed to enhance the CGRP B cell epitope peptide are derived from natural pathogens EBV BPLF1 (SEQ ID NO: 112), EBV CP (SEQ ID NO: 109), *Clostridium Tetani* (SEQ ID NOs: 74, 77, 104, 106-108), Cholera Toxin (SEQ ID NO: 81), and *Schistosoma mansoni* (SEQ ID NO: 80), as well as those idealized artificial Th epitopes derived from Measles Virus Fusion protein (MVF 1 to 5) and Hepatitis B Surface Antigen (HBsAg 1 to 3) in the form of either single sequence or combinatorial sequences (e.g. SEQ ID NOs: 75, 82-99).

The disclosed CGRP peptide immunogen constructs, containing both designed B cell- and Th epitope peptides, act together to stimulate the generation of highly specific antibodies directed against CGRP functional sites, including the CGRP receptor binding region located at the C-terminal of the CGRP molecule or the cyclic C2-C7 loop involved in receptor activation, offer therapeutic immune responses to patients predisposed to, or suffering from, migraine.

Another aspect of the present disclosure is directed to peptide compositions containing a CGRP peptide immunogen construct. In some embodiments, the compositions contain one peptide immunogen construct. In other embodiments, peptide compositions comprising a mixture of CGRP peptide immunogen constructs. In certain embodiments, the mixture of CGRP peptide immunogen constructs have heterologous Th epitopes derived from different pathogens that can be used to allow coverage of as broad a genetic background in patients leading to a higher percentage in responder rate upon immunization for the prevention and/or treatment of migraine.

Synergistic enhancement in CGRP immunogen constructs can be observed in the peptide compositions of this disclosure. The antibody response derived from the administration of such compositions containing CGPR peptide immunogen constructs was mostly (>90%) focused on the desired cross-reactivity against the CGRP functional site(s) or receptor binding region peptides (SEQ ID NOs: 4-13 and 15-24) without much, if any, directed to the heterologous Th epitopes employed for immunogenicity enhancement. This is in sharp contrast to standard methods that use a conventional carrier protein, such as KLH, toxoid, or other biological carriers used for such peptide antigenicity enhancement The present disclosure is also directed to pharmaceutical compositions and formulations for the prevention and/or treatment of migraine. In some embodiments, pharmaceutical compositions comprising a stabilized immunostimulatory complex, which is formed by mixing a CpG oligomer with a peptide composition containing a mixture of CGRP peptide immunogen constructs through electrostatic association, to further enhance the CGRP peptide immunogenicity towards the desired cross-reactivity with the full-length CGRP (e.g., SEQ ID NOs: 1-3).

In other embodiments, pharmaceutical compositions comprising a peptide composition of a mixture of CGRP peptide immunogen constructs in contact with mineral salts including Alum gel (ALHYDROGEL) or Aluminum phosphate (ADJU-PHOS) to form a suspension formulation, or with MONTANIDE™ ISA 51 or 720 as adjuvant to form water-in-oil emulsions, that can be used for the prevention and/or treatment of migraine.

Furthermore, the present disclosure also provides a method for the low cost manufacture and quality control of CGRP peptide immunogen constructs and formulations thereof, capable of preventing and/or treating migraine in animals.

The present disclosure is also directed to antibodies directed against the disclosed CGRP peptide immunogen constructs. In particular, the CGRP peptide immunogen constructs of the present disclosure are able to stimulate the generation of highly specific functional antibodies that are cross-reactive with the full-length CGRP molecule. The disclosed antibodies bind with high specificity to CGRP without much, if any, directed to the heterologous Th epitopes employed for immunogenicity enhancement, which is in sharp contrast to antibodies produced using conventional proteins or other biological carriers used for such peptide immunogenicity enhancement. Thus, the disclosed CGRP peptide immunogen constructs are capable of breaking the immune tolerance against self-CGRP, with a high responder rate, compared to other peptide or protein immunogens.

In some embodiments, the disclosed antibodies are directed against and specifically bind to the CGRP receptor binding sites on the C-terminal portion of the CGRP molecule (e.g., SEQ ID NOs: 5-9 and 15-22) when the peptide immunogen constructs are administered to a subject. The highly specific antibodies elicited by these CGRP peptide immunogen constructs can inhibit CGRP and CGRP receptor binding and the downstream activation event in the rise of cellular CAMP caused by the region around the cyclic C2-C7 loop of the CGRP, leading to effective prevention and/or treatment of migraine.

In other embodiments, the disclosed antibodies are directed against either the N-terminal or central regions of CGRP around the cyclic C2-C7 loop responsible for the downstream cell activation event or against the C-terminal and central regions of the CGRP receptor binding site, when the peptide immunogen constructs of current invention are administered to a subject (e.g., SEQ ID NOs: 4, 10-13, and 23-24). The highly specific antibodies elicited by the CGRP peptide immunogen constructs can inhibit (1) CGRP and CGRP receptor binding and (2) the downstream activation event caused by the region around the cyclic C2-C7 loop of the CGRP, resulting in the suppression of the rise of cellular cAMP, thus leading to effective treatment of patients suffering from migraine.

Based on their unique characteristics and properties, the disclosed antibodies elicited by the CGRP peptide immunogen constructs are capable of providing a prophylactic immunotherapeutic approach to treating patients suffering from migraine.

In a further aspect, the present invention provides human monoclonal antibodies against CGRP induced by patients receiving compositions containing CGRP peptide immunogen constructs of this disclosure. An efficient method to make human monoclonal antibodies from B cells isolated from the blood of a human patient is described by Traggiai, E., et al, 2004, which is incorporated by reference.

The present disclosure is also directed to methods of making the disclosed CGRP peptide immunogen constructs, compositions, and antibodies. The disclosed methods provide for the low cost manufacture and quality control of CGRP peptide immunogen constructs and compositions containing the constructs, which can be used in methods for treating patients suffering from migraine.

The present disclosure also includes methods for preventing and/or treating subjects predisposed to, or suffering from, migraine using the disclosed CGRP peptide immunogen constructs and/or antibodies directed against the CGRP peptide immunogen constructs. The methods for preventing and/or treating migraine in a subject include administering to the subject a composition containing a disclosed CGRP peptide immunogen construct. In certain embodiments, the compositions utilized in the methods contain a disclosed CGRP peptide immunogen construct in the form of a stable immunostimulatory complex with negatively charged oligonucleotides, such as CpG oligomers, through electrostatic association, which can be further supplemented with an adjuvant, for administration to patients suffering from migraine.

The disclosed methods also include dosing regimens, dosage forms, and routes for administering the CGRP peptide immunogen constructs to prevent and/or treat migraine in a subject.

BRIEF DESCRIPTION OF THE DRAWINGS

FIG. 1 presents alignment of CGRP sequences from multispecies including human (SEQ ID NO: 1), marmoset (SEQ ID NO:2), mouse (SEQ ID NO: 3), rat (SEQ ID NO: 3), and many others including horse, chicken, pig, sheep, cow, dog, opossum, Gecko, Frog, Pufferfish, Flounder, Goldfish, Salmon, Medalea, Zebrafish. This Figure is adapted from Watkins, et al., 2013.

DETAILED DESCRIPTION OF THE INVENTION

Figure 2:
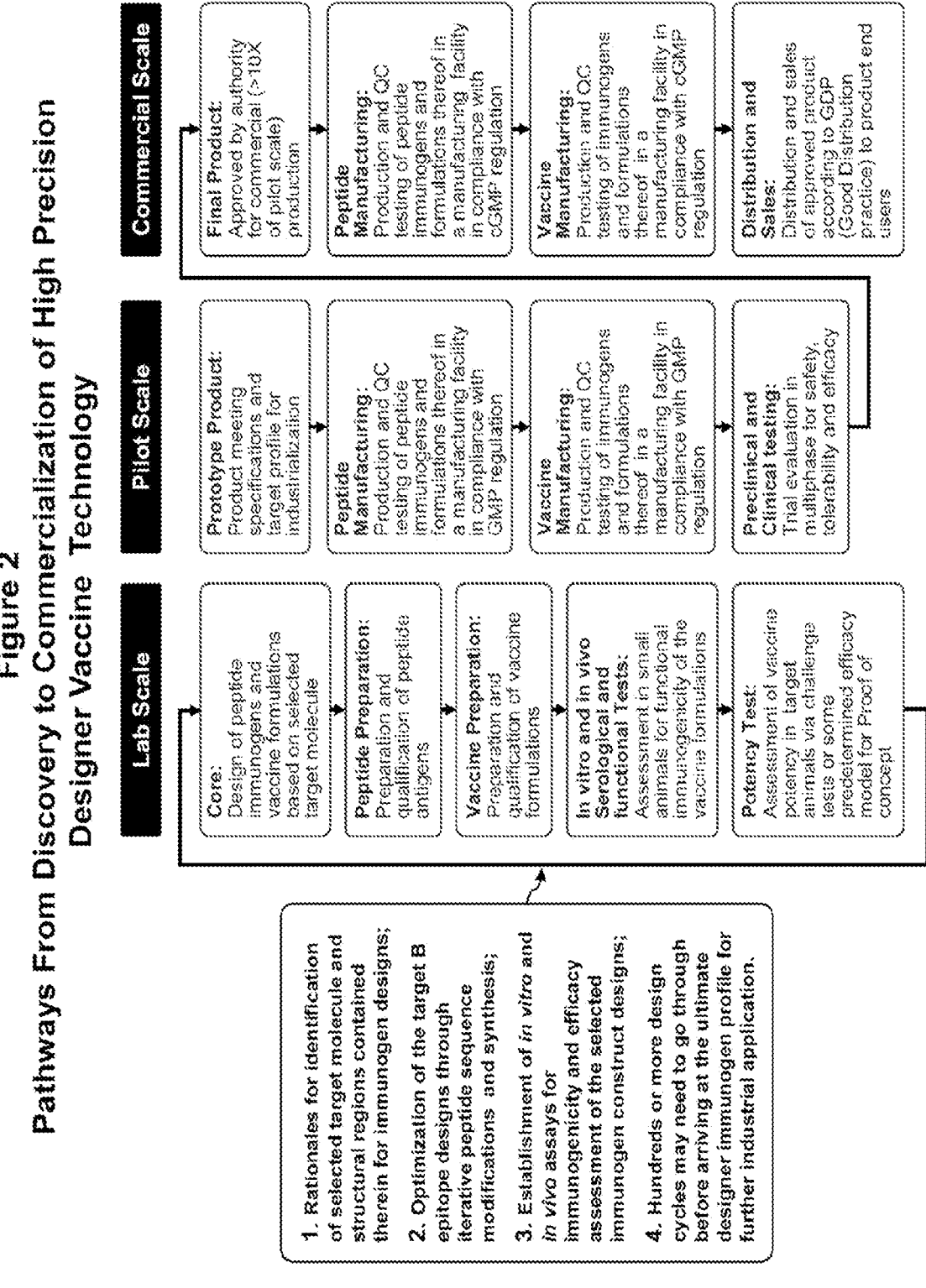
FIG. 2 depicts pathways from discovery to commercialization of high precision CGRP designer peptide immunogen constructs and formulations thereof for the treatment of migraine.

The present disclosure is directed to portions of the Calcitonin Gene-Related Peptide (CGRP) that can be used as B cell epitopes. The present disclosure is also directed to peptide immunogen constructs containing B cell epitopes from CGRP, compositions containing the peptide immunogen constructs, methods of making and using the peptide immunogen constructs, and antibodies produced by the peptide immunogen constructs.

One aspect of the present disclosure is directed to portions of CGRP from different organisms as B cell epitopes in peptide immunogen constructs, as well as formulations thereof, that can be used for the prevention and/or treatment of migraine. The disclosed CGRP peptide immunogen constructs (SEQ ID NOs: 116-127 and 130-180) have 30 or more total amino acids and contain a functional B cell epitope peptide having about 7 to about 30 amino acids (SEQ ID NOs: 4-13, 15-19, and 20-24 of Table 1) derived from CGRP from human, marmoset, or rat/mouse (i.e., SEQ ID NOs: 1-3, respectively). The functional B cell epitope peptide can be linked through an optional heterologous spacer to a heterologous T helper cell (Th) epitope peptide derived from pathogen proteins (e.g., SEQ ID NOs: 74-115), to form the disclosed peptide immunogen construct.

The disclosed CGRP peptide immunogen constructs can contain a CGRP B cell epitope peptide having about 7 to about 30 amino acids. The B cell epitope peptide can be derived from the CGRP receptor binding region (e.g., SEQ ID NOs: 5-9 and 15-22, shown in Table 1) located at the C-terminal and central regions of the CGRP molecule. The B cell epitope peptide can also be derived from the CGRP receptor activation site around a cyclic C2-C7 loop (e.g. SEQ ID NOs: 4, 10-13, and 20-22, shown in Table 1) located at the N-terminal and central regions of the CGRP molecule. The designed CGRP B cell epitope peptide can be linked to a heterologous Th epitope derived from a pathogenic protein (e.g., SEQ ID NOs: 74-115 of Table 2) at either the N- or C-terminus of the CGRP peptide. The B cell and Th epitopes act together to stimulate the generation of highly specific antibodies cross-reactive with full-length CGRP (SEQ ID NO: 1-3) of various species.

In certain embodiments, the heterologous Th epitopes employed to enhance the CGRP B cell epitope peptide are derived from natural pathogens EBV BPLF1 (SEQ ID NO: 112), EBV CP (SEQ ID NO: 109), *Clostridium Tetani* (SEQ ID NOs: 74, 77, 104, 106-108), Cholera Toxin (SEQ ID NO: 81), and *Schistosoma mansoni* (SEQ ID NO: 80), as well as those idealized artificial Th epitopes derived from Measles Virus Fusion protein (MVF 1 to 5) and Hepatitis B Surface Antigen (HBsAg 1 to 3) in the form of either single sequence or combinatorial sequences (e.g. SEQ ID NOs: 75, 82-99).

The disclosed CGRP peptide immunogen constructs, containing both designed B cell- and Th epitope peptides, act together to stimulate the generation of highly specific antibodies directed against CGRP functional sites, including the CGRP receptor binding region located at the C-terminal of the CGRP molecule or the cyclic C2-C7 loop involved in receptor activation, offer therapeutic immune responses to patients predisposed to, or suffering from, migraine.

Another aspect of the present disclosure is directed to peptide compositions containing a CGRP peptide immunogen construct. In some embodiments, the compositions contain one peptide immunogen construct. In other embodiments, peptide compositions comprising a mixture of CGRP peptide immunogen constructs. In certain embodiments, the mixture of CGRP peptide immunogen constructs have heterologous Th epitopes derived from different pathogens that can be used to allow coverage of as broad a genetic background in patients leading to a higher percentage in responder rate upon immunization for the prevention and/or treatment of migraine.

Synergistic enhancement in CGRP immunogen constructs can be observed in the peptide compositions of this disclosure. The antibody response derived from the administration of such compositions containing CGPR peptide immunogen constructs was mostly (>90%) focused on the desired cross-reactivity against the CGRP functional site(s) or receptor binding region peptides (SEQ ID NOs: 4-13, 15-19, and 20-24) without much, if any, directed to the heterologous Th epitopes employed for immunogenicity enhancement. This is in sharp contrast to standard methods that use a conventional carrier protein, such as KLH, toxoid, or other biological carriers used for such peptide antigenicity enhancement The present disclosure is also directed to pharmaceutical compositions and formulations for the prevention and/or treatment of migraine. In some embodiments, pharmaceutical compositions comprising a stabilized immunostimulatory complex, which is formed by mixing a CpG oligomer with a peptide composition containing a mixture of CGRP peptide immunogen constructs through electrostatic association, to further enhance the CGRP peptide immunogenicity towards the desired cross-reactivity with the full-length CGRP (e.g., SEQ ID NOs: 1-3).

In other embodiments, pharmaceutical compositions comprising a peptide composition of a mixture of CGRP peptide immunogen constructs in contact with mineral salts including Alum gel (ALHYDROGEL) or Aluminum phosphate (ADJU-PHOS) to form a suspension formulation, or with MONTANIDE™ ISA 51 or 720 as adjuvant to form water-in-oil emulsions, that can be used for the prevention and/or treatment of migraine.

Furthermore, the present disclosure also provides a method for the low cost manufacture and quality control of CGRP peptide immunogen constructs and formulations thereof, capable of preventing and/or treating migraine in animals.

The present disclosure is also directed to antibodies directed against the disclosed CGRP peptide immunogen constructs. In particular, the CGRP peptide immunogen constructs of the present disclosure are able to stimulate the generation of highly specific functional antibodies that are cross-reactive with the full-length CGRP molecule. The disclosed antibodies bind with high specificity to CGRP without much, if any, directed to the heterologous Th epitopes employed for immunogenicity enhancement, which is in sharp contrast to antibodies produced using conventional proteins or other biological carriers used for such peptide immunogenicity enhancement. Thus, the disclosed CGRP peptide immunogen constructs are capable of breaking the immune tolerance against self-CGRP, with a high responder rate, compared to other peptide or protein immunogens.

In some embodiments, the disclosed antibodies are directed against and specifically bind to the CGRP receptor binding sites on the C-terminal portion of the CGRP molecule (e.g., SEQ ID NOs: 5-9 and 15-22) when the peptide immunogen constructs are administered to a subject. The highly specific antibodies elicited by these CGRP peptide immunogen constructs can inhibit CGRP and CGRP receptor binding and the downstream activation event in the rise of cellular CAMP caused by the region around the cyclic C2-C7 loop of the CGRP, leading to effective prevention and/or treatment of migraine.

In other embodiments, the disclosed antibodies are directed against either the N-terminal or central regions of CGRP around the cyclic C2-C7 loop responsible for the downstream cell activation event or against the C-terminal and central regions of the CGRP receptor binding site, when the peptide immunogen constructs of current invention are administered to a subject (e.g., SEQ ID NOs: 4, 10-13, and 23-24). The highly specific antibodies elicited by the CGRP peptide immunogen constructs can inhibit (1) CGRP and CGRP receptor binding and (2) the downstream activation event caused by the region around the cyclic C2-C7 loop of the CGRP, resulting in the suppression of the rise of cellular cAMP, thus leading to effective treatment of patients suffering from migraine.

Based on their unique characteristics and properties, the disclosed antibodies elicited by the CGRP peptide immunogen constructs are capable of providing a prophylactic immunotherapeutic approach to treating patients suffering from migraine.

In a further aspect, the present invention provides human monoclonal antibodies against CGRP induced by patients receiving compositions containing CGRP peptide immunogen constructs of this disclosure. An efficient method to make human monoclonal antibodies from B cells isolated from the blood of a human patient is described by Traggiai, E., et al, 2004, which is incorporated by reference.

The present disclosure is also directed to methods of making the disclosed CGRP peptide immunogen constructs, compositions, and antibodies. The disclosed methods provide for the low cost manufacture and quality control of CGRP peptide immunogen constructs and compositions containing the constructs, which can be used in methods for treating patients suffering from migraine.

The present disclosure also includes methods for preventing and/or treating subjects predisposed to, or suffering from, migraine using the disclosed CGRP peptide immunogen constructs and/or antibodies directed against the CGRP peptide immunogen constructs. The methods for preventing and/or treating migraine in a subject include administering to the subject a composition containing a disclosed CGRP peptide immunogen construct. In certain embodiments, the compositions utilized in the methods contain a disclosed CGRP peptide immunogen construct in the form of a stable immunostimulatory complex with negatively charged oligonucleotides, such as CpG oligomers, through electrostatic association, which can be further supplemented with an adjuvant, for administration to patients suffering from migraine.

The disclosed methods also include dosing regimens, dosage forms, and routes for administering the CGRP peptide immunogen constructs to prevent and/or treat migraine in a subject.

General

The section headings used herein are for organizational purposes only and are not to be construed as limiting the subject matter described. All references or portions of references cited in this application are expressly incorporated by reference herein in their entirety for any purpose.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence, the phrase "comprising A or B" means including A, or B, or A and B. It is further to be understood that all amino acid sizes, and all molecular weight or molecular mass values, given for polypeptides are approximate, and are provided for description. Although methods and materials similar or equivalent to those described herein can be used in the practice or testing of the disclosed method, suitable methods and materials are described below. All publications, patent applications, patents, and other references mentioned herein are incorporated by reference in their entirety. In case of conflict, the present specification, including explanations of terms, will control. In addition, the materials, methods, and examples disclosed herein are illustrative only and not intended to be limiting.

CGRP Peptide Immunogen Construct

The present disclosure provides peptide immunogen constructs containing a B cell epitope peptide with an amino acid sequence from CGRP (SEQ ID NOs: 1-3) or fragments thereof. The CGRP peptide immunogen constructs can contain a CGRP B epitope peptide having about 7 to about 30 amino acids. The B cell epitope peptides can be from (1) the CGRP receptor binding region (e.g., SEQ ID NOs: 5-9 and 15-22, shown in Table 1) located at the C-terminal/central region of the CGRP molecule; or (2) from the CGRP receptor activation site around a cyclic C2-C7 loop (e.g. SEQ ID NOs: 4, 10-13 and 23-24, shown in Table 1) located at the N-terminal/central region of the CGRP molecule. The B cell epitope can be covalently linked to a heterologous T helper cell (Th) epitope derived from a pathogen protein (e.g., SEQ ID NOs: 74-115, shown in Table 2) directly or through an optional heterologous spacer. These constructs, containing both designed B cell- and Th cell epitopes act together to stimulate the generation of highly specific antibodies that are cross-reactive with full-length CGRP (SEQ ID NO:1-3) of various species.

The phrase "CGRP peptide immunogen construct" or "peptide immunogen construct", as used herein, refers to a peptide with more than about 30 amino acids containing (a) a B cell epitope having about more than about 7 contiguous amino acid residues from the full-length CGRP (SEQ ID NOs: 1-3); (b) a heterologous Th epitope; and (c) an optional heterologous spacer.

In certain embodiments, the CGRP peptide immunogen construct can be represented by the formulae:

$$(Th)_m\text{-}(A)_n\text{-}(\text{CGRP functional B epitope peptide})\text{-}X$$

or $$(\text{CGRP functional B epitope peptide})\text{-}(A)_n\text{-}(Th)_m\text{-}X$$

or $$(Th)_m\text{-}(A)_n\text{-}(\text{CGRP functional B epitope peptide})\text{-}(A)_n\text{-}(Th)_m\text{-}X$$

wherein

Th is a heterologous T helper epitope;

A is a heterologous spacer;

(CGRP functional B epitope peptide) is a B cell epitope peptide having from 7 to 30 amino acid residues from CGRP that are involved in either receptor binding or receptor activation;

X is an $\alpha\text{-COOH}$ or $\alpha\text{-CONH}_2$ of an amino acid;

m is from 1 to about 4; and n is from 0 to about 10.

The CGRP peptide immunogen constructs of the present disclosure were designed and selected based on a number of rationales, including:

i. the CGRP B cell epitope peptide is non-immunogenic on its own to avoid autologous T cell activation;

ii. the CGRP B cell epitope peptide can be rendered immunogenic by using a protein carrier or a potent T helper epitope(s);

iii. when the CGRP B cell epitope peptide rendered immunogenic and administered to a host, the peptide immunogen construct:

a. elicits high titer antibodies preferentially directed against the CGRP B cell epitope(s) and not the protein carrier or T helper epitope(s);

b. breaks immune tolerance in the immunized host and generates highly specific antibodies having cross-reactivity with the CGRP (SEQ ID NOs: 1-3);

c. generates highly specific antibodies capable of inhibiting CGRP and CGRP receptor binding and the associated downstream events such as rise in intracellular cAMP production; and d. generates highly specific antibodies capable reduction in vivo of capsaicin triggered dermal blood flow.

The disclosed CGRP peptide immunogen constructs and formulations thereof can effectively function as a pharmaceutical composition to prevent and/or treat subjects predisposed to, or suffering from, migraine.

The various components of the disclosed CGRP peptide immunogen construct are described in further detail below.

a. B Cell Epitope Peptide from CGRP

The present disclosure is directed to a novel peptide composition for the generation of high titer antibodies with specificity for the Calcitonin Gene-Related Peptide (CGRP) protein of multi-species (e.g., SEQ ID NOs: 1-3). The site-specificity of the peptide immunogen constructs minimizes the generation of antibodies that are directed to irrelevant sites on other regions of CGRP or irrelevant sites on carrier proteins, thus providing a high safety factor.

The term "CGRP", as used herein, refers to the 37-amino acid neuropeptide α-CGRP belonging to the calcitonin (CT) family of peptides. Human CGRP is derived from UniProtKB: P06881-1 and has the amino acid sequence of SEQ ID NO: 1. Marmoset (Callithrix jacchus) CGRP is derived from GenBank Accession No.: AAL35592.1 and has the amino acid sequence of SEQ ID NO:2. Rat (*Rattus norvegicus*) CGRP is derived from UniProtKB: P01256 and mouse (*Mus musculus*) CGRP is derived from UniProtKB: Q99JA0 and both rat and mouse CGRP have the amino acid sequence of SEQ ID NO: 3. The amino acid sequences of CGRP used in the present disclosure are shown in Table 1.

In humans, CGRP is derived from the gene encoding calcitonin, is formed from the alternative splicing of the calcitonin/CGRP gene located on chromosome 11. In humans, CGRP has two isoforms: α-CGRP and β-CGRP. The α-isoform differs from the β-isoform in the amino acids located at positions 3, 22 and 25. On a molecular level within smooth muscle cells, CGRP could bind to its receptor via its C-terminal region and then activate the receptor by using its loop region. The cyclic C2-C7 loop with a disulfide bridge has a basic role in receptor activation and correlates closely with a rise in intracellular cAMP. In the mammalian plasma, the half-life of CGRP is approximately 10 minutes. In the human trigeminal ganglia, CGRP-reactive neurons account for up to 50% of all neurons (Tajti, et al., 1999).

CGRP is widely expressed in the central and peripheral nervous system. It is primarily associated with small unmyelinated sensory neurons in close proximity of blood vessels. CGRP is a potent vasodilator and local administration of CGRP causes transient increases in blood flow. CGRP has also been associated with pain transmission, pain modulation, and neurogenic inflammation. CGRP can be released from sensory neurons via activation of the transient receptor potential cation channel V1 using capsaicin. Laser Doppler Imaging (LDI) has been used to detect the resulting changes in dermal blood flow caused by CGRP.

CGRP is also linked to inflammatory pain as demonstrated by attenuated responses in CGRP knock-out mice in a number of pain models. This role in pain perception is congruent with the expression of CGRP in sensory neurons.

One aspect of the present disclosure is to prevent and/or treat CGRP-migraine headaches with an active immunotherapy that targets CGRP to exert long-term CGRP blockade and clinical efficacy. Thus, the present disclosure is directed to peptide immunogen constructs targeting portions of the full-length CGRP protein (SEQ ID NO: 1-3) and formulations thereof for prevention and treatment of migraine.

The B cell epitope portion of the CGRP peptide immunogen construct can contain between about 7 to about 30 amino acids from any portion of the full-length CGRP protein represented by SEQ ID NOs: 1-3. In certain embodiments, the B cell epitope peptide, screened and selected based on design rationales, contains an amino acid sequence of SEQ ID NOs: 4-13, and 15-24 as shown in Table 1.

In some embodiments, the B cell epitope peptide is from the CGRP receptor binding region located at the C-terminal/central region of the CGRP molecule R11-F37 (SEQ ID NO: 9), or fragments thereof (e.g. SEQ ID NOs: 5-8 and 15-22). In other embodiments, the B cell epitope peptide is from the CGRP receptor activation region around the cyclic C2-C7 loop such as A1-N25 (SEQ ID NO: 13) or fragments thereof (e.g. SEQ ID NOs: 4, 10-12, and 23-24).

The CGRP B cell epitope peptide of the present disclosure also includes immunologically functional analogues or homologues of the CGRP. Functional immunological analogues or homologues of CGRP B cell epitope peptide include variants that retain substantially the same immunogenicity as the original peptide. Immunologically functional analogues can have a conservative substitution in an amino acid position; a change in overall charge; a covalent attachment to another moiety; or amino acid additions, insertions, or deletions; and/or any combination thereof (e.g. CGRP peptides of SEQ ID NOs: 9 vs 25).

Antibodies generated from peptide immunogen constructs containing these B cell epitope from CGRP are highly specific and cross-reactive with the full-length CGRP of various species (e.g., SEQ ID NOs: 1-3). Based on their unique characteristics and properties, the disclosed antibodies elicited by the CGRP peptide immunogen constructs are capable of providing a prophylactic immunotherapeutic approach to preventing and/or treating migraine.

b. Heterologous T Helper Cell Epitopes (Th Epitopes)

The present disclosure provides peptide immunogen constructs containing a B cell epitope from CGRP covalently linked to a heterologous T helper cell (Th) epitope directly or through an optional heterologous spacer.

The heterologous Th epitope in the CGRP peptide immunogen construct enhances the immunogenicity of the CGRP fragment, which facilitates the production of specific high titer antibodies directed against the optimized target CGRP B cell epitope peptide screened and selected based on design rationales.

The term "heterologous", as used herein, refers to an amino acid sequence that is derived from an amino acid sequence that is not part of, or homologous with, the wild-type sequence of CGRP. Thus, a heterologous Th epitope is a Th epitope derived from an amino acid sequence that is not naturally found in CGRP (i.e., the Th epitope is not autologous to CGRP). Since the Th epitope is heterologous to CGRP, the natural amino acid sequence of CGRP is not extended in either the N-terminal or C-terminal directions when the heterologous Th epitope is covalently linked to the CGRP B epitope peptide.

The heterologous Th epitope of the present disclosure can be any Th epitope that does not have an amino acid sequence naturally found in CGRP. The Th epitope can also have promiscuous binding motifs to MHC class II molecules of multiple species. In certain embodiments, the Th epitope comprises multiple promiscuous MHC class II binding motifs to allow maximal activation of T helper cells leading to initiation and regulation of immune responses. The Th epitope is preferably immunosilent on its own, i.e. little, if any, of the antibodies generated by the CGRP peptide immunogen constructs will be directed towards the Th epitope, thus allowing a very focused immune response directed to the targeted B cell epitope peptide of the CGRP molecule.

Th epitopes of the present disclosure include, but are not limited to, amino acid sequences derived from foreign pathogens, as exemplified in Table 2 (SEQ ID NOs: 74-115). Further, Th epitopes include idealized artificial Th epitopes and combinatorial idealized artificial Th epitopes (e.g., SEQ ID NOs: 75 and 82-99). The heterologous Th epitope peptides presented as a combinatorial sequence (e.g., SEQ ID NOs: 85, 91, 94, and 97), contain a mixture of amino acid residues represented at specific positions within the peptide framework based on the variable residues of homologues for that particular peptide. An assembly of combinatorial peptides can be synthesized in one process by adding a mixture of the designated protected amino acids, instead of one particular amino acid, at a specified position during the synthesis process. Such combinatorial heterologous Th epitope peptides assemblies can allow broad Th epitope coverage for animals having a diverse genetic background. Representative combinatorial sequences of heterologous Th epitope peptides include SEQ ID NOs: 85, 91, 94, and 97 which are shown in Table 2. Th epitope peptides of the present invention provide broad reactivity and immunogenicity to animals and patients from genetically diverse populations.

c. Heterologous Spacer

The disclosed CGRP peptide immunogen constructs optionally contain a heterologous spacer that covalently links the CGRP B cell epitope peptide to the heterologous T helper cell (Th) epitope.

As discussed above, the term "heterologous", refers to an amino acid sequence that is derived from an amino acid sequence that is not part of, or homologous with, the natural type sequence of CGRP. Thus, the natural amino acid sequence of CGRP is not extended in either the N-terminal or C-terminal directions when the heterologous spacer is covalently linked to the CGRP B cell epitope peptide because the spacer is heterologous to the CGRP sequence.

The spacer is any molecule or chemical structure capable of linking two amino acids and/or peptides together. The spacer can vary in length or polarity depending on the application. The spacer attachment can be through an amide- or carboxyl-linkage but other functionalities are possible as well. The spacer can include a chemical compound, a naturally occurring amino acid, or a non-naturally occurring amino acid.

The spacer can provide structural features to the CGRP peptide immunogen construct. Structurally, the spacer provides a physical separation of the Th epitope from the B cell epitope of the CGRP fragment. The physical separation by the spacer can disrupt any artificial secondary structures created by joining the Th epitope to the B cell epitope. Additionally, the physical separation of the epitopes by the spacer can eliminate interference between the Th cell and/or B cell responses. Furthermore, the spacer can be designed to create or modify a secondary structure of the peptide immunogen construct. For example, a spacer can be designed to act as a flexible hinge to enhance the separation of the Th epitope and B cell epitope. A flexible hinge spacer can also permit more efficient interactions between the presented peptide immunogen and the appropriate Th cells and B cells to enhance the immune responses to the Th epitope and B cell epitope. Examples of sequences encoding flexible hinges are found in the immunoglobulin heavy chain hinge region, which are often proline rich. One particularly useful flexible hinge that can be used as a spacer is provided by the sequence Pro-Pro-Xaa-Pro-Xaa-Pro (SEQ ID NO: 71), where Xaa is any amino acid, and preferably aspartic acid.

The spacer can also provide functional features to the CGRP peptide immunogen construct. For example, the spacer can be designed to change the overall charge of the CGRP peptide immunogen construct, which can affect the solubility of the peptide immunogen construct. Additionally, changing the overall charge of the CGRP peptide immunogen construct can affect the ability of the peptide immunogen construct to associate with other compounds and reagents. As discussed in further detail below, the CGRP peptide immunogen construct can be formed into a stable immunostimulatory complex with a highly charged oligonucleotide, such as CpG oligomers, through electrostatic association. The overall charge of the CGRP peptide immunogen construct is important for the formation of these stable immunostimulatory complexes.

Chemical compounds that can be used as a spacer include, but are not limited to, (2-aminoethoxy) acetic acid (AEA), 5-aminovaleric acid (AVA), 6-aminocaproic acid (Ahx), 8-amino-3,6-dioxaoctanoic acid (AEEA, mini-PEG1), 12-amino-4,7,10-trioxadodecanoic acid (mini-PEG2), 15-amino-4,7,10,13-tetraoxapenta-decanoic acid (mini-PEG3), trioxatridecan-succinamic acid (Ttds), 12-amino-dodecanoic acid, Fmoc-5-amino-3-oxapentanoic acid (O1Pen), and the like.

Naturally-occurring amino acids include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

Non-naturally occurring amino acids include, but are not limited to, ε-N Lysine, β-alanine, ornithine, norleucine, norvaline, hydroxyproline, thyroxine, γ-amino butyric acid, homoserine, citrulline, aminobenzoic acid, 6-aminocaproic acid (Aca; 6-Aminohexanoic acid), hydroxyproline, mercaptopropionic acid (MPA), 3-nitro-tyrosine, pyroglutamic acid, and the like.

The spacer in the CGRP peptide immunogen construct can be covalently linked at either N- or C-terminal end of the Th epitope and the CGRP B cell epitope peptide. In some embodiments, the spacer is covalently linked to the C-terminal end of the Th epitope and to the N-terminal end of the CGRP B cell epitope peptide. In other embodiments, the spacer is covalently linked to the C-terminal end of the CGRP B cell epitope peptide and to the N-terminal end of the Th epitope. In certain embodiments, more than one spacer can be used, for example, when more than one Th epitope is present in the CGRP peptide immunogen construct. When more than one spacer is used, each spacer can be the same as each other or different. Additionally, when more than one Th epitope is present in the CGRP peptide immunogen construct, the Th epitopes can be separated with a spacer, which can be the same as, or different from, the spacer used to separate the Th epitope from the CGRP B cell epitope peptide. There is no limitation in the arrangement of the spacer in relation to the Th epitope or the CGRP B cell epitope peptide.

In certain embodiments, the heterologous spacer is a naturally occurring amino acid or a non-naturally occurring amino acid. In other embodiments, the spacer contains more than one naturally occurring or non-naturally occurring amino acid. In specific embodiments, the spacer is Lys-, Gly-, Lys-Lys-Lys-, (α, ε-N)Lys, ε-N-Lys-Lys-Lys-Lys (SEQ ID NO: 72), or Lys-Lys-Lys-ε-N-Lys (SEQ ID NO: 73).

d. Specific Embodiments of the CGRP Peptide Immunogen Constructs

In certain embodiments, the CGRP peptide immunogen constructs can be represented by the following formulae:

$$(Th)_m\text{-}(A)_n\text{-}(\text{CGRP functional B epitope peptide})\text{-}X$$

or $$(\text{CGRP functional B epitope peptide})\text{-}(A)_n\text{-}(Th)_m\text{-}X$$

or $$(Th)_m\text{-}(A)_n\text{-}(CGRP \text{ functional B epitope peptide})\text{-}(A)_n\text{-}(Th)_m\text{-}X$$

wherein

Th is a heterologous T helper epitope;

A is a heterologous spacer;

(CGRP functional B epitope peptide) is a B cell epitope peptide having from 7 to 30 amino acid residues from CGRP that are involved in either receptor binding or receptor activation;

X is an α-COOH or α-CONH₂ of an amino acid;

m is from 1 to about 4; and n is from 0 to about 10.

The B cell epitope peptide can contain between about 7 to about 30 amino acids from any portion of the full-length CGRP protein represented by SEQ ID NOs: 1-3. In some embodiments, the B cell epitope has an amino acid sequence selected from any of SEQ ID NOs: 4-13 and 15-22, shown in Table 1. In certain embodiments, the B cell epitope peptide is from the CGRP receptor binding region located at the C-terminal/central region of the CGRP molecule R11-F37 (SEQ ID NO: 9), or fragments thereof (e.g. SEQ ID NOs: 5-8 and 15-22). In other embodiments, the B cell epitope peptide is from the CGRP receptor activation region around the cyclic C2-C7 loop such as A1-N25 (SEQ ID NO: 13) or fragments thereof (e.g. SEQ ID NOs: 4, 10-12, and 23-24).

The heterologous Th epitope in the CGRP peptide immunogen construct has an amino acid sequence selected from any of SEQ ID NOs: 74-115, and combinations thereof, shown in Table 2. In some embodiments, the CGRP peptide immunogen construct contains more than one Th epitope.

The optional heterologous spacer is selected from any of Lys-, Gly-, Lys-Lys-Lys-, (α, ε-N)Lys, Pro-Pro-Xaa-Pro-Xaa-Pro (SEQ ID NO: 71), ε-N-Lys-Lys-Lys-Lys (SEQ ID NO: 72), Lys-Lys-Lys-ε-N-Lys (SEQ ID NO: 73), and any combination thereof, where Xaa is any amino acid, but preferably aspartic acid. In specific embodiments, the heterologous spacer is ε-N-Lys-Lys-Lys-Lys (SEQ ID NO: 72) or Lys-Lys-Lys-ε-N-Lys (SEQ ID NO: 73).

In certain embodiments, the CGRP peptide immunogen construct has an amino acid sequence selected from any of SEQ ID NOs: 116-127 and 130-180 as shown in Table 3.

The CGRP peptide immunogen constructs comprising Th epitopes are produced simultaneously in a single solid-phase peptide synthesis in tandem with the CGRP fragment. Th epitopes also include immunological analogues of Th epitopes. Immunological Th analogues include immune-enhancing analogs, cross-reactive analogues and segments of any of these Th epitopes that are sufficient to enhance or stimulate an immune response to the CGRP B cell epitope peptide.

The Th epitope in the CGRP peptide immunogen construct can be covalently linked at either N- or C-terminal end of the CGRP B cell epitope peptide. In some embodiments, the Th epitope is covalently linked to the N-terminal end of the CGRP B cell epitope peptide. In other embodiments, the Th epitope is covalently linked to the C-terminal end of the CGRP B cell epitope peptide. In certain embodiments, more than one Th epitope is covalently linked to the CGRP B cell epitope peptide. When more than one Th epitope is linked to the CGRP B cell epitope peptide, each Th epitope can have the same amino acid sequence or different amino acid sequences. In addition, when more than one Th epitope is linked to the CGRP B cell epitope peptide, the Th epitopes can be arranged in any order. For example, the Th epitopes can be consecutively linked to the N-terminal end of the CGRP B cell epitope peptide, or consecutively linked to the C-terminal end of the CGRP B cell epitope peptide, or a Th epitope can be covalently linked to the N-terminal end of the CGRP B cell epitope peptide while a separate Th epitope is covalently linked to the C-terminal end of the CGRPB cell epitope peptide. There is no limitation in the arrangement of the Th epitopes in relation to the CGRP B cell epitope peptide.

In some embodiments, the Th epitope is covalently linked to the CGRP B cell epitope peptide directly. In other embodiments, the Th epitope is covalently linked to the CGRP fragment through a heterologous spacer.

e. Variants, Homologues, and Functional Analogues

Variants and analogs of the above immunogenic peptide constructs that induce and/or cross-react with antibodies to the preferred CGRP B cell epitope peptides can also be used. Analogs, including allelic, species, and induced variants, typically differ from naturally occurring peptides at one, two, or a few positions, often by virtue of conservative substitutions. Analogs typically exhibit at least 80 or 90% sequence identity with natural peptides. Some analogs also include unnatural amino acids or modifications of N- or C-terminal amino acids at one, two, or a few positions.

Variants that are functional analogues can have a conservative substitution in an amino acid position; a change in overall charge; a covalent attachment to another moiety; or amino acid additions, insertions, or deletions; and/or any combination thereof.

Conservative substitutions are when one amino acid residue is substituted for another amino acid residue with similar chemical properties. For example, the nonpolar (hydrophobic) amino acids include alanine, leucine, isoleucine, valine, proline, phenylalanine, tryptophan and methionine; the polar neutral amino acids include glycine, serine, threonine, cysteine, tyrosine, asparagine, and glutamine; the positively charged (basic) amino acids include arginine, lysine and histidine; and the negatively charged (acidic) amino acids include aspartic acid and glutamic acid.

In a particular embodiment, the functional analogue has at least 50% identity to the original amino acid sequence. In another embodiment, the functional analogue has at least 80% identity to the original amino acid sequence. In yet another embodiment, the functional analogue has at least 85% identity to the original amino acid sequence. In still another embodiment, the functional analogue has at least 90% identity to the original amino acid sequence.

Functional immunological analogues of the Th epitope peptides are also effective and included as part of the present invention. Functional immunological Th analogues can include conservative substitutions, additions, deletions and insertions of from one to about five amino acid residues in the Th epitope which do not essentially modify the Th-stimulating function of the Th epitope. The conservative substitutions, additions, and insertions can be accomplished with natural or non-natural amino acids, as described above for the CGRP B cell epitope peptide. Table 2 identifies another variation of a functional analogue for Th epitope peptide. In particular, SEQ ID NOs: 75 and 82 of MvF1 and MvF2 Th are functional analogues of SEQ ID NOs: 94 and 98 of MvF4 and MvF5 in that they differ in the amino acid frame by the deletion (SEQ ID NOs: 75 and 82) or the inclusion (SEQ ID NOs: 94 and 98) of two amino acids each at the N- and C-termini. The differences between these two series of analogous sequences would not affect the function of the Th epitopes contained within these sequences. Therefore, functional immunological Th analogues include several versions of the Th epitope derived from Measles Virus Fusion protein MvF1-4 Ths (SEQ ID NOs: 75, 82, 85, and 94) and from Hepatitis Surface protein HBsAg 1-3 Ths (SEQ ID NOs: 91, 97, and 99).

Compositions

The present disclosure also provides compositions comprising the disclosed CGRP immunogen peptide constructs.

a. Peptide Compositions

Compositions containing the disclosed CGRP peptide immunogen constructs can be in liquid or solid/lyophilized form. Liquid compositions can include water, buffers, solvents, salts, and/or any other acceptable reagent that does not alter the structural or functional properties of the CGRP peptide immunogen constructs. Peptide compositions can contain one or more of the disclosed CGRP peptide immunogen constructs.

b. Pharmaceutical Compositions

The present disclosure is also directed to pharmaceutical compositions containing the disclosed CGRP peptide immunogen constructs.

Pharmaceutical compositions can contain carriers and/or other additives in a pharmaceutically acceptable delivery system. Accordingly, pharmaceutical compositions can contain a pharmaceutically effective amount of an CGRP peptide immunogen construct together with pharmaceutically-acceptable carrier, adjuvant, and/or other excipients such as diluents, additives, stabilizing agents, preservatives, solubilizing agents, buffers, and the like.

Pharmaceutical compositions can contain one or more adjuvant that act(s) to accelerate, prolong, or enhance the immune response to the CGRP peptide immunogen constructs without having any specific antigenic effect itself. Adjuvants used in the pharmaceutical composition can include oils, oil emulsions, aluminum salts, calcium salts, immune stimulating complexes, bacterial and viral derivatives, virosomes, carbohydrates, cytokines, polymeric microparticles. In certain embodiments, the adjuvant can be selected from alum (potassium aluminum phosphate), aluminum phosphate (e.g. ADJU-PHOS®), aluminum hydroxide (e.g. ALHYDROGEL®), calcium phosphate, incomplete Freund's adjuvant (IFA), Freund's complete adjuvant, MF59, adjuvant 65, Lipovant, ISCOM, liposyn, saponin, squalene, L121, EmulsIL-6n®, monophosphoryl lipid A (MPL), Quil A, QS21, MONTANIDE® ISA 35, ISA 50V, ISA 50V2, ISA 51, ISA 206, ISA 720, liposomes, phospholipids, peptidoglycan, lipopolysaccharides (LPS), ASO1, ASO2, ASO3, ASO4, AF03, lipophilic phospholipid (lipid A), gamma inulin, algammulin, glucans, dextrans, glucomannans, galactomannans, levans, xylans, dimethyldioctadecylammonium bromide (DDA), as well as the other adjuvants and emulsifiers.

In some embodiments, the pharmaceutical composition contains MONTANIDE™ ISA 51 (an oil adjuvant composition comprised of vegetable oil and mannide oleate for production of water-in-oil emulsions), TWEEN® 80 (also known as: Polysorbate 80 or Polyoxyethylene (20) sorbitan monooleate), a CpG oligonucleotide, and/or any combination thereof. In other embodiments, the pharmaceutical composition is a water-in-oil-in-water (i.e. w/o/w) emulsion with EmulsIL-6n or EmulsIL-6n D as the adjuvant.

Pharmaceutical compositions can also include pharmaceutically acceptable additives or excipients. For example, pharmaceutical compositions can contain antioxidants, binders, buffers, bulking agents, carriers, chelating agents, coloring agents, diluents, disintegrants, emulsifying agents, fillers, gelling agents, pH buffering agents, preservatives, solubilizing agents, stabilizers, and the like.

Pharmaceutical compositions can be formulated as immediate release or for sustained release formulations. Additionally the pharmaceutical compositions can be formulated for induction of systemic, or localized mucosal, immunity through immunogen entrapment and co-administration with microparticles. Such delivery systems are readily determined by one of ordinary skill in the art.

Pharmaceutical compositions can be prepared as injectables, either as liquid solutions or suspensions. Liquid vehicles containing the CGRP peptide immunogen construct can also be prepared prior to injection. The pharmaceutical composition can be administered by any suitable mode of application, for example, i.d., i.v., i.p., i.m., intranasally, orally, subcutaneously, etc. and in any suitable delivery device. In certain embodiments, the pharmaceutical composition is formulated for intravenous, subcutaneous, intradermal, or intramuscular administration. Pharmaceutical compositions suitable for other modes of administration can also be prepared, including oral and intranasal applications.

Pharmaceutical compositions can also be formulated in a suitable dosage unit form. In some embodiments, the pharmaceutical composition contains from about 0.1 μg to about 1 mg of the CGRP peptide immunogen construct per kg body weight. Effective doses of the pharmaceutical compositions vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. When delivered in multiple doses, the pharmaceutical compositions may be conveniently divided into an appropriate amount per dosage unit form. The administered dosage will depend on the age, weight and general health of the subject as is well known in the therapeutic arts.

In some embodiments, the pharmaceutical composition contains more than one CGRP peptide immunogen construct. A pharmaceutical composition containing a mixture of more than one CGRP peptide immunogen construct to allow for synergistic enhancement of the immunoefficacy of the constructs. Pharmaceutical compositions containing more than one CGRP peptide immunogen construct can be more effective in a larger genetic population due to a broad MHC class II coverage thus provide an improved immune response to the CGRP peptide immunogen constructs.

In some embodiments, the pharmaceutical composition contains an CGRP peptide immunogen construct selected from SEQ ID NOs: 120-127 and 130-180 (Table 3), as well as homologues, analogues and/or combinations thereof.

In certain embodiments, CGRP peptide immunogen constructs (SEQ ID NOs: 161-163) with heterologous Th epitopes derived from MVF and HBsAg in a combinatorial form (SEQ ID NOs: 85, 91, 94, and 97) were mixed in an equimolar ratio for use in a formulation to allow for maximal coverage of a host population having a diverse genetic background.

Furthermore, the antibody response elicited by CGRP peptide immunogen construct (e.g. UBITh® 1 with SEQ ID NO: 108) was mostly (>90%) focused on the desired cross-reactivity against the B epitope peptide of CGRP without much, if any, directed to the heterologous Th epitopes employed for immunogenicity enhancement (Example 6, Table 10). This is in sharp contrast to the conventional protein such as KLH or other biological protein carriers used for such CGRP peptide immunogenicity enhancement.

In other embodiments, pharmaceutical compositions comprising a peptide composition of for example a mixture of the CGRP peptide immunogen constructs in contact with mineral salts including Alum gel (ALHYDROGEL) or Aluminum phosphate (ADJUPHOS) as adjuvant to form a suspension formulation was used for administration to hosts.

Pharmaceutical compositions containing an CGRP peptide immunogen construct can be used to elicit an immune response and produce antibodies in a host upon administration.

c. Immunostimulatory Complexes

The present disclosure is also directed to pharmaceutical compositions containing an CGRP peptide immunogen construct in the form of an immunostimulatory complex with a CpG oligonucleotide. Such immunostimulatory complexes are specifically adapted to act as an adjuvant and as a peptide immunogen stabilizer. The immunostimulatory complexes are in the form of a particulate, which can efficiently present the CGRP peptide immunogen to the cells of the immune system to produce an immune response. The immunostimulatory complexes may be formulated as a suspension for parenteral administration. The immunostimulatory complexes may also be formulated in the form of water in oil (w/o) emulsions, as a suspension in combination with a mineral salt or with an in-situ gelling polymer for the efficient delivery of the CGRP peptide immunogen construct to the cells of the immune system of a host following parenteral administration.

The stabilized immunostimulatory complex can be formed by complexing an CGRP peptide immunogen construct with an anionic molecule, oligonucleotide, polynucleotide, or combinations thereof via electrostatic association. The stabilized immunostimulatory complex may be incorporated into a pharmaceutical composition as an immunogen delivery system.

In certain embodiments, the CGRP peptide immunogen construct is designed to contain a cationic portion that is positively charged at a pH in the range of 5.0 to 8.0. The net charge on the cationic portion of the CGRP peptide immunogen construct, or mixture of constructs, is calculated by assigning a +1 charge for each lysine (K), arginine (R) or histidine (H), a −1 charge for each aspartic acid (D) or glutamic acid (E) and a charge of 0 for the other amino acid within the sequence. The charges are summed within the cationic portion of the CGRP peptide immunogen construct and expressed as the net average charge. A suitable peptide immunogen has a cationic portion with a net average positive charge of +1. Preferably, the peptide immunogen has a net positive charge in the range that is larger than +2. In some embodiments, the cationic portion of the CGRP peptide immunogen construct is the heterologous spacer. In certain embodiments, the cationic portion of the CGRP peptide immunogen construct has a charge of +4 when the spacer sequence is (α, ε-N)Lys, (α,ε-N)-Lys-Lys-Lys-Lys (SEQ ID NO: 72), or Lys-Lys-Lys-ε-N-Lys (SEQ ID NO: 73).

An "anionic molecule" as described herein refers to any molecule that is negatively charged at a pH in the range of 5.0-8.0. In certain embodiments, the anionic molecule is an oligomer or polymer. The net negative charge on the oligomer or polymer is calculated by assigning a −1 charge for each phosphodiester or phosphorothioate group in the oligomer. A suitable anionic oligonucleotide is a single-stranded DNA molecule with 8 to 64 nucleotide bases, with the number of repeats of the CpG motif in the range of 1 to 10. Preferably, the CpG immunostimulatory single-stranded DNA molecules contain 18-48 nucleotide bases, with the number of repeats of CpG motif in the range of 3 to 8.

More preferably the anionic oligonucleotide is represented by the formula: 5' $X^1CGX^2$ 3' wherein C and G are unmethylated; and $X^1$ is selected from the group consisting of A (adenine), G (guanine) and T (thymine); and $X^2$ is C (cytosine) or T (thymine). Or, the anionic oligonucleotide is represented by the formula: 5' $(X^3)_2CG(X^4)_2$ 3' wherein C and G are unmethylated; and $X^3$ is selected from the group consisting of A, T or G; and $X^4$ is C or T. In specific embodiments, the CpG oligonucleotide has the sequence of CpG1: 5' TCg TCg TTT TgT CgT TTT gTC gTT TTg TCg TT 3' (fully phosphorothioated) (SEQ ID NO: 182), CpG2: 5' Phosphate TCg TCg TTT TgT CgT TTT gTC gTT 3' (fully phosphorothioated) (SEQ ID NO: 183), or CpG3 5' TCg TCg TTT TgT CgT TTT gTC gTT 3' (fully phosphorothioated) (SEQ ID NO: 184).

The resulting immunostimulatory complex is in the form of particles with a size typically in the range from 1-50 microns and is a function of many factors including the relative charge stoichiometry and molecular weight of the interacting species. The particulated immunostimulatory complex has the advantage of providing adjuvantation and upregulation of specific immune responses in vivo. Additionally, the stabilized immunostimulatory complex is suitable for preparing pharmaceutical compositions by various processes including water-in-oil emulsions, mineral salt suspensions and polymeric gels.

The present disclosure is also directed to pharmaceutical compositions, including formulations, for the prevention and/or treatment of migraine. In some embodiments, pharmaceutical compositions comprising a stabilized immunostimulatory complex, which is formed through mixing a CpG oligomer with a peptide composition containing a mixture of the CGRP peptide immunogen constructs (e.g., SEQ ID NOs: 120-127 and 130-180) through electrostatic association, to further enhance the immunogenicity of the CGRP peptide immunogen constructs and elicit antibodies that are cross-reactive with the CGRP proteins of SEQ ID NOs: 1-3 that are directed at the CGRP receptor binding or receptor activation region (Example 6).

In yet other embodiments, pharmaceutical compositions contain a mixture of the CGRP peptide immunogen constructs (e.g., any combination of SEQ ID NOs: 120-127 and 130-180) in the form of a stabilized immunostimulatory complex with CpG oligomers that are, optionally, mixed with mineral salts, including Alum gel (ALHYDROGEL) or Aluminum phosphate (ADJUPHOS) as an adjuvant with high safety factor, to form a suspension formulation for administration to hosts.

Antibodies

The present disclosure also provides antibodies elicited by the CGRP peptide immunogen constructs.

The present disclosure provides CGRP peptide immunogen constructs and formulations thereof, cost effective in manufacturing, optimal in their design that are capable of eliciting high titer antibodies targeting the CGRP receptor binding or receptor activation region of the CGRP molecule (SEQ ID NOs: 4-13 and 15-24) that is capable of breaking the immune tolerance against self-protein CGRP with a high responder rate in immunized hosts. The antibodies generated by the CGRP peptide immunogen constructs have high affinity towards the CGRP receptor binding or activation region.

In some embodiments, CGRP peptide immunogen constructs for eliciting antibodies comprise a hybrid of a CGRP peptide targeting the CGRP receptor binding or receptor activation region of the CGRP molecule (SEQ ID NOs: 4-13 and 15-24) linked to a heterologous Th epitope derived from pathogenic proteins such as Measles Virus Fusion (MVF) protein and others (SEQ ID NOs: 74-115) through an optional spacer. The B epitope and Th epitope peptide of the CGRP peptide immunogen constructs act together to stimulate the generation of highly specific antibodies cross-reactive with the CGRP receptor binding or activation region of the CGRP protein (SEQ ID NO: 1-3).

Traditional methods for immunopotentiating a peptide, such as through chemical coupling to a carrier protein, for example, Keyhole Limpet Hemocyanin (KLH) or other carrier proteins such as Diphtheria toxoid (DT) and Tetanus Toxoid (TT) proteins, typically result in the generation of a large amount of antibodies directed against the carrier protein. Thus, a major deficiency of such peptide-carrier protein compositions is that most (>90%) of antibodies generated by the immunogen are the non-functional antibodies directed against the carrier protein KLH, DT or TT, which can lead to epitopic suppression.

Unlike the traditional method for immunopotentiating a peptide, the antibodies generated by the disclosed CGRP peptide immunogen constructs (e.g. SEQ ID NOs: 116-127 and 130-180) bind with highly specificity to the CGRP B epitope peptide (SEQ ID NO:4-13 and 15-24) with little, if any, antibodies directed against the heterologous Th epitope (e.g., SEQ ID NOs: 74-115) or optional heterologous spacer.

Methods

The present disclosure is also directed to methods for making and using the CGRP peptide immunogen constructs, compositions, and pharmaceutical compositions.

a. Methods for Manufacturing the CGRP Peptide Immunogen Construct

The CGRP peptide immunogen constructs of this disclosure can be made by chemical synthesis methods well known to the ordinarily skilled artisan (see, e.g., Fields, et al., 1992). The CGRP peptide immunogen constructs can be synthesized using the automated Merrifield techniques of solid phase synthesis with the $\alpha$-NH$_2$ protected by either t-Boc or F-moc chemistry using side chain protected amino acids on, for example, an Applied Biosystems Peptide Synthesizer Model 430A or 431. Preparation of CGRP peptide immunogen constructs comprising combinatorial library peptides for Th epitopes can be accomplished by providing a mixture of alternative amino acids for coupling at a given variable position.

After complete assembly of the desired CGRP peptide immunogen construct, the resin can be treated according to standard procedures to cleave the peptide from the resin and the functional groups on the amino acid side chains can be deblocked. The free peptide can be purified by HPLC and characterized biochemically, for example, by amino acid analysis or by sequencing. Purification and characterization methods for peptides are well known to one of ordinary skill in the art.

The quality of peptides produced by this chemical process can be controlled and defined and, as a result, reproducibility of CGRP peptide immunogen constructs, immunogenicity, and yield can be assured. Detailed description of the manufacturing of the CGRP peptide immunogen construct through solid phase peptide synthesis is shown in Example 1.

The range in structural variability that allows for retention of an intended immunological activity has been found to be far more accommodating than the range in structural variability allowed for retention of a specific drug activity by a small molecule drug or the desired activities and undesired toxicities found in large molecules that are co-produced with biologically-derived drugs.

Thus, peptide analogues, either intentionally designed or inevitably produced by errors of the synthetic process as a mixture of deletion sequence byproducts that have chromatographic and immunologic properties similar to the intended peptide, are frequently as effective as a purified preparation of the desired peptide. Designed analogues and unintended analogue mixtures are effective as long as a discerning QC procedure is developed to monitor both the manufacturing process and the product evaluation process so as to guarantee the reproducibility and efficacy of the final product employing these peptides.

The CGRP peptide immunogen constructs can also be made using recombinant DNA technology including nucleic acid molecules, vectors, and/or host cells. As such, nucleic acid molecules encoding the CGRP peptide immunogen construct and immunologically functional analogues thereof are also encompassed by the present disclosure as part of the present invention. Similarly, vectors, including expression vectors, comprising nucleic acid molecules as well as host cells containing the vectors are also encompassed by the present disclosure as part of the present invention.

Various exemplary embodiments also encompass methods of producing the CGRP peptide immunogen construct and immunologically functional analogues thereof. For example, methods can include a step of incubating a host cell containing an expression vector containing a nucleic acid molecule encoding an CGRP peptide immunogen construct and/or immunologically functional analogue thereof under such conditions where the peptide and/or analogue is expressed. The longer synthetic peptide immunogens can be synthesized by well-known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

b. Methods for the Manufacturing of Immunostimulatory Complexes

Various exemplary embodiments also encompass methods of producing the Immunostimulatory complexes comprising CGRP peptide immunogen constructs and CpG oligodeoxynucleotide (ODN) molecule. Stabilized immunostimulatory complexes (ISC) are derived from a cationic portion of the CGRP peptide immunogen construct and a polyanionic CpG ODN molecule. The self-assembling system is driven by electrostatic neutralization of charge. Stoichiometry of the molar charge ratio of cationic portion of the CGRP peptide immunogen construct to anionic oligomer determines extent of association. The non-covalent electrostatic association of CGRP peptide immunogen construct and CpG ODN is a completely reproducible process. The peptide/CpG ODN immunostimulatory complex aggregates, which facilitate presentation to the "professional" antigen presenting cells (APC) of the immune system thus further enhancing the immunogenicity of the complexes. These complexes are easily characterized for quality control during manufacturing. The peptide/CpG ISC are well tolerated in vivo. This novel particulate system comprising CpG ODN and CGRP peptide immunogen constructs was designed to take advantage of the generalized B cell mitogenicity associated with CpG ODN use, yet promote balanced Th-1/Th-2 type responses.

The CpG ODN in the disclosed pharmaceutical compositions is 100% bound to immunogen in a process mediated by electrostatic neutralization of opposing charge, resulting in the formation of micron-sized particulates. The particulate form allows for a significantly reduced dosage of CpG from the conventional use of CpG adjuvants, less potential for adverse innate immune responses, and facilitates alternative immunogen processing pathways including antigen presenting cells (APC). Consequently, such formulations are novel conceptually and offer potential advantages by promoting the stimulation of immune responses by alternative mechanisms.

c. Methods for the Manufacturing of Pharmaceutical Compositions

Various exemplary embodiments also encompass pharmaceutical compositions containing CGRP peptide immunogen constructs. In certain embodiments, the pharmaceutical compositions employ water in oil emulsions and in suspension with mineral salts.

In order for a pharmaceutical composition to be used by a large population, safety becomes another important factor for consideration. Despite there has been use of water-in-oil emulsions in many clinical trials, Alum remains the major adjuvant for use in formulations due to its safety. Alum or its mineral salts Aluminum phosphate (ADJUPHOS) are, therefore, frequently used as adjuvants in preparation for clinical applications.

Other adjuvants and immunostimulating agents include 3 De-O-acylated monophosphoryl lipid A (MPL) or 3-DMP, polymeric or monomeric amino acids, such as polyglutamic acid or polylysine. Such adjuvants can be used with or without other specific immunostimulating agents, such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2' dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide™), or other bacterial cell wall components. Oil-in-water emulsions include MF59 (see WO 90/14837 to Van Nest et al., which is hereby incorporated by reference in its entirety), containing 5% Squalene, 0.5% TWEEN 80, and 0.5% Span 85 (optionally containing various amounts of MTP-PE) formulated into submicron particles using a microfluidizer; SAF, containing 10% Squalene, 0.4% TWEEN 80, 5% pluronic-blocked polymer L121, and thr-MDP, either microfluidized into a submicron emulsion or vortexed to generate a larger particle size emulsion; and the Ribi™ adjuvant system (RAS) (Ribi ImmunoChem, Hamilton, Mont.) containing 2% squalene, 0.2% TWEEN 80, and one or more bacterial cell wall components selected from the group consisting of monophosphoryllipid A (MPL), trehalose dimycolate (TDM), and cell wall skeleton (CWS), preferably MPL+ CWS (Detox™). Other adjuvants include Complete Freund's Adjuvant (CFA), Incomplete Freund's Adjuvant (IFA), and cytokines, such as interleukins (IL-1, IL-2, and IL-12), macrophage colony stimulating factor (M-CSF), and tumor necrosis factor (TNF-α).

The choice of an adjuvant depends on the stability of the immunogenic formulation containing the adjuvant, the route of administration, the dosing schedule, the efficacy of the adjuvant for the species being immunized, and, in humans, a pharmaceutically acceptable adjuvant is one that has been approved or is approvable for human administration by pertinent regulatory bodies. For example, alum, MPL or Incomplete Freund's adjuvant (Chang, et al., 1998), which is hereby incorporated by reference in its entirety) alone or optionally all combinations thereof are suitable for human administration.

The compositions can include pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, non-immunogenic stabilizers, and the like.

Pharmaceutical compositions can also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes). Additionally, these carriers can function as immunostimulating agents (i.e., adjuvants).

The pharmaceutical compositions of the present invention can further include a suitable delivery vehicle. Suitable delivery vehicles include, but are not limited to viruses, bacteria, biodegradable microspheres, microparticles, nanoparticles, liposomes, collagen minipellets, and cochleates.

d. Methods of Using Pharmaceutical Compositions

The present disclosure also includes methods of using pharmaceutical compositions containing CGRP peptide immunogen constructs.

In certain embodiments, the pharmaceutical compositions containing CGRP peptide immunogen constructs can be used for the treatment of migraine.

In some embodiments, the methods comprise administering a pharmaceutical composition comprising a pharmacologically effective amount of an CGRP peptide immunogen construct to a host in need thereof. In certain embodiments, the methods comprise administering a pharmaceutical composition comprising a pharmacologically effective amount of an CGRP peptide immunogen construct to a warm-blooded animal (e.g., humans, Cynomolgus macaques, mice) to elicit highly specific antibodies cross-reactive with the human CGRP protein (SEQ ID NO: 1), or CGRP proteins from other species (e.g., SEQ ID NOs: 2 and 3).

In certain embodiments, the pharmaceutical compositions containing CGRP peptide immunogen constructs can be used to treat migraine as shown in in vivo capsaicin induced dorsal blood flow model.

e. In Vitro Functional Assays and In Vivo Proof of Concept Studies

Antibodies elicited in immunized hosts by the CGRP peptide immunogen constructs can be used in in vitro functional assays. These functional assays include, but are not limited to:

(1) in vitro binding to CGRP protein (SEQ ID NOs: 1-3);
(2) inhibition in vitro of CGRP binding to its receptor;
(3) inhibition in vitro of intracellular cAMP elevation;

(4) inhibition in vivo of capsaicin induced dorsal blood flow model in mice.

Specific Embodiments (1) A CGRP peptide immunogen construct having about 30 or more amino acids, represented by the formulae:

$(Th)_m$-$(A)_n$-(CGRP functional B epitope peptide)-X or (CGRP functional B epitope peptide)-$(A)_n$-$(Th)_m$-X or $(Th)_m$-$(A)_n$-(CGRP functional B epitope peptide)-(A)$_n$-$(Th)_m$-X wherein Th is a heterologous T helper epitope;

A is a heterologous spacer;

(CGRP functional B epitope peptide) is a B cell epitope peptide having from 7 to about 30 amino acid residues derived from CGRP receptor binding or activation region with SEQ ID NOs: 4-13, 15-24) of CGRP (SEQ ID NOs: 1-3) as shown in Table 1;

X is an $\alpha$-COOH or $\alpha$-CONH$_2$ of an amino acid;

m is from 1 to about 4; and n is from 0 to about 10.

(2) The CGRP peptide immunogen construct according to (1), wherein the CGRP receptor binding or activation region is selected from the group consisting of SEQ ID NOs: 4-13 and 15-24.

(3) The CGRP peptide immunogen construct according to any of (1) or (2), wherein the Th epitope is selected from the group consisting of SEQ ID NOs: 74-115.

(4) The CGRP peptide immunogen construct according to (1), wherein the peptide immunogen construct is selected from the group consisting of SEQ ID NOs: 120-127 and 130-180.

(5) An CGRP peptide immunogen construct comprising:

a. a B cell epitope comprising from about 7 to about 30 amino acid residues from the CGRP sequence of SEQ ID NOs: 1 to 3;

b. a T helper epitope comprising an amino acid sequence selected from the group consisting of SEQ ID NOs: 74-115, and any combination thereof; and c. an optional heterologous spacer selected from the group consisting of an amino acid, Lys-, Gly-, Lys-Lys-Lys-, ($\alpha$, $\varepsilon$-N)Lys, $\varepsilon$-N-Lys-Lys-Lys-Lys (SEQ ID NO: 72), Lys-Lys-Lys-8-N-Lys (SEQ ID NO: 73), and Pro-Pro-Xaa-Pro-Xaa-Pro (SEQ ID NO: 71), and any combination thereof, wherein the B cell epitope is covalently linked to the T helper epitope directly or through the optional heterologous spacer.

(6) The CGRP peptide immunogen construct of (5), wherein the B cell epitope is selected from the group consisting of SEQ ID NOs: 4-13 and 15-24.

(7) The CGRP peptide immunogen construct of (5), wherein the T helper epitope is selected from the group consisting of SEQ ID NOs: 78, 77, 80-82, 85, 91, 94, 97, 98-99, 106-109, 112, and any combination thereof.

(8) The CGRP peptide immunogen construct of (5), wherein the optional heterologous spacer is ($\alpha$, $\varepsilon$-N)Lys, $\varepsilon$-N-Lys-Lys-Lys-Lys (SEQ ID NO: 72), Lys-Lys-Lys-$\varepsilon$-N-Lys (SEQ ID NO: 73), or Pro-Pro-Xaa-Pro-Xaa-Pro (SEQ ID NO: 71), where Xaa is any amino acid.

(9) The CGRP peptide immunogen construct of (5), wherein the T helper epitope is covalently linked to the amino terminus of the B cell epitope.

(10) The CGRP peptide immunogen construct of (5), wherein the T helper epitope is covalently linked to the amino terminus of the B cell epitope through the optional heterologous spacer.

(11) A composition comprising an CGRP peptide immunogen construct according to (1).

(12) A pharmaceutical composition comprising:

a. a peptide immunogen construct according to (1); and b. a pharmaceutically acceptable delivery vehicle and/or adjuvant.

(13) The pharmaceutical composition of (12), wherein a. the CGRP functional B epitope peptide is selected from the group consisting of SEQ ID NOs: 4-13 and 15-24;

b. the Th epitope is selected from the group consisting of SEQ ID NOs: 74-115; and c. the heterologous spacer is selected from the group consisting of an amino acid, Lys-, Gly-, Lys-Lys-Lys-, ($\alpha$, $\varepsilon$-N)Lys, $\varepsilon$-N-Lys-Lys-Lys-Lys (SEQ ID NO: 72), Lys-Lys-Lys-$\varepsilon$-N-Lys (SEQ ID NO: 73), and Pro-Pro-Xaa-Pro-Xaa-Pro (SEQ ID NO: 71), and any combination thereof; and wherein the CGRP peptide immunogen construct is mixed with an CpG oligodeoxynucleotide (ODN) to form a stabilized immunostimulatory complex.

(14) The pharmaceutical composition of (12), wherein a. the CGRP peptide immunogen construct is selected from the group consisting of SEQ ID NOs: 120-127 and 130-180; and wherein the CGRP peptide immunogen construct is mixed with an CpG oligodeoxynucleotide (ODN) to form a stabilized immunostimulatory complex.

(15) A method for generating antibodies against CGRP in an animal comprising administering the pharmaceutical composition according to (12) to the animal.

(16) An isolated antibody or epitope-binding fragment thereof that specifically binds to the CGRP receptor binding or activation region of SEQ ID NOs: 4-13 and 15-24.

(17) The isolated antibody or epitope-binding fragment thereof according to (16) bound to the CGRP peptide immunogen construct.

(18) A composition comprising the isolated antibody or epitope-binding fragment thereof according to (16).

(19) A method of preventing and/or treating migraine in an animal comprising administering the pharmaceutical composition of (12) to the animal.

Example 1

Synthesis of CGRP Related Peptides and Preparation of Formulations Thereof a. Synthesis of CGRP Related Peptides Methods for synthesizing CGRP related peptides that were included in the development effort of CGRP peptide immunogen constructs are described. The peptides were synthesized in small-scale amounts that are useful for serological assays, laboratory pilot and field studies, as well as large-scale (kilogram) amounts, which are useful for industrial/commercial production of pharmaceutical compositions. A large repertoire of CGRP related antigenic peptides having sequences with lengths from approximately 10 to 70 amino acids were designed for epitope mapping and for the screening and selection of the most optimal peptide immunogen constructs for use in an efficacious CGRP targeted therapeutic vaccine.

Representative full-length CGRP of human, mouse, rat and macaque species (SEQ ID NOs: 1-3), CGRP peptide fragments, and 10-mer peptide employed for epitope mapping in various serological assays are listed in Table 1 (SEQ ID NOs: 1-70).

Selected CGRP B cell epitope peptides were made into CGRP peptide immunogen constructs by synthetically linking to a carefully designed helper T cell (Th) epitope peptide which was derived from pathogen proteins including Measles Virus Fusion protein (MVF), Hepatitis B Surface Antigen protein (HBsAg), peptide influenza, *Clostridium tetani*, and Epstein-Barr virus (EBV) identified in Table 2 (SEQ ID NOs: 74-115). The Th epitope peptides were used either in a single sequence (SEQ ID NOs: 74-84, 86-90, 92-93, 95-96, 98-115) or a combinatorial library (SEQ ID NOs: 85, 91, 94, and 97) to enhance the immunogenicity of their respective CGRP peptide immunogen constructs.

Representative CGRP peptide immunogen constructs selected from hundreds of peptide constructs are identified in Table 3 (SEQ ID NOs: 116-180). All peptides used for immunogenicity studies or related serological tests for detection and/or measurement of anti-CGRP antibodies were synthesized on a small scale using F-moc chemistry by peptide synthesizers of Applied BioSystems Models 430A, 431 and/or 433. Each peptide was produced by an independent synthesis on a solid-phase support, with F-moc protection at the N-terminus and side chain protecting groups of trifunctional amino acids. Completed peptides were cleaved from the solid support and side chain protecting groups were removed by 90% Trifluoroacetic acid (TFA). Synthetic peptide preparations were evaluated by Matrix-Assisted Laser Desorption/Ionization-Time-Of-Flight (MALDI-TOF) Mass Spectrometry to ensure correct amino acid content. Each synthetic peptide was also evaluated by Reverse Phase HPLC (RP-HPLC) to confirm the synthesis profile and concentration of the preparation. Despite rigorous control of the synthesis process (including stepwise monitoring the coupling efficiency), peptide analogues were also produced due to unintended events during elongation cycles, including amino acid insertion, deletion, substitution, and premature termination. Thus, synthesized preparations typically included multiple peptide analogues along with the targeted peptide.

Despite the inclusion of such unintended peptide analogues, the resulting synthesized peptide preparations were nevertheless suitable for use in immunological applications including immunodiagnosis (as antibody capture antigens) and pharmaceutical compositions (as peptide immunogens). Typically, such peptide analogues, either intentionally designed or generated through synthetic process as a mixture of byproducts, are frequently as effective as a purified preparation of the desired peptide, as long as a discerning QC procedure is developed to monitor both the manufacturing process and the product evaluation process to guarantee the reproducibility and efficacy of the final product employing these peptides. Large scale peptide syntheses in the multi-hundred to kilo gram quantities were conducted on a customized automated peptide synthesizer UBI2003 or the like at 15 mmole to 150 mmole scale.

For active ingredients used in the final pharmaceutical composition for clinical trials, CGRP related peptide immunogen constructs were purified by preparative RP-HPLC under a shallow elution gradient and characterized by MALDI-TOF mass spectrometry, amino acid analysis and RP-HPLC for purity and identity.

b. Preparation of Compositions Containing CGRP Peptide Immunogen Constructs

Formulations employing water in oil emulsions and in suspension with mineral salts were prepared. In order for a pharmaceutical composition designed to be used by a large population, safety becomes another important factor for consideration. Despite the fact that water-in-oil emulsions have been used in humans as pharmaceutical compositions in many clinical trials, Alum remains the major adjuvant for use in pharmaceutical composition due to its safety. Alum or its mineral salts ADJUPHOS (Aluminum phosphate) are therefore frequently used as adjuvants in preparation for clinical applications.

Briefly, the formulations specified in each of the study groups described below generally contained all types of CGRP designer peptide immunogen constructs. Over 200 designer CGRP peptide immunogen constructs were carefully evaluated in guinea pigs for their relative immunogenicity with the corresponding CGRP peptide representative of the immunogen's B epitope peptides. Epitope mapping and serological cross-reactivities were analyzed amongst the varying homologous peptides by ELISA assays using plates coated with peptides selected from the list with SEQ ID NOs: 1-70.

The CGRP peptide immunogen constructs at varying amounts were prepared in a water-in-oil emulsion with Seppic MONTANIDE™ ISA 51 as the approved oil for human use, or mixed with mineral salts ADJUPHOS (Aluminum phosphate) or ALHYDROGEL (Alum) as specified. Compositions were typically prepared by dissolving the CGRP peptide immunogen constructs in water at about 20 to 2000 µg/mL and formulated with MONTANIDE™ ISA 51 into water-in-oil emulsions (1:1 in volume) or with mineral salts ADJUPHOS or ALHYDROGEL (Alum) (1:1 in volume). The compositions were kept at room temperature for about 30 min and mixed by vortex for about 10 to 15 seconds prior to immunization. Animals were immunized with 2 to 3 doses of a specific composition, which were administered at time 0 (prime) and 3 week post initial immunization (wpi) (boost), optionally 5 or 6 wpi for a second boost, by intramuscular route. Sera from the immunized animals were then tested with selected B epitope peptide(s) to evaluate the immunogenicity of the various CGRP peptide immunogen constructs present in the formulation and for the corresponding sera's cross-reactivity with CGRP proteins. Those CGRP peptide immunogen constructs with potent immunogenicity found in the initial screening in guinea pigs were further tested in in vitro assays for their corresponding sera's functional properties. The selected candidate CGRP peptide immunogen constructs were then prepared in water-in-oil emulsion, mineral salts, and alum-based formulations for dosing regimens over a specified period as dictated by the immunizations protocols.

Only the most promising CGRP peptide immunogen constructs were further assessed extensively prior to being incorporated into final formulations for immunogenicity, duration, toxicity and efficacy studies in GLP guided preclinical studies in preparation for submission of an Investigational New Drug application followed by clinical trials in patients suffering from migraine.

The following examples serve to illustrate the present invention and are not to be used to limit the scope of the invention.

Example 2

Serological Assays and Reagents

Serological assays and reagents for evaluating functional immunogenicity of the CGRP peptide immunogen constructs and formulations thereof are described in details below.

a. CGRP or CGRP B Epitope Peptide Based ELISA Tests for Immunogenicity and Antibody Specificity Analysis ELISA assays for evaluating immune serum samples described in the following Examples were developed and described below. The wells of 96-well plates were coated individually for 1 hour at 37° C. with 100 µL of CGRP or CGRP B epitope peptides etc. (SEQ ID NOs: 1 to 70), at 2 µg/mL (unless noted otherwise), in 10 mM $NaHCO_3$ buffer, pH 9.5 (unless noted otherwise).

The CGRP or CGRP B epitope peptide-coated wells were incubated with 250 µL of 3% by weight gelatin in PBS at 37° C. for 1 hour to block non-specific protein binding sites, followed by three washes with PBS containing 0.05% by volume TWEEN® 20 and dried. Sera to be analyzed were diluted 1:20 (unless noted otherwise) with PBS containing 20% by volume normal goat serum, 1% by weight gelatin and 0.05% by volume TWEEN® 20. One hundred micro-liters (100 µL) of the diluted specimens (e.g., serum, plasma) were added to each of the wells and allowed to react for 60 minutes at 37° C. The wells were then washed six times with 0.05% by volume TWEEN® 20 in PBS in order to remove unbound antibodies. Horseradish peroxidase (HRP)-conju-gated species (e.g., guinea pig or rat) specific goat poly-clonal anti-IgG antibody or Protein A/G were used as a labeled tracer to bind with the antibody/peptide antigen complex formed in positive wells. One hundred microliters of the HRP-labeled detection reagent, at a pre-titered opti-mal dilution and in 1% by volume normal goat serum with 0.05% by volume TWEEN® 20 in PBS, was added to each well and incubated at 37° C. for another 30 minutes. The wells were washed six times with 0.05% by volume TWEEN® 20 in PBS to remove unbound antibody and reacted with 100 µL of the substrate mixture containing 0.04% by weight 3', 3', 5', 5'-Tetramethylbenzidine (TMB) and 0.12% by volume hydrogen peroxide in sodium citrate buffer for another 15 minutes. This substrate mixture was used to detect the peroxidase label by forming a colored product. Reactions were stopped by the addition of 100 µL of 1.0M $H_2SO_4$ and absorbance at 450 nm ($A_{450}$) deter-mined. For the determination of antibody titers of the vaccinated animals that received the various peptide vaccine formulations, a 10-fold serial dilutions of sera from 1:100 to 1:10,000 or a 4-fold serial dilutions of sera from 1:100 to 1:4.19×10⁸ were tested, and the titer of a tested serum, expressed as $Log_{10}$, was calculated by linear regression analysis of the $A_{450}$ with the cutoff $A_{450}$ set at 0.5.

b. Assessment of Antibody Reactivity Towards Th Peptide by Th Peptide Based ELISA Tests The wells of 96-well ELISA plates were coated individu-ally for 1 hour at 37° C. with 100 µL of Th peptide at 2 µg/mL (unless noted otherwise), in 10 mM $NaHCO_3$ buffer, pH 9.5 (unless noted otherwise) in similar ELISA method and performed as described above. For the determination of antibody titers of the vaccinated animals that received the various CGRP peptide vaccine formulations, 10-fold serial dilutions of sera from 1:100 to 1:10,000 were tested, and the titer of a tested serum, expressed as $Log_{10}$, was calculated by linear regression analysis of the $A_{450}$ with the cutoff $A_{450}$ set at 0.5.

c. Fine Specificity Analyses of a Target CGRP B Cell Epitope Peptide Determined by Epitope Mapping Through B Cell Epitope Cluster 10-Mer Peptide-Based ELISA Tests Fine specificity analyses of anti-CGRP antibodies from hosts immunized with CGRP peptide immunogen constructs were determined by epitope mapping using B cell epitope cluster 10mer peptide-based ELISA tests. Briefly, the wells of 96-well plates were coated with individual CGRP or related 10-mer peptides (SEQ ID NOs: 26-70) at 0.5 µg per 0.1 mL per well and then 100 µL serum samples (1:100 dilution in PBS) were incubated in 10-mer plate wells in duplicate following the steps of the antibody ELISA method described above. The target B cell epitope related fine specificity analyses of anti-CGRP antibodies from immu-nized hosts were tested with corresponding CGRP peptide, or with non-relevant control peptide for specificity confir-mation.

d. Immunogenicity Evaluation

Preimmune and immune serum samples from animal or human subjects were collected according to experimental vaccination protocols and heated at 56° C. for 30 minutes to inactivate serum complement factors. Following the admin-istration of the vaccine formulations, blood samples were obtained according to protocols and their immunogenicity against specific target site(s) were evaluated by correspond-ing CGRP B cell epitope peptide-based ELISA tests. Serially diluted sera were tested and positive titers were expressed as $Log_{10}$ of the reciprocal dilution. Immunogenicity of a par-ticular vaccine formulation is assessed for its ability to elicit high titer antibody response directed against the desired epitope specificity within the target antigen and high cross-reactivities with CGRP proteins, while maintaining a low to negligible antibody reactivity towards the "Helper T cell epitopes" employed to provide enhancement of the desired B cell responses.

Example 3

Assessment of Functional Properties of Antibodies Elicited by the CGRP Peptide Immunogen Constructs and Formu-lations Thereof in an In Vitro Assay for Intracellular Camp Production Immune sera or purified anti-CGRP antibodies in immu-nized vaccines were further tested for their ability to sup-press the CGRP-induced intracellular AMP production.

a. Antibody Purification

All antibody purification procedures were followed according to manual of antibody purification kit (Thermo fisher, Cat no. 89953). The respective concentrations of IgG purification for each of the groups were carefully calibrated for use in in vitro assay.

b. Cell Preparation and Maintenance

Cell line L6 (ATCC® CRL-1458™) was purchased from ATCC. The base medium for this cell line is ATCC-formu-lated Dulbecco's Modified Eagle's Medium, Catalog No. 30-2002. Fetal bovine serum was added to a final concen-tration of 10% to make a complete growth medium. Atmo-sphere: air, 95%; carbon dioxide ($CO_2$), 5% Temperature: 37° C.

c. Treatment of CGRP with/without IgGs

Anti-CGRP IgGs were further screened for neutralization activity in vitro using cell based CAMP activation assay. All procedures were done in 384 well round bottom low volume plate (Mediomics, LLC Cat. No. 163301). Five micro liters of rat α-CGRP (final concentration 10 nM) in the presence of an anti-CGRP IgG (final concentration 1-20 µg/ml), was incubated at room temperature for 30 minutes. Then five microliters of 5000 rat L6 muscle cells in 1XKRB-IBMS buffer were added. The plate was incubated at room temperature for 30 minutes.

d. Cell Based CGRP Neutralization Test (cAMP Level Detection)

After the incubation, cAMP activation was performed using Mediomics Bridge-It cAMP all in one Fluorescence Assay (Mediomics, Cat. No. 122938/122939) following manufacture's instruction. 10 μl of the CAMP all in one assay solution was added to each of the wells and mixed by pipetting up and down to lyse the cells and start the CAMP assay. The plate was covered to avoid evaporation and exposure to light. The plate was incubated at room temperature for 30 minutes with fluorescence intensity (excitation 485 nm, emission 540 nm) read by a fluorescence reader (SpectraMax i3x Multi-Mode Microplate Reader). Data are recorded in percentage. 0% represents L6 cell alone and 100% stands for CGRP treated L6 cell.

Example 4

Animals Used in Safety, Immunogenicity, Toxicity and Efficacy Studies
a. Guinea Pigs:

Immunogenicity studies were conducted in mature, naïve, adult male and female Duncan-Hartley guinea pigs (300-350 g/BW). The experiments utilized at least 3 Guinea pigs per group. Protocols involving Duncan-Hartley guinea pigs (8-12 weeks of age; Covance Research Laboratories, Denver, PA, USA) were performed under approved IACUC applications at a contracted animal facility under UBI sponsorship.
b. Cynomolgus Macaques:

Immunogenicity and repeated dose toxicity studies in adult male and female monkeys (*Macaca fascicularis*, approximately 3-4 years of age; Joinn Laboratories, Suzhou, China) were conducted under approved IACUC applications at a contracted animal facility under UBI sponsorship.
c. Mice:

Female Balb/C mice (n=6/group) were dosed for intramuscular injection (IM) with 40 μg/0.1 ml/dose test vaccine or 0.1 ml/dose control article in one injection site (quadricep femoral muscle on hind limb), 5 shots at 0, 3, 6, 9, 12 wpi prior to capsaicin challenge. Animals were housed at UBI Asia Laboratory Animal Facility and acclimatized for 1 week under constant temperature (22° C.), humidity (72%), 12-h light/12-h dark cycle. Mice had free access to chow and water. All protocols followed the Principles of Laboratory Animal Care. Blood collection was carried out as indicated in the protocol. Antibody titers were tested for anti-CGRP (mouse) by ELISA assay.

Example 5

Vaccine Formulations for Immunogenicity Assessment of CGRP Peptide Constructs in Guinea Pigs Pharmaceutical compositions and vaccine formulations used in each experiment are described in greater detail as shown below.

Briefly, the formulations specified in each of the study groups generally contained all types of designer CGRP peptide immunogen constructs with a segment of the CGRP B cell epitope peptide linked via different type of spacers (e.g., εLys (εK) or lysine-lysine-lysine (KKK) to enhance the peptide construct's solubility) and promiscuous helper T cell epitopes including two sets of artificial T helper epitopes derived from Measles virus fusion protein and Hepatitis B surface antigen. The CGRP B epitope peptides are linked at the N- or C-terminus of the designer peptide constructs. Hundreds of designer CGRP peptide immunogen constructs were initially evaluated in guinea pigs for their relative immunogenicity with the corresponding CGRPB cell epitope peptides. The CGRP peptide immunogen constructs were either prepared under varying amounts in a water-in-oil emulsion with Seppic MONTANIDE ISA 51 as the approved oil for human vaccine use, or with mineral salts (ADJUPHOS) or ALHYDROGEL (Alum) as a suspension, as specified. Vaccine formulations were usually prepared by dissolving the CGRP peptide constructs in water at about 20 to 800 μg/mL and formulated either with MONTANIDE ISA 51 into water-in-oil emulsions (1:1 in volume) or with mineral salts (ADJUPHOS) or ALHYDROGEL (Alum) (1:1 in volume). The vaccine formulations were kept at room temperature for about 30 min and mixed by vortex for about 10 to 15 seconds prior to immunization.

Some animals were immunized with 2 to 5 doses of a specific vaccine formulation, which were administered at time 0 (prime) and 3 weeks post initial immunization (wpi) (boost), optionally 5 or 6 wpi for a second boost, by intramuscular route. These immunized animals were then evaluated for the immunogenicity of the corresponding CGRP peptide immunogen constructs used in the respective vaccine formulations for their cross-reactivity with the corresponding CGRP B epitope peptides or full-length CGRP. Those CGRP peptide immunogen constructs with potent immunogenicity in the initial screening in guinea pigs were further tested in both water-in-oil emulsion, mineral salts, and alum-based formulations in macaques for dosing regimens over a specified period as dictated by the immunization protocols.

Only the most promising CGRP peptide immunogen construct candidates were further assessed extensively to evaluate for their ability to breakout immune tolerance in in mice using corresponding mouse CGRP peptide immunogen constructs. The CGRP peptide immunogen constructs with best immunogenicity in mice, which elicited anti-CGRP antibody titers against endogenous CGRP; especially for their capability of suppressing Capsaicin induced dermal blood flow in mice model. The optimized CGRP peptide immunogen constructs were incorporated into final vaccine formulations for GLP guided immunogenicity, duration, toxicity and proof of efficacy studies in preparation for submission of an Investigational New Drug application and clinical trials in patients with migraine.

Example 6

Figure 5:
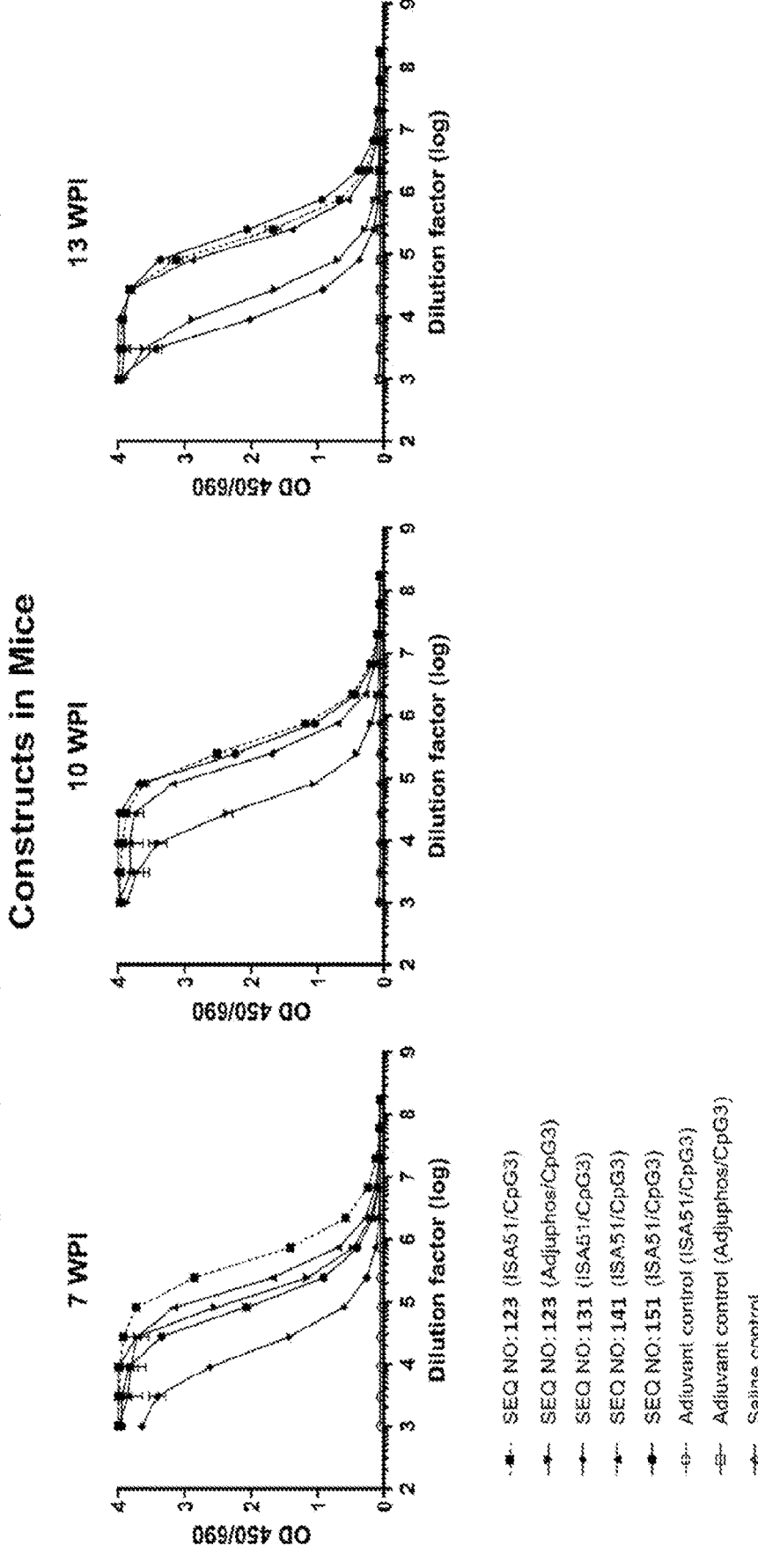
FIG. 5 illustrates the results from immunogenicity studies in Balb/C mice of representative CGRP peptide immunogen constructs (SEQ ID NOs: 123, 131, 141, 151) in both ADJUPHOS and ISA51 formulations with corresponding antibodies purified from guinea pig immune sera of 7 wpi, 10 wpi and 13 wpi bleeds, for their reactivities and cross-reactivities with full-length human CGRP molecule.

Design Rationale, Screening, Identification, Assessment of Functional Properties and Optimization of Multi-Component Vaccine Formulations Incorporating CGRP Peptide Immunogen Constructs for Treatment of Migraine Based on scientific information provided by FIGS. 1 and 2, as well as information disclosed in FIG. 5 of Russel, et al., 2014 and FIGS. 2(a)-2(c) of Edvinsson, et al., 2018, CGRP is selected as the target molecule for design and as the content of this instant invention. FIG. 1 presents alignment of CGRP sequences from human (SEQ ID NO: 1), marmoset (SEQ ID NO: 2), mouse/rat (SEQ ID NO: 3) and many other species; FIG. 5 of Russel, et al., 2014 depicts the physiology and pathophysiology associated with CGRP; and FIGS. 2(a)-2(c) of Edvinsson, et al., 2018 depicts why CGRP could be a target for new migraine therapies. FIG. 2 depicts the pathways from discovery to commercialization of high precision designer synthetic peptide based vaccines. A general summary of the steps is described in FIG. 2 with a flow chart identifying the development process from discovery to commercialization (industrialization) of an CGRP vaccine formulation. Detailed evaluation and analyses of each of the steps, with pleasant and unpleasant surprises, had led to a myriad of experiments in the past which would ultimately result in commercialization of a safe and efficacious CGRP vaccine formulation.

a. Design History

Each peptide immunogen construct or immunotherapeutic product requires its own design focus and approach based on its specific disease mechanism and the target protein(s) required for intervention. For treatment of migraine, CGRP was selected as the target molecule based on the scientific information available to us as outlined in FIG. 1 and in FIG. 5 of Russel, et al., 2014 and FIGS. 2(a)-2(c) of Edvinsson, et al., 2018. The pathways from discovery to commercialization as shown in FIG. 2 typically require one or more decades to accomplish. Identification of the CGRP B cell epitope peptides correlating to the functional site(s) for intervention are key to the immunogen construct design. Consecutive pilot immunogenicity studies in guinea pigs incorporating various T helper support (carrier proteins or suitable T helper peptides) in various formulations were conducted and subsequently evaluated for the functional properties of the elicited purified antibodies or the vaccine formulations employing specific CGRP peptide immunogen constructs in specific in vitro functional assays or proof of concept in vivo studies in selected animal models. Upon extensive serological validation, candidate CGRP B epitope peptide immunogen constructs were then further tested in non-human primates to further validate the immunogenicity and direction of the CGRP peptide immunogen design. Selected CGRP peptide immunogen constructs are then prepared in varying mixtures to evaluate the subtle differences in functional properties related to the respective interactions amongst peptide constructs when used in combinations. Upon additional evaluation, the final peptide constructs, peptide compositions and formulations thereof, along with the respective physical parameters of the formulations are established leading to the final product development process.

The amino acid sequences of the CGRP peptide immunogen constructs were selected based on a number of design rationales. Several of these rationales include employing a CGRP B epitope peptide sequence that:

(i) is devoid of an autologous T helper epitope within CGRP to prevent autologous T cell activation which could lead to inflammation of the brain resulting in meningococcal encephalitis as previously reported in clinical trials using AN1792 vaccine targeting $A\beta_{1-42}$ for treatment of Alzheimer's Disease;

(ii) is non-immunogenic on its own, since it is a self-molecule;

(iii) can be rendered immunogenic by a protein carrier or a potent T helper epitope(s) upon administration to a host:

(iv) elicits high titer antibodies directed against the CGRP peptide sequence (B cell epitope) and not against the protein carrier or potent T helper epitope(s);

(v) elicits high titer antibodies that would suppress the induction of intracellular cAMP rise due to CGRP and CGRP receptor interaction and cellular activation; and (vi) such vaccine formulations, when administered in an animal model, e.g. BALB/C mice, would suppress the dorsal blood flow induced by Capsaicin, as a proof of concept validation for the treatment of migraine.

b. Design and Validation of CGRP Peptide Immunogen Constructs for Pharmaceutical Compositions with Potential to Treat Patients Suffering from Migraine.

In order to generate the most potent peptide constructs for incorporation into the pharmaceutical compositions, a repertoire of human CGRP B cell epitope peptides (e.g. SEQ ID NOs: 4-24) and promiscuous T helper epitopes derived from various pathogens or artificially T helper epitopes (e.g. SEQ ID NOs: 74-115) were further designed and made into for example representative CGRP peptide immunogen constructs (e.g., SEQ ID NOs: 116-180) for immunogenicity studies initially in guinea pigs.

i) Selection of CGRP B Cell Epitope Peptide Sequences from the Receptor Binding or Receptor Activation Region for Design The CGRP receptor binding region located at the central/C-terminus of CGRP and the receptor activation region from N-terminus C2-C7 loop/central region of CGRP were selected for CGRP B epitope design and then further made into peptide immunogen constructs to elicit immune sera in guinea pigs initially for immunogenicity by ELISA on CGRP B epitope peptide coated plates and subsequently for in vitro functional assay assessment.

Figure 6:
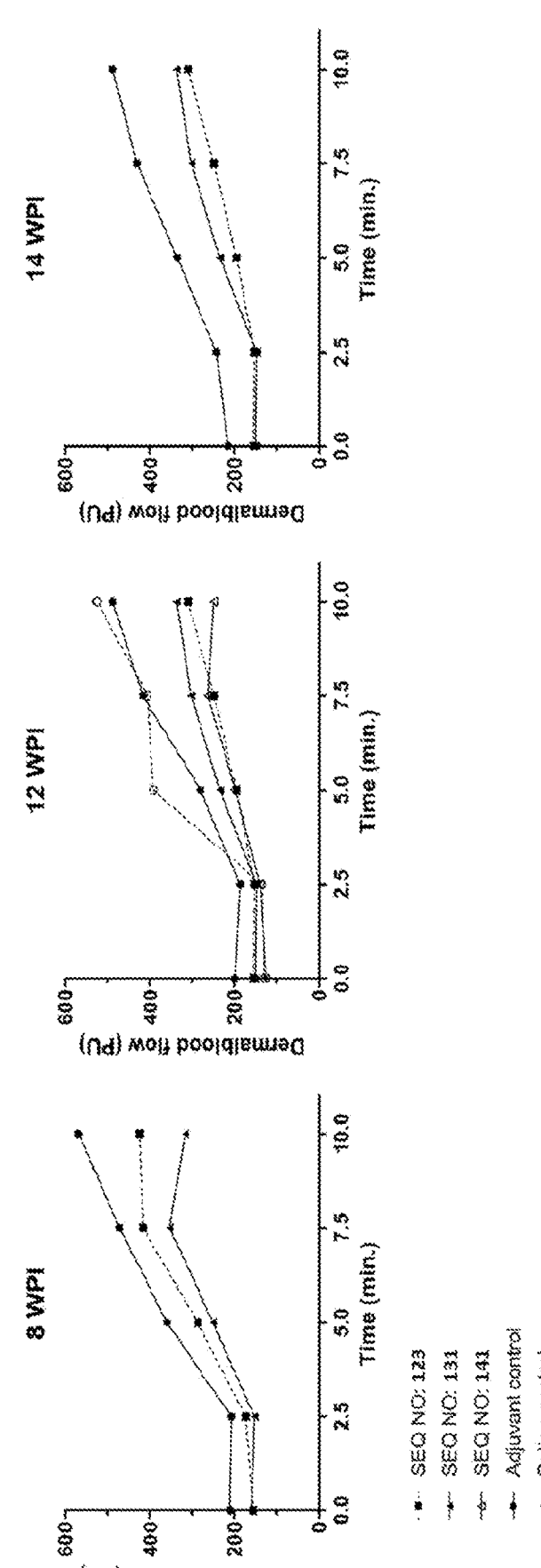
FIG. 6 illustrates the inhibitory effect of Capsaicin-induced dermal blood flow measured in Balb/C mice that had been vaccinated at 0, 3 and 6 wpi with CGRP peptide immunogen constructs (SEQ ID NOs: 123, 131, 141) formulated in either ADJUPHOS or ISA emulsion formulations as indicated, when compared to the control articles of adjuvant alone or saline.

Upon binding of CGRP to CGRP receptor, CGRP receptor transmits the activation signals intracellularly leading to intracellular rise of cAMP level amongst other cellular events. The ability of purified antibodies from guinea pig immune sera against specific CGRP peptide immunogen constructs to neutralize the functional properties of CGRP is assessed for $IC_{50}$ to inhibit 50% of CAMP rise when compared to the control in the absence of antibodies as shown in FIG. 6 and the tables displayed within FIG. 3.

Figure 3:
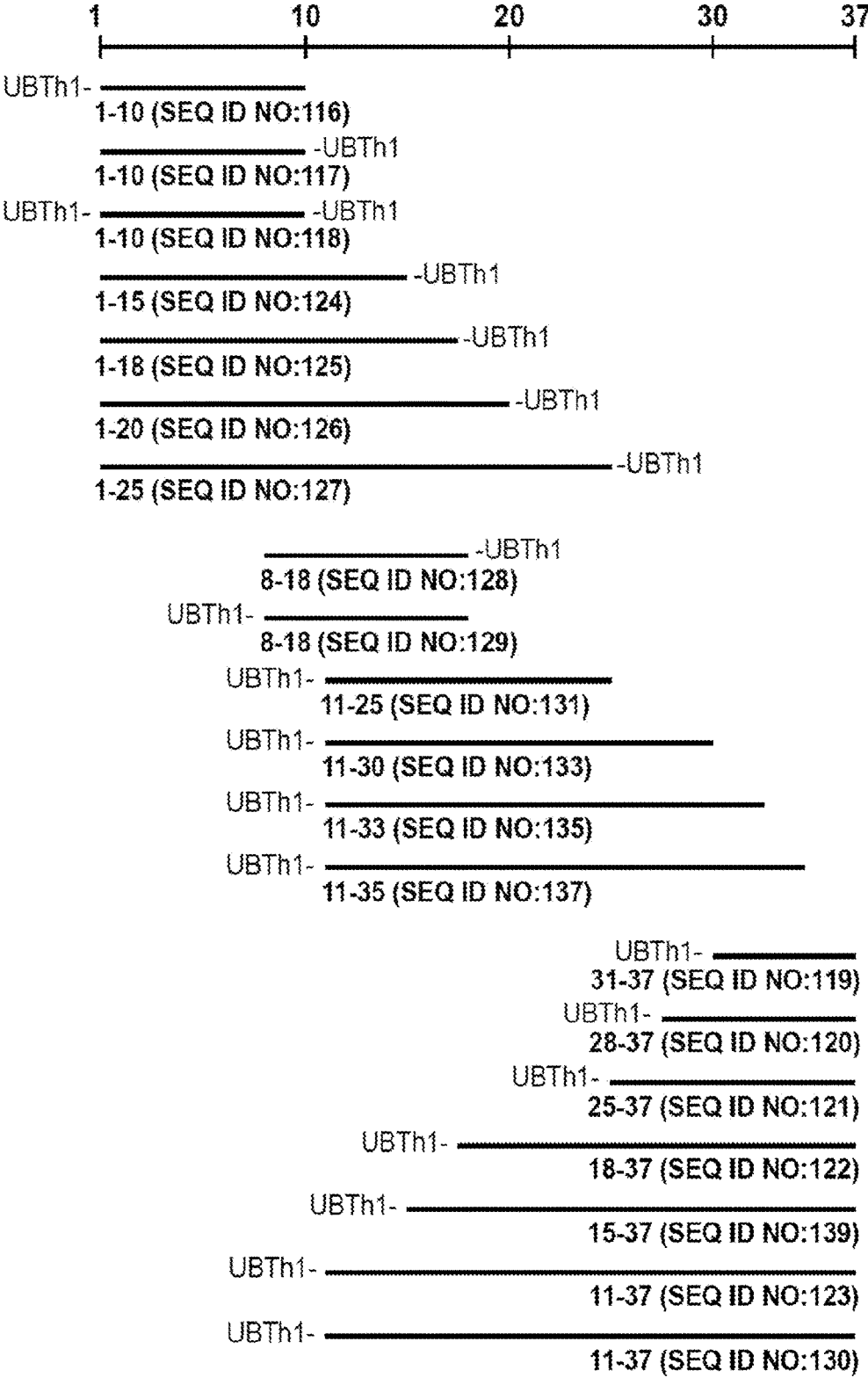
FIG. 3 depicts results from immunogenicity studies of CGRP peptide immunogen constructs (SEQ ID NOs: 116-118, 124-127, 128, 129, 131, 133, 135, 137, 119-122, 139, 123, 130) in guinea pigs with CGRP B cell epitope peptides derived from the N-terminal, Central, and C-terminal regions of the CGRP molecule.
Figure 3:
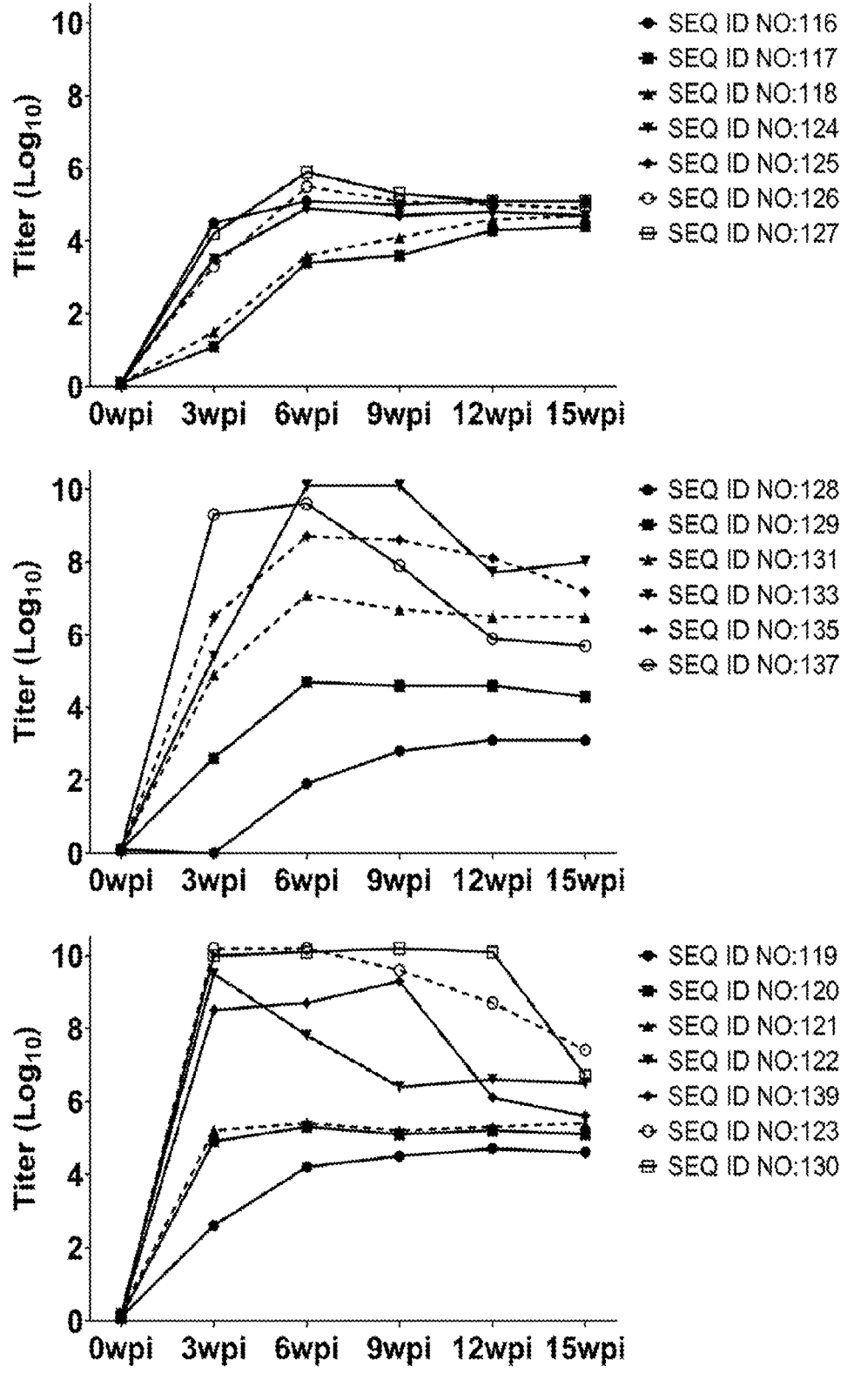

These CGRP peptide immunogen constructs were formulated initially with ISA 51 and CpG for prime immunization in guinea pigs at 400 µg/1 mL and boosts (3, 6 and 9 wpi) at 100 µg/0.25 mL for immunogenicity studies. To test the immunogenicity in guinea pigs, ELISA assay was used with guinea pig immune sera from various (wpi) bleeds, diluted at a 10-fold serial dilution from 1:100 to 1:10000. ELISA plates were coated with corresponding mouse/rat CGRP B epitope peptide and full-length CGRP peptide at 0.5 µg peptide per well. The titer of a tested serum, expressed as $Log_{10}$, was calculated by linear regression analysis of the A450 nm with the cutoff $A_{450}$ set at 0.5 as shown in FIG. 3 with detailed titers for representative B epitope derived CGRP peptide immunogen constructs as shown in Tables 4, 5 and 6. Despite that the designed short CGRP peptides frequently are non-immunogenic due to their lack of endogenous Th epitopes, addition of foreign Th epitopes could enhance the immunogenicity of the specific CGRP peptide immunogen constructs. Detailed analyses of the reactivity/specificity pattern of various constructs from Tables 4, 5, and 6 along with FIG. 3, immunogenicity imparted by certain residues within the CGRP molecule can be assessed which would facilitate further design of the optimal peptide immunogen constructs.

ii) Devoid of an Autologous T Helper Epitope within Selected CGRP B Epitope to Prevent Autologous T Cell Activation As shown in Table 7, representative CGRP B cell epitopes such as those with SEQ ID Nos: 5, 6 and 15, when administered in potent vaccine formulations used for counterpart peptide immunogen constructs, they themselves did not elicit any antibodies to CGRP thus are devoid of the undesirable endogenous Ths epitope within the selected CGRP B cell epitopes.

iii) Focused Antibody Response Elicited by CGRP Peptide Immunogen Constructs is Targeted at the CGRP B Cell Epitope Only It is well known that all carrier proteins (e.g. Keyhole Limpet Hemocyanin (KLH), Diphtheria toxoid (DT) and Tetanus Toxoid (TT) proteins) used to potentiate an immune response directed against the targeted B cell epitope peptide, by chemical conjugation of such B cell epitope peptide to the respective carrier protein, will elicit more than 90% of the antibodies directed against the potentiating carrier protein with less than 10% of the antibodies directed against the targeted B cell epitope in immunized hosts.

It is therefore of interest to assess the specificity of the CGRP peptide immunogen constructs of the present invention. Two representative CGRP peptide immunogen constructs (SEQ ID NOs: 142 and 142 from Table 8), with B cell epitopes of varying lengths from CGRP 20-37 and 22-37 that are linked through a spacer sequence to the heterologous T cell epitope UBITh® 1 (SEQ ID NO: 98), were prepared for immunogenicity assessment. The UBITh® 1 (T helper peptide used for B epitope immunopotentiation) was coated to the plates and the guinea pig immune sera were employed to test for cross-reactivities with the UBITh® 1 peptide used for immunopotentiation. In contrast to the high immunogenicity of these constructs towards the corresponding targeted CGRP B cell epitope peptides as illustrated by the high titers of antibodies ($>5$ $Log_{10}$) generated towards the CGRP B epitope(s) upon even a single shot, while as most, if not all, of the immune sera were found non-reactive to the UBITh® 1 peptide as shown in Table 8.

In summary, simple immunogen design incorporating target CGRP B cell epitope peptide linked to carefully selected T helper epitope allows the generation of a focused immune response targeted only to the corresponding CGRP B cell epitope peptide. For pharmaceutical composition design, the more specific the immune response it generates, the higher safety profile it provides for the composition. The CGRP peptide immunogen constructs of this instant invention is thus highly specific yet highly potent against its B cell target.

iv) Fine Epitope Mapping with Immune Sera Directed Against Selected CGRP Peptide Immunogen Constructs In a fine epitope mapping study as shown in Table 9 to localize the antibody binding site(s) to specific residues within the target B epitope region, 45 overlapping 10-mer peptides (SEQ ID NOs: 26-70) were synthesized that cover from amino acid-9 to amino acid 45 sequence covering the full-length region of CGRP along with the precursor sequences before and after the processed CGRP molecule. These 10-mer peptides were individually coated onto 96-well microtiter plate wells as solid-phase immune-absorbents. The pooled guinea pig antisera were added at a 1:100 dilution in specimen diluent buffer to the plate wells coated with 10-mer peptide at 2.0 µg/mL followed by incubation for one hour at 37° C. After washing the plate wells with wash buffer, the horseradish peroxidase-conjugated rProtein A/G was added and incubated for 30 min. After washing with PBS again, the substrate was added to the wells for measurement of absorbance at 450 nm by ELISA plate reader, when the samples were analyzed in duplicate. The binding of CGRP peptide immunogen elicited immune sera to the corresponding CGRP B cell epitope peptide coated wells represent the maximal antibody binding signal.

The fine epitope mapping results as shown in Table 9 revealed that the pooled guinea pig sera from CGRP peptide immunogen constructs of SEQ ID NOs: 122, 123, 127, 129, 130, 132, 137, and 139 comprising CGRP B epitope peptides from both the receptor binding region from AAs 11 to 37 and the receptor activation region around the C2-C7 loop from AAs 1-25, 11-25, 8-18, 11-35, 11-37, 15-37 and 18-37 induced high titer antibodies mainly against a cluster of 10mer peptides from amino acid 1-37 (SEQ ID NO: 1) with high cross-reactivities to peptides mainly with amino acids of varying patterns from 1-13 for B epitope 1-25; 15-26 for B epitope 11-25; none major for B epitope 8-18; 22-33 and 26-36 for B epitope 11-35; 23-33 and 28-37 for B epitope 11-37; 23-33 and 28-37 for B epitope 18-37; 22-33 and 26-36 for B epitope 11-35; 17-26, 20-30 and 28-37 for B epitope 15-37. It is of interest to find that despite the same B epitope was employed for the design of peptide immunogen constructs SEQ ID NOs: 123 and 130 with only spacer difference with SEQ ID NO: 123 being with an extra KKK spacer when compared to SEQ ID NO: 130, extra reactivities towards AAs 20-30 and AAs 26-36 were found with the construct SEQ ID NO: 130 which had a shorter spacer without the KKK residues.

In summary, the designed synthetic CGRP peptide immunogen constructs induced robust immune responses in guinea pigs generating polyclonal antibodies targeted at distinct clusters of 10mer peptides within CGRP, which have close proximity to both the CGRP receptor binding region near by the respective C-terminus and the receptor activation region nearby the C2-C7 loop, allowing for important medical interventions. Epitope mapping along with functional assay assessment would allow identification of the most optimal peptide immunogen constructs for use in vaccine formulations.

Example 7

Assessment of Functional Properties of Antibodies Elicited by the CGRP Peptide Immunogen Constructs and Formulations Thereof in an Ex-Vivo Mode After demonstration of the high immunogenicity and cross-reactivities of the antibodies purified from immune sera of guinea pigs immunized with carefully selected candidate CGRP immunogen constructs as shown in Tables 4, 5, 6, 7, 8 and 9, the following studies were designed to assess whether representative purified IgGs from these immune sera collected at 6 wpi from each animal could suppress intracellular rise of cAMP due to activation by the C2-C7 loop within the CGRP upon binding of CGRP to its receptor.

At a molecular level within smooth muscle cells, CGRP could bind to its receptor via its C-terminal region and then activate the receptor by using it loop region (reference). The cyclic C2-C7 loop with a disulfide bridge has a basic role in receptor activation which correlates closely with a rise in intracellular cAMP. Various anti-CGRP IgGs were used to characterize their potential anti-CGRP influence in a neutralization assay. Specifically, the effect was assessed by functional pharmacology using the alterations in intracellular cAMP levels. This in vitro functional assessment is particularly important to assess the anti-CGRP effect of those guinea pig immune sera directed against CGRP peptide immunogen constructs of the current invention with assay procedures detailed in EXAMPLE 4.

Figure 4:
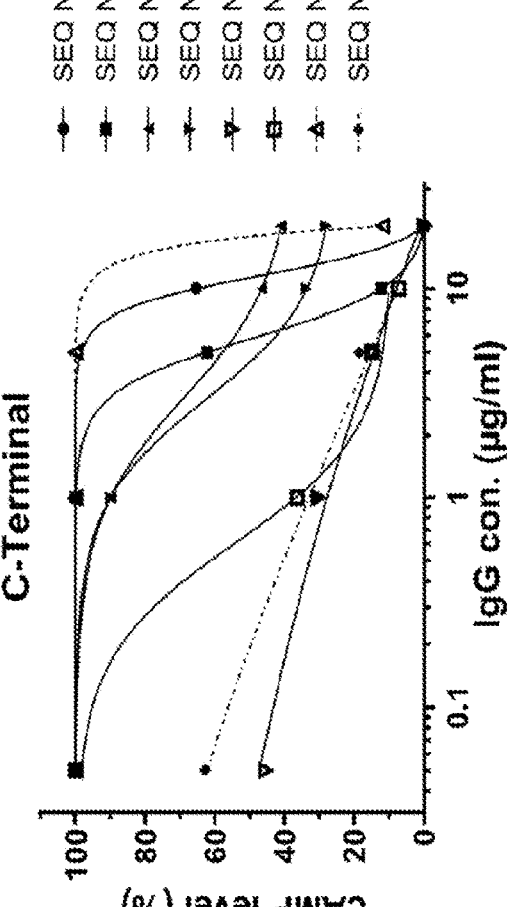
FIG. 4 depicts neutralization activities, expressed as $IC_{50}$ of intracellular cAMP production in CGRP activated cell culture in the presence of purified antibodies from guinea pig immune sera (collected from 6 wpi bleeds) of representative CGRP peptide immunogen constructs (SEQ ID NOs: 116-118, 124-127, 128, 129, 131, 133, 135, 137, 119-123, 130, 139, and 150).

Suppression of Intracellular cAMP Rise in CGRP Activated Phosphorylation by Anti-CGRP Antibodies Immune sera from 6 wpi bleeds of each animal were collected with antibodies purified as described in EXAMPLE 4. Twenty-one CGRP peptide immunogen constructs were tested in guinea pigs for their respective immunogenicity as demonstrated in EXAMPLE 6. The purified antibodies were grouped into three categories based on their respective target B cell epitope peptides employed in the peptide immunogen constructs. They are those directed at B cell epitope peptides from the N-terminal region, Central region and those from the C-terminal region respectively. Data are recorded in percentage of cAMP detected within the CGRP treated L6 cell. Zero % represents L6 cell alone and 100% stands for CGRP treated L6 cell. As shown in FIG. 4, along with the accompanying tables, there are constructs incorporating CGRP B epitope peptides from N-terminal, Central, or C-terminal region that showed $IC_{50}$ (μg/mL) for cAMP level from 0.60 to >20. For practical purpose, we use $IC_{50}$ at less than 10 μg/mL as significant in antibody mediated suppression of cAMP production. Representative constructs that showing effective functional immunogenicity are ranked (with $IC_{50}$ μg/mL from low to high) as SEQ ID NOs: 130>127>150>125>137>123>121>119>124>131>126> 133>120>129>135>116~117~118~128~139 and we can delineate the optimal design for CGRP peptide immunogen constructs with high precision up to a few residues within the CGRP 37mer structure.

In summary, CGRP peptide immunogen constructs as shown above in their relative ranking for respective functional properties are of value for use in subsequent CGRP vaccine formulations to demonstrate functional efficacy.

Example 8

Assessment of Representative Mouse CGRP Peptide Immunogen Construct in a Preventive Mode on the Capsaicin Induced Dermal Blood Flow Model in Balb/C Mice as a Proof of Concept CGRP Vaccine Study
a. Study Rationales.

Calcitonin gene-related peptide (CGRP) is a 37 amino acid peptide that is widely expressed in the central and peripheral nervous system. It is primarily associated with small unmyelinated sensory neurons, which are in close proximity of blood vessels. CGRP is a potent vasodilator and local administration of CGRP causes transient increases in blood flow. CGRP has also been associated with pain transmission, pain modulation, and neurogenic inflammation. CGRP can be released from sensory neurons via activation of the transient receptor potential cation channel using capsaicin.

Laser Doppler Imaging (LDI) has been used to detect the resulting changes in dermal blood flow which has been shown to be predominantly caused by CGRP. CGRP is also linked to inflammatory pain as demonstrated by attenuated responses in CGRP knock-out mice in a number of pain models. This role in pain perception is congruent with the expression of CGRP in sensory neurons.

In the mammalian plasma, the half-life of CGRP is ~10 min. In the human trigeminal ganglia, CGRP-immunoreactive neurons account for up to 50% of all neurons (Tajti, et al., 1999). By targeting the CGRP to treat the migraine headaches with anti-CGRP vaccination approach can fulfill an unmet medical needs to treat migraine in a prophylactic mode cost effectively over a long duration with the potential for long-term CGRP blockade.

This study is designed to test in a Balb/C mice model the murine CGRP peptide immunogen constructs of representative counterparts of human CGRP peptide immunogen constructs counterpart identified in EXAMPLE 7 for their ability in reduction of Capsaicin induced dermal blood flow as a proof of concept study to illustrate the efficacy of the anti CGRP vaccine treatment for migraine.

b. Study Design.
i) Representative Test Articles:
CGRP peptide immunogen construct vaccine formulations used in this study are listed below:
Group 1: UBITh® 1-human $\alpha CGRP_{11-37}$ (SEQ ID NO: 123) with ISA51 and CpG3
Group 2: UBITh® 3-human $\alpha CGRP_{11-37}$ (SEQ ID NO: 141) with ISA51 and CpG3
Group 3: UBITh® 3-rat/mouse $\alpha CGRP_{11-37}$ (SEQ ID NO: 151) with ISA51 and CpG3
Group 4: UBITh® 1-human $\alpha CGRP_{11-37}$ (SEQ ID NO: 123) with ADJUPHOS and CpG3
Group 5: UBITh® 1-human $\alpha CGRP$ (SEQ ID NO: 131) with ISA51 and CpG3
These articles along with group information were listed in Table 2.
ii) Control Articles:
Group 6: ISA51 and CpG3
Group 7: ADJUPHOS and CpG3
Group 8: Saline
iii) Groups and Dosage:
Grouping is executed as following:
iv) Individual Identification:
Tested animals were identified by picric acid marker.
v) Group Identification:
Cages were properly labeled for identification, including the Study Title, IACUC No., Route of Administration, Observation Period, Cage No., Quantity/cage, Species, Strain, Gender, In House Date, In House Age, Animal ID No., Keeper and Deputy
vi) Administration Route and Injection Site:
Female Balb/C mice (n=6/group) were dosed intramuscularly (IM) with 40 μg/0.1 ml/dose for test vaccine article or 0.1 ml/dose for control article in one injection site (quadricep femoral muscle on hind limb), 5 shots at 0, 3, 6, 9, 12 wpi prior to capsaicin challenge.
vii) Treatment Schedule:
A total of 5 injections of control or test articles were administered during the course of treatment at 0, 3, 6, 9 and 12 wpi.
viii) Bio-Sample Collection and Preparation:
Blood were clotted in tube at room temperature, undisturbed for a minimum of 30 to a maximum of 60 minutes to separate serum from blood clot. Blood clot was removed by centrifugation at 1,000×g for 10 minutes using a refrigerated centrifuge. Serum was transferred immediately into sterile 1.5 mL Eppendorf polypropylene tubes. All samples were maintained on wet ice during handling. Unused serum samples were stored frozen at −80° C.
ix) Laser Doppler Imaging (LDI):
On the day of the experiment, the mouse lower backs were shaved and the mice were placed on a heating pad under the LDI instrument. Anesthesia was induced with 25 mg/kg Zoletil and the animal was stabilized under anesthesia for approximately 20 min prior to scanning. The scan series began with two baseline scans after which 2 μL of capsaicin solution (50 mg capsaicin in a solution of 83.4 μL EtOH, 55.6 μL Tween 20, 27.8 μL purified $H_2O$ in a 3:2:1 ratio) was applied to each of the two O-rings which were placed on the lower back of the animal. Scanning was continued with a scan every 2.5 min for an additional 10 min. Data were analyzed using moorVMS-LDF software for regions of interest. Excel worksheets were used for averaging the signal from the regions of interest at each time point. Data are reported as percent change from the baseline.
x) Immunological Analysis of Antibody Titers:
Samples of serum or CSF were collected with anti-CGRP antibody titers measured by ELISA kits prepared as shown in EXAMPLE 2 using full-length human CGRP for antigen coating. Serum samples were serially diluted 3-fold with a starting dilution of 1:1000. The antibody ELISA titers, expressed in $Log_{10}$, were determined using an automated plate reader at absorbance, $A_{450}$ nm.

c. Study Results.

i) Injection Site Reaction:

Slight and temporal swelling at the injection site was occasionally observed as a result of immunization procedure.

ii) Antibody Titers of the Immune Sera from Immunized Mice:

Representative ELISA results showed that two peptide immunogen constructs from mice counterparts (e.g. SEQ ID NO: 151) of CGRP peptide immunogen constructs (SEQ ID NOs: 132 and 141) not only induced high immunogenicity titers against their respective B epitope peptides (SEQ ID NOs: 15 and 9), antibodies from these two immune sera were also found to have moderate cross-reactivity against their homologous full-length human CGRP as shown in FIG. 5. The study indicated that the two representative CGRP peptide immunogens are able to induce specific antibodies with cross-reactivity against human CGRP B epitope peptide and its mouse counterpart peptide. The mouse/rat CGRP B epitope peptide immunogen construct counterparts employed UBITh® 3 (a combinatorial Th peptide library that is more potent than the UBITh® 1) as the T helper peptide to enhance further the immunogenicity of the selected constructs in mice (e.g. SEQ ID NO: 132, 134, 136, 138, 140, 141, and 151) and linker (e.g. SEQ ID NO: 72) in this POC animal study.

iii) LDI Result:

The Capsaicin model for dermal blood flow measurement is an in vivo pharmacodynamic model in both animals as well as humans. It is non-invasive, technically uncomplicated and gives a rapid and objective endpoint. This model can be repeatedly tested with measurements being adequately reproducible. This model therefore offers an ideal assessment for clinical evaluation of CGRP blocking therapeutics. Like all other biomarker models, this model also has its limitations. The Capsaicin model remains a simulation of a naturally occurring pathophysiological process of a desired study. The effect of a drug or vaccine induced antibodies on Capsaicin-induced dermal blood flow could offer trends of anti-CGRP activity that are indicative for their efficacy in inhibiting peripheral dermal blood flow.

As shown in FIG. 6, when compared to the control articles of saline or various adjuvant alone formulations, the CGRP peptide immunogen constructs with SEQ ID NOs: 123, 131, 141, and 151 in both ADJUPHOS and ISA51 formulations containing CpG in the formation of peptide/CpG complexes, elicited significant specific titers ($Log_{10}$ from 4 to 6) of anti CGRP antibodies in the vaccinated mice after receiving three immunizations. The animals showed respective suppression of the Capsaicin-induced dermal microvascular blood flow (FIG. 6) with the measurements taken at 8 wpi, 12 wpi and 14 wpi. The duration of such inhibition lasted 14 weeks for the period measured. Despite differences found in the titers of the selected antibody preparations in the immunogenicity study, or their corresponding $IC_{50}$s in an in vitro assay measurement for the respective antibodies' cAMP inhibition potencies, the three representative CGRP peptide immunogen constructs (e.g. SEQ ID NOs: 123, 131, and 141) and formulations thereof, shared similar capability in the reduction of Capsaicin-induced dermal blood flow in these vaccinated mice, indicative of the efficacy in using these CGRP peptide immunogen constructs for the treatment of migraine.

TABLE 1

| Amino Acid Sequences of α-CGRP and Fragments Thereof Employed in Serological Assays | | |
|---|---|---|
| Amino Acid positions within α-CGRP | SEQ ID NO: | Sequence |
| Human α-CGRP $_{1-37}$ | 1 | ACDTA TCVTH RLAGL LSRSG GVVKN NFVPT NVGSK AF |
| Marmoset α-CGRP $_{1-37}$ | 2 | ACDTA TCVTH RLAGL LSRSG GMVKN NFVPT NVGSE AF |
| Rat/Mouse α-CGRP $_{1-37}$ | 3 | SCNTA TCVTH RLAGL LSRSG GVVKD NFVPT NVGSE AF |
| α-CGRP $_{1-10}$ | 4 | ACDTA TCVTH |
| α-CGRP $_{31-37}$ | 5 | NVGSK AF |
| α-CGRP $_{28-37}$ | 6 | VPTNV GSKAF |
| α-CGRP $_{25-37}$ | 7 | NNFVP TNVGS KAF |
| α-CGRP $_{18-37}$ | 8 | RSGGV VKNNF VPTNV GSKAF |
| α-CGRP $_{11-37}$ | 9 | RLAGL LSRSG GVVKN NFVPT NVGSK AF |
| α-CGRP $_{1-15}$ | 10 | ACDTA TCVTH RLAGL |
| α-CGRP $_{1-18}$ | 11 | ACDTA TCVTH RLAGL LSR |
| α-CGRP $_{1-20}$ | 12 | ACDTA TCVTH RLAGL LSRSG |
| α-CGRP $_{1-25}$ | 13 | ACDTA TCVTH RLAGL LSRSG GVVKN |
| α-CGRP $_{8-18}$ | 14 | VTHRL AGLLS R |
| α-CGRP $_{11-25}$ | 15 | RLAGL LSRSG GVVKN |
| α-CGRP $_{11-30}$ | 16 | RLAGL LSRSG GVVKN NFVPT |

TABLE 1-continued

Amino Acid Sequences of α-CGRP and Fragments Thereof Employed in
Serological Assays

| Amino Acid positions within α-CGRP | SEQ ID NO: | Sequence |
|---|---|---|
| α-CGRP $_{11-33}$ | 17 | RLAGL LSRSG GVVKN NFVPT NVG |
| α-CGRP $_{11-35}$ | 18 | RLAGL LSRSG GVVKN NFVPT NVGSK |
| α-CGRP $_{15-37}$ | 19 | LLSRS GGVVK NNFVP TNVGS KAF |
| α-CGRP $_{20-37}$ | 20 | GGVVK NNFVP TNVGS KAF |
| α-CGRP $_{22-37}$ | 21 | VVKNN FVPTN VGSKA F |
| α-CGRP $_{11-18}$ | 22 | RLAGL LSR |
| α-CGRP $_{5-18}$ | 23 | ATCVT HRLAG LLSR |
| α-CGRP $_{4-16}$ | 24 | TATCV THRLA GLL |
| Rat α-CGRP $_{11-37}$ | 25 | RLAGL LSRSG GVVKD NFVPT NVGSE AF |
| α-CGRP $_{-9-1}$ | 26 | GSRII AQKRA |
| α-CGRP $_{-8-2}$ | 27 | SRIIA QKRAC |
| α-CGRP $_{-7-3}$ | 28 | RIIAQ KRACD |
| α-CGRP $_{-6-4}$ | 29 | IIAQK RACDT |
| α-CGRP $_{-5-5}$ | 30 | IAQKR ACDTA |
| α-CGRP $_{-4-6}$ | 31 | AQKRA CDTAT |
| α-CGRP $_{-3-7}$ | 32 | QKRAC DTATC |
| α-CGRP $_{-2-8}$ | 33 | KRACD TATCV |
| α-CGRP $_{-1-9}$ | 34 | RACDT ATCVT |
| α-CGRP $_{1-10}$ | 35 | ACDTA TCVTH |
| α-CGRP $_{2-11}$ | 36 | CDTAT CVTHR |
| α-CGRP $_{3-12}$ | 37 | DTATC VTHRL |
| α-CGRP $_{4-13}$ | 38 | TATCV THRLA |
| α-CGRP $_{5-14}$ | 39 | ATCVT HRLAG |
| α-CGRP $_{6-15}$ | 40 | TCVTH RLAGL |
| α-CGRP $_{7-16}$ | 41 | CVTHR LAGLL |
| α-CGRP $_{8-17}$ | 42 | VTHRL AGLLS |
| α-CGRP $_{9-18}$ | 43 | THRLA GLLSR |
| α-CGRP $_{10-19}$ | 44 | HRLAG LLSRS |
| α-CGRP $_{11-20}$ | 45 | RLAGL LSRSG |
| α-CGRP $_{12-21}$ | 46 | LAGLL SRSGG |
| α-CGRP $_{13-22}$ | 47 | AGLLS RSGGV |
| α-CGRP $_{14-23}$ | 48 | GLLSR SGGVV |
| α-CGRP $_{15-24}$ | 49 | LLSRS GGVVK |
| α-CGRP $_{16-25}$ | 50 | LSRSG GVVKN |
| α-CGRP $_{17-26}$ | 51 | SRSGG VVKNN |
| α-CGRP $_{18-27}$ | 52 | RSGGV VKNNF |
| α-CGRP $_{19-28}$ | 53 | SGGVV KNNFV |

TABLE 1-continued

Amino Acid Sequences of α-CGRP and Fragments Thereof Employed in
Serological Assays

| Amino Acid positions within α-CGRP | SEQ ID NO: | Sequence |
|---|---|---|
| α-CGRP $_{20-29}$ | 54 | GGVVK NNFVP |
| α-CGRP $_{21-30}$ | 55 | GVVKN NFVPT |
| α-CGRP $_{22-31}$ | 56 | VVKNN FVPTN |
| α-CGRP $_{23-32}$ | 57 | VKNNF VPTNV |
| α-CGRP $_{24-33}$ | 58 | KNNFV PTNVG |
| α-CGRP $_{25-34}$ | 59 | NNFVP TNVGS |
| α-CGRP $_{26-35}$ | 60 | NFVPT NVGSK |
| α-CGRP $_{27-36}$ | 61 | FVPTN VGSKA |
| α-CGRP $_{28-37}$ | 62 | VPTNV GSKAF |
| α-CGRP $_{29-38}$ | 63 | PTNVG SKAFG |
| α-CGRP $_{30-39}$ | 64 | TNVGS KAFGR |
| α-CGRP $_{31-40}$ | 65 | NVGSK AFGRR |
| α-CGRP $_{32-41}$ | 66 | VGSKA FGRRR |
| α-CGRP $_{33-42}$ | 67 | GSKAF GRRRR |
| α-CGRP $_{34-43}$ | 68 | SKAFG RRRRD |
| α-CGRP $_{35-44}$ | 69 | KAFGR RRRDL |
| α-CGRP $_{36-45}$ | 70 | AFGRR RRDLQ |
| Flexible Hinge Spacer | 71 | PPXPXP |
| Spacer1 | 72 | εK-KKK |
| Spacer2 | 73 | KKK-εK |

TABLE 2

Amino Acid Sequences of Pathogen Protein Derived
Th Epitopes Including Idealized Artificial Th
Epitopes for Employment in the Design of
α-CGRP Peptide Immunogen Constructs

| Description | SEQ ID NO: | Sequence |
|---|---|---|
| Clostridium tetani1 Th | 74 | KKQYIKANSKFIGITEL |
| MvF1 Th | 75 | LSEIKGVIVHRLEGV |
| Bordetella pertussis Th | 76 | GAYARCPNGTRALTVAELRGNAEL |
| Clostridium tetani2 Th | 77 | WVRDIIDDFTNESSQKT |
| Diphtheria Th | 78 | DSETADNLEKTVAALSILPGHGC |
| Plasmodium falciparum Th | 79 | DHEKKHAKMEKASSVENVVNS |
| Schistosoma mansoni Th | 80 | KWFKTNAPNGVDEKHRH |

TABLE 2-continued

Amino Acid Sequences of Pathogen Protein Derived
Th Epitopes Including Idealized Artificial Th
Epitopes for Employment in the Design of
α-CGRP Peptide Immunogen Constructs

| Description | SEQ ID NO: | Sequence |
|---|---|---|
| Cholera Toxin Th | 81 | ALNIWDRFDVFCTLGATTGYLKGNS |
| MvF2 Th | 82 | ISEIKGVIVHKIEGI |
| KKKMvF3 Th | 83 | KKKISISEIKGVIVHKIEGILF |
|  | 84 |     T  RT   TR  T |
|  | 85 | KKKISIXEIXXVIVXXIEXILF |
| HBsAg1 Th | 86 | KKKLFLLTKLLTLPQSLD |
|  | 87 | RRRIKII RII I L IR |
|  | 88 |    VRVV  VV V I V |
|  | 89 |     F FF  FF F V F |
|  | 90 |                F |
|  | 91 | XXXXXXXTXXXTXPXSXX |
| MvF4 Th (UBITh®3) | 92 | ISISEIKGVIVHKIETILF |
|  | 93 |    T  RT   TR |
|  | 94 | ISIXEIXXVIVXXIETILF |
| HBsAg2 Th | 95 | KKKIITITRIITIPQSLD |
|  | 96 |     FFLL    L  ITTI |
|  | 97 | KKKXXXXTRIXTIXXXXD |
| MvF5 Th (UBITh®1) | 98 | ISITEIKGVIVHRIETILF |
| HBsAg3 Th (UBITh®2) | 99 | KKKIITITRIITIITTID |
| Influenza MP1_1 Th | 100 | FVFTLTVPSER |
| Influenza MP1_2 Th | 101 | SGPLKAEIAQRLEDV |
| Influenza NSP1 Th | 102 | DRLRRDQKS |
| EBV BHRF1 Th | 103 | AGLTLSLLVICSYLFISRG |
| Clostridium tetani TT1 Th | 104 | QYIKANSKFIGITEL |
| EBV EBNA-1 Th | 105 | PGPLRESIVCYFMVFLQTHI |
| Clostridium tetani TT2 Th | 106 | FNNFTVSFWLRVPKVSASHLE |
| Clostridium tetani TT3 Th | 107 | KFIIKRYTPNNEIDSF |
| Clostridium tetani TT4 Th | 108 | VSIDKFRIFCKALNPK |
| EBV CP Th | 109 | VPGLYSPCRAFFNKEELL |
| HCMV IE1 Th | 110 | DKREMWMACIKELH |
| EBV GP340 Th | 111 | TGHGARTSTEPTTDY |
| EBV BPLF1 Th | 112 | KELKRQYEKKLRQ |
| EBA EBNA-2 Th | 113 | TVFYNIPPMPL |
| HBsAg4 Th (UBITh®4) | 114 | FFLLTRILTIPQSLD |
| Yersinia Invasin Th (Inv) | 115 | ALNIWDRFDVFCTLGATTGYLKGNS |

TABLE 3

| Amino Acid Sequences of α-CGRP Peptide Immunogen Constructs | | |
|---|---|---|
| Peptide Description | SEQ ID NO: | Sequence |
| UBITh1-εK-KKK-α-CGRP $_{1-10}$ | 116 | UBITh1-εK-KKK-ACDTATCVTH |
| α-CGRP $_{1-10}$-KKK-εK-UBITh1 | 117 | ACDTATCVTH-KKK-εK-UBITh1 |
| UBITh1-εK-KKK-α-CGRP $_{1-10}$-KKK-εK-UBITh1 | 118 | UBITh1-εK-KKK-ACDTATCVTH-kkk-ak-UBITh1 |
| UBITh1-εK-KKK-α-CGRP $_{31-37}$ | 119 | UBITh1-εK-KKK-NVGSKAF |
| UBITh1-εK-KKK-α-CGRP $_{28-37}$ | 120 | UBITh1-εK-KKK-VPTNVGSKAF |
| UBITh1-εK-KKK-α-CGRP $_{25-37}$ | 121 | UBITh1-εK-KKK-NNFVPTNVGSKAF |
| UBITh1-εK-KKK-α-CGRP $_{18-37}$ | 122 | UBITh1-εK-KKK-RSGGVVKNNFVPTNVGSKAF |
| UBITh1-εK-KKK-α-CGRP $_{11-37}$ | 123 | UBITh1-εK-KKK-RLAGLLSRSGGVVKNNFVPTNVGSKAF |
| α-CGRP $_{1-15}$-KKK-εK-UBITh1 | 124 | ACDTATCVTHRLAGL-KKK-εK-UBITh1 |
| α-CGRP $_{1-18}$-KKK-εK-UBITh1 | 125 | ACDTATCVTHRLAGLLSR-KKK-εK-UBITh1 |
| α-CGRP $_{1-20}$-KKK-εK-UBITh1 | 126 | ACDTATCVTHRLAGLLSRSG-KKK-εK-UBITh1 |
| α-CGRP $_{1-25}$-KKK-εK-UBITh1 | 127 | ACDTATCVTHRLAGLLSRSGGVVKN-KKK-εK-UBITh1 |
| α-CGRP $_{8-18}$-KKK-εK-UBITh1 | 128 | VTHRLAGLLSR-KKK-εK-UBITh1 |
| UBITh1-εK-KKK-α-CGRP $_{8-18}$ | 129 | UBITh1-εK-KKK-VTHRLAGLLSR |
| UBITh1-εK-α-CGRP $_{11-37}$ | 130 | UBITh1-εK-RLAGLLSRSGGVVKNNFVPTNVGSKAF |
| UBITh1-εK-KKK-α-CGRP $_{11-25}$ | 131 | UBITh1-εK-KKK-RLAGLLSRSGGVVKN |
| UBITh3-εK-KKK-α-CGRP $_{11-25}$ | 132 | UBITh3-εK-KKK-RLAGLLSRSGGVVKN |
| UBITh1-εK-KKK-α-CGRP $_{11-30}$ | 133 | UBITh1-εK-KKK-RLAGLLSRSGGVVKNNFVPT |
| UBITh3-εK-KKK-α-CGRP $_{11-30}$ | 134 | UBITh3-εK-KKK-RLAGLLSRSGGVVKNNFVPT |
| UBITh1-εK-KKK-α-CGRP $_{11-33}$ | 135 | UBITh1-εK-KKK-RLAGLLSRSGGVVKNNFVPTNVG |
| UBITh3-εK-KKK-α-CGRP $_{11-33}$ | 136 | UBITh3-εK-KKK-RLAGLLSRSGGVVKNNFVPTNVG |
| UBITh1-εK-KKK-α-CGRP $_{11-35}$ | 137 | UBITh1-εK-KKK-RLAGLLSRSGGVVKNNFVPTNVGSK |
| UBITh3-εK-KKK-α-CGRP $_{11-35}$ | 138 | UBITh3-εK-KKK-RLAGLLSRSGGVVKNNFVPTNVGSK |
| UBITh1-εK-KKK-α-CGRP $_{15-37}$ | 139 | UBITh1-K-KKK-LLSRSGGVVKNNFVPTNVGSKAF |
| UBITh3-εK-KKK-α-CGRP $_{15-37}$ | 140 | UBITh3-εK-KKK-LLSRSGGVVKNNFVPTNVGSKAF |
| UBITh3-εK-KKK-α-CGRP $_{11-37}$ | 141 | UBITh3-εK-KKK-RLAGLLSRSGGVVKNNFVPTNVGSKAF |
| UBITh1-εK-KKK-α-CGRP $_{20-37}$ | 142 | UBITh1-εK-KKK-GGVVKNNFVPTNVGSKAF |
| UBITh1-εK-KKK-α-CGRP $_{22-37}$ | 143 | UBITh1-εK-KKK-VVKNNFVPTNVGSKAF |
| α-CGRP $_{11-18}$-KKK-εK-UBITh1 | 144 | RLAGLLSR-KKK-εK-UBITh1 |
| α-CGRP $_{5-18}$-KKK-εK-UBITh1 | 145 | ATCVTHRLAGLLSR-KKK-εK-UBITh1 |
| α-CGRP $_{4-16}$-KKK-εK-UBITh1 | 146 | TATCVTHRLAGLL-KKK-εK-UBITh1 |
| UBITh3-εK-KKK-α-CGRP $_{28-37}$ | 147 | UBITh3-εK-KKK-VPTNVGSKAF |
| α-CGRP $_{1-20}$-KKK-εK-UBITh3 | 148 | ACDTATCVTHRLAGLLSRSG-KKK-εK-UBITh3 |
| UBITh3-εK-KKK-α-CGRP $_{1-20}$ | 149 | UBITh3-εK-KKK-ACDTATCVTHRLAGLLSRSG |
| UBITh1-εK-KKK-Rat α-CGRP $_{11-37}$ | 150 | UBITh1-εK-KKK-RLAGLLSRSGGVVKDNFVPTNVGSEAF |
| UBITh3-εK-KKK-Rat α-CGRP $_{11-37}$ | 151 | UBITh3-εK-KKK-RLAGLLSRSGGVVKDNFVPTNVGSEAF |
| Clostridium tetani1 Th-εK-KKK-α-CGRP $_{11-25}$ | 152 | KKQYIKANSKFIGITEL-εK-KKK-RLAGLLSRSGGVVKN |

TABLE 3-continued

| Amino Acid Sequences of α-CGRP Peptide Immunogen Constructs | | |
|---|---|---|
| Peptide Description | SEQ ID NO: | Sequence |
| MvF1 Th-εK-KKK-α-CGRP 11-25 | 153 | LSEIKGVIVHRLEGV-εK-KKK-RLAGLLSRSGGVVKN |
| Bordetella pertussis Th-εK-KKK-α-CGRP 11-25 | 154 | GAYARCPNGTRALTVAELRGNAEL-εK-KKK-RLAGLLSRSGGVVKN |
| Clostridium tetani2 Th-εK-KKK-α-CGRP 11-25 | 155 | WVRDIIDDFTNESSQKT-εK-KKK-RLAGLLSRSGGVVKN |
| Diphtheria Th-εK-KKK-α-CGRP 11-25 | 156 | DSETADNLEKTVAALSILPGHGC-εK-KKK-RLAGLLSRSGGVVKN |
| Plasmodium falciparum Th-εK-KKK-α-CGRP 11-25 | 157 | DHEKKHAKMEKASSVFNVVNS-εK-KKK-RLAGLLSRSGGVVKN |
| Schistosoma mansoni Th-εK-KKK-α-CGRP 11-25 | 158 | KWFKTNAPNGVDEKHRH-εK-KKK-RLAGLLSRSGGVVKN |
| Cholera Toxin Th-εK-KKK-α-CGRP 11-25 | 159 | ALNIWDRFDVFCTLGATTGYLKGNS-εK-KKK-RLAGLLSRSGGVVKN |
| MvF2 Th-εK-KKK-α-CGRP 11-25 | 160 | ISEIKGVIVHKIEGI- εK-KKK-RLAGLLSRSGGVVKN |
| KKKMvF3 Th-εK-KKK-α-CGRP 11-25 | 161 | KKKISISEIKGVIVHKIEGILF-εK-KKK-RLAGLLSRSGGVVKN<br>　　　T　RT　　TR　T |
| HBsAg1 Th-εK-KKK-α-CGRP 11-25 | 162 | KKKLFLLTKLLTLPQSLD-εK-KKK-RLAGLLSRSGGVVKN<br>RRRIKII RII I L IR<br>　VRVV　　VV V I V<br>　F FF　FF F V F<br>　　　　　F |
| HBsAg2 Th-εK-KKK-α-CGRP 11-25 | 163 | KKKIITITRIITIPQSLD-εK-KKK-RLAGLLSRSGGVVKN<br>　FFLL　　L　ITTI |
| HBsAg3 Th-εK-KKK-α-CGRP 11-25 | 164 | KKKIITITRIITIITTID-εK-KKK-RLAGLLSRSGGVVKN |
| Influenza MP1_1 Th-εK-KKK-α-CGRP 11-25 | 165 | FVFTLTVPSER-εK-KKK-RLAGLLSRSGGVVKN |
| Influenza MP1_2 Th-εK-KKK-α-CGRP 11-25 | 166 | SGPLKAEIAQRLEDV-εK-KKK-RLAGLLSRSGGVVKN |
| Influenza NSP1 Th-εK-KKK-α-CGRP 11-25 | 167 | DRLRRDQKS-εK-KKK-RLAGLLSRSGGVVKN |
| EBV BHRF1 Th-εK-KKK-α-CGRP 11-25 | 168 | AGLTLSLLVICSYLFISRG-εK-KKK-RLAGLLSRSGGVVKNF |
| Clostridium tetani TT1 Th-εK-KKK-α-CGRP 11-25 | 169 | QYIKANSKFIGITEL-εK-KKK-RLAGLLSRSGGVVKN |
| EBV EBNA-1 Th-εK-KKKK-α-CGRP 11-25 | 170 | PGPLRESIVCYFMVFLQTHI-εK-KKK-RLAGLLSRSGGVVKN |
| Clostridium tetani TT2 Th-εK-KKK-α-CGRP 11-25 | 171 | FNNFTVSFWLRVPKVSASHLE-εK-KKK-RLAGLLSRSGGVVKN |
| Clostridium tetani TT3 Th-εK-KKK-α-CGRP 11-25 | 172 | KFIIKRYTPNNEIDSF-εK-KKK-RLAGLLSRSGGVVKN |
| Clostridium tetani TT4 Th-εK-KKK-α-CGRP 11-25 | 173 | VSIDKFRIFCKALNPK-εK-KKK-RLAGLLSRSGGVVKN |
| EBV CP Th-εK-KKK-α-CGRP 11-25 | 174 | VPGLYSPCRAFFNKEELL-εK-KKK-RLAGLLSRSGGVVKN |
| HCMV IE1 Th-εK-KKK-α-CGRP 11-25 | 175 | DKREMWMACIKELH-εK-KKK-RLAGLLSRSGGVVKN |
| EBV GP340 Th-K-KKK-α-CGRP 11-25 | 176 | TGHGARTSTEPTTDY-εK-KKK-RLAGLLSRSGGVVKN |
| EBV BPLF1 Th-εK-KKK-α-CGRP 11-25 | 177 | KELKRQYEKKLRQ-εK-KKK-RLAGLLSRSGGVVKN |
| EBV EBNA-2 Th-εK-KKK-α-CGRP 11-25 | 178 | TVFYNIPPMPL-εK-KKK-RLAGLLSRSGGVVKN |
| HBsAg4 Th-εK-KKK-α-CGRP 11-25 | 179 | FFLLTRILTIPQSLD-εK-KKK-RLAGLLSRSGGVVKN |
| Yersinia Invasin Th-εK-KKK-α-CGRP 11-25 | 180 | TAKSKKFPSYTATYQF-εK-KKK-RLAGLLSRSGGVVKN |

*Peptides are cyclized by cysteine disulfide bonds with the cysteines underlined.

TABLE 4

Immunogenicity Assessment in Guinea Pigs of α-CGRP Peptide Immunogen Constructs

| Grp # | Peptide immunogen description | SEQ ID NO: | Animal No | α-CGRP$_{1-10}$ (SEQ ID NO: 4) ELISA Log$_{10}$ Titer | | | | | | α-CGRP$_{11-37}$ (SEQ ID NO: 9) ELISA Log$_{10}$ Titer | | | | | |
|---|---|---|---|---|---|---|---|---|---|---|---|---|---|---|---|
| | | | | 0 w | 3 w | 6 w | 9 w | 12 w | 15 w | 0 w | 3 w | 6 w | 9 w | 12 w | 15 w |
| 1 | UBITh1-εK-KKK-αCGRP (1-10) | 116 | 6096 | 0.14 | 4.62 | 5.20 | 5.10 | 5.14 | 5.09 | 0.17 | 0.00 | 1.12 | 1.62 | / | 0.00 |
| | | | 6097 | 0.12 | 4.48 | 4.93 | 4.90 | 5.07 | 5.00 | 0.16 | 0.00 | 2.08 | 2.69 | 3.49 | 3.17 |
| | | | 6098 | 0.10 | 4.42 | 5.10 | 5.05 | 5.18 | 5.24 | 0.14 | 0.00 | 0.11 | 0.00 | 2.38 | 2.44 |
| | | | Avg. | 0.12 | 4.51 | 5.08 | 5.02 | 5.13 | 5.11 | 0.16 | 0.00 | 1.10 | 1.44 | 2.93 | 1.87 |
| 2 | αCGRP (1-10)-KKK-εK-UBITh1 | 117 | 6099 | 0.11 | 1.24 | 3.29 | 3.21 | 3.66 | 3.67 | 0.12 | 0.00 | 0.00 | 0.00 | 0.00 | 0.00 |
| | | | 6100 | 0.12 | 2.03 | 3.82 | 4.73 | 4.81 | 5.00 | 0.13 | 0.00 | 0.91 | 0.00 | 1.74 | 3.50 |
| | | | 6101 | 0.10 | 0.00 | 2.95 | 2.93 | 4.33 | 4.58 | 0.14 | 0.00 | 0.00 | 0.00 | 0.57 | 3.41 |
| | | | Avg. | 0.11 | 1.09 | 3.35 | 3.62 | 4.27 | 4.42 | 0.13 | 0.00 | 0.30 | 0.00 | 0.77 | 2.30 |
| 3 | UBITh1-εK-KKK-αCGRP (1-10)-KKK-εK-UBITh1 | 118 | 6102 | 0.11 | 1.61 | 4.26 | 4.62 | 4.85 | 4.73 | 0.14 | 0.00 | 2.40 | 0.00 | 0.74 | 2.03 |
| | | | 6103 | 0.11 | 0.52 | 3.36 | 3.58 | 4.32 | 4.75 | 0.15 | 0.00 | 0.00 | 0.00 | 1.85 | 3.60 |
| | | | 6104 | 0.12 | 2.46 | 3.05 | 3.98 | 4.67 | 4.57 | 0.26 | 0.00 | 0.69 | 0.00 | 1.04 | 2.89 |
| | | | Avg. | 0.11 | 1.53 | 3.56 | 4.06 | 4.61 | 4.68 | 0.18 | 0.00 | 1.03 | 0.00 | 1.21 | 2.84 |
| 4 | UBITh1-εK-KKK-αCGRP (31-37) | 119 | 6105 | 0.11 | 0.00 | 0.00 | 0.00 | 0.00 | 2.08 | 0.16 | 5.71 | 13.93 | 9.39 | 9.70 | 7.72 |
| | | | 6106 | 0.09 | 0.00 | 0.00 | 0.00 | 0.00 | 2.86 | 0.14 | 12.57 | 10.43 | 7.12 | 7.30 | 7.29 |
| | | | 6107 | 0.11 | 0.00 | 0.00 | 0.00 | 0.00 | 2.57 | 0.14 | 7.08 | >10 | >10 | >10 | >10 |
| | | | Avg. | 0.10 | 0.00 | 0.00 | 0.00 | 0.00 | 2.50 | 0.15 | 8.45 | 12.18 | 8.25 | 8.50 | 7.50 |
| 5 | UBITh1-εK-KKK-αCGRP (28-37) | 120 | 6108 | 0.11 | 0.00 | 0.00 | 0.00 | 0.00 | 0.00 | 0.14 | 6.63 | >10 | 7.71 | 8.03 | 7.43 |
| | | | 6109 | 0.08 | 0.00 | 0.00 | 0.00 | 0.00 | 0.00 | 0.15 | 10.08 | 11.22 | 7.95 | 7.37 | 6.90 |
| | | | 6110 | 0.10 | 0.00 | 0.00 | 0.00 | 0.00 | 0.00 | 0.15 | 6.64 | 8.90 | 6.97 | 7.63 | / |
| | | | Avg. | 0.10 | 0.00 | 0.00 | 0.00 | 0.00 | 0.00 | 0.15 | 7.78 | 10.06 | 7.54 | 7.68 | 7.17 |
| 6 | UBITh1-εK-KKK-αCGRP (25-37) | 121 | 6111 | 0.10 | 0.00 | 0.00 | 0.00 | 0.00 | 0.00 | 0.17 | 11.80 | 10.07 | 6.64 | 7.00 | 7.20 |
| | | | 6112 | 0.12 | 0.00 | 0.00 | 0.00 | 0.00 | 0.00 | 0.15 | 9.21 | 8.52 | 6.91 | 6.67 | 10.53 |
| | | | 6113 | 0.09 | 0.00 | 0.00 | 0.00 | 0.00 | 0.00 | 0.13 | 9.49 | 11.26 | 8.01 | 8.58 | 7.30 |
| | | | Avg. | 0.10 | 0.00 | 0.00 | 0.00 | 0.00 | 0.00 | 0.15 | 10.17 | 9.95 | 7.19 | 7.42 | 8.34 |
| 7 | UBITh1-εK-KKK-αCGRP (18-37) | 122 | 6114 | 0.08 | 0.00 | 0.00 | 0.00 | 0.00 | 0.00 | 0.12 | 9.17 | 7.85 | 6.02 | 6.07 | 5.90 |
| | | | 6115 | 0.10 | 0.00 | 0.00 | 0.00 | 0.00 | 0.00 | 0.13 | 10.20 | 8.40 | 5.96 | 6.66 | 7.51 |
| | | | 6116 | 0.12 | 0.00 | 0.00 | 0.00 | 0.00 | 1.19 | 0.14 | 10.79 | 7.43 | 6.32 | 6.69 | 6.07 |
| | | | Avg. | 0.10 | 0.00 | 0.00 | 0.00 | 0.00 | 0.40 | 0.13 | 10.05 | 7.89 | 6.10 | 6.47 | 6.49 |
| 8 | UBITh1-εK-KKK-αCGRP (11-37) | 123 | 6117 | 0.08 | 0.00 | 0.00 | 0.00 | 0.00 | 0.71 | 0.12 | 12.78 | 12.30 | 9.52 | 8.81 | 8.41 |
| | | | 6118 | 0.10 | 0.00 | 0.00 | 0.00 | 0.00 | 1.16 | 0.12 | 10.81 | 13.87 | 9.13 | 7.83 | 6.65 |
| | | | 6119 | 0.11 | 0.00 | 0.00 | 0.00 | 0.00 | 0.00 | 0.15 | 12.14 | 15.51 | 10.15 | 9.56 | 7.12 |
| | | | Avg. | 0.09 | 0.00 | 0.00 | 0.00 | 0.00 | 0.63 | 0.13 | 11.91 | 13.89 | 9.60 | 8.73 | 7.39 |

35

TABLE 5

Immunogenicity Assessment in Guinea Pigs of α-CGRP Peptide Immunogen Constructs

| Group # | Peptide immunogen description | SEQ ID NO: | Animal No | α-CGRP$_{11-37}$ (SEQ ID NO: 9) ELISA Log$_{10}$ Titer | | | | | α-CGRP$_{1-25}$ (SEQ ID NO: 13) ELISA Log$_{10}$ Titer | | | | | α-CGRP$_{8-18}$ (SEQ ID NO: 14) ELISA Log$_{10}$ Titer | | | | |
|---|---|---|---|---|---|---|---|---|---|---|---|---|---|---|---|---|---|---|
| | | | | 0 w | 3 w | 6 w | 9 w | 12 w | 0 w | 3 w | 6 w | 9 w | 12 w | 0 w | 3 w | 6 w | 9 w | 12 w |
| 1 | αCGRP (1-15)-KKK-εK-UBITh1 | 124 | 6721 | 0.127 | 3.109 | 3.854 | 3.140 | 3.122 | 0.095 | 3.399 | 5.164 | 5.054 | 5.051 | 0.089 | 0.000 | 0.000 | 0.000 | 1.362 |
| | | | 6722 | 0.234 | 0.000 | 1.963 | 0.000 | 2.252 | 0.079 | 3.540 | 5.384 | 5.142 | 5.099 | 0.075 | 0.000 | 1.170 | 0.000 | 0.000 |
| | | | 6723 | 0.118 | 2.963 | 4.086 | 3.158 | 2.968 | 0.073 | 3.135 | 5.336 | 5.163 | 5.109 | 0.078 | 0.000 | 1.016 | 0.000 | 0.000 |
| 2 | αCGRP (1-18)-KKK-εK-UBITh1 | 125 | 6724 | 0.129 | 3.462 | 4.977 | 4.695 | 3.696 | 0.076 | 4.012 | 5.165 | 5.103 | 5.019 | 0.073 | 0.000 | 2.465 | 0.000 | 0.780 |
| | | | 6725 | 6.691 | 2.938 | 5.524 | 5.178 | 5.300 | 0.085 | 3.015 | 5.077 | 4.997 | 4.961 | 0.082 | 0.000 | 3.292 | 3.150 | 3.176 |
| | | | 6726 | 0.079 | 2.297 | 5.023 | 4.757 | 4.913 | 0.085 | 3.226 | 5.347 | 5.078 | 5.079 | 0.075 | 0.000 | 2.858 | 2.575 | 2.992 |
| 3 | αCGRP (1-20)-KKK-εK-UBITh1 | 126 | 6727 | 0.075 | 2.957 | 5.098 | 4.921 | 5.000 | 0.080 | 3.255 | 5.335 | 5.111 | 5.118 | 0.077 | 0.000 | 2.957 | 2.429 | 3.065 |
| | | | 6728 | 0.077 | 3.441 | 5.284 | 5.043 | 4.937 | 0.082 | 3.825 | 5.587 | 5.397 | 5.528 | 0.076 | 0.000 | 2.957 | 2.273 | 2.602 |
| | | | 6729 | 0.094 | 2.833 | 5.021 | 4.732 | 4.602 | 0.093 | 2.978 | 5.094 | 4.926 | 4.774 | 0.077 | 0.000 | 2.227 | 1.345 | 0.000 |
| 4 | αCGRP (1-25)-KKK-εK-UBITh1 | 127 | 6730 | 0.072 | 4.959 | 5.922 | 5.157 | 5.034 | 0.069 | 4.190 | 5.630 | 5.151 | 5.040 | 0.067 | 0.000 | 0.771 | 0.000 | 0.000 |
| | | | 6731 | 0.104 | 4.752 | 6.413 | 5.235 | 5.096 | 0.075 | 4.560 | 6.348 | 5.446 | 5.159 | 0.077 | 0.000 | 3.026 | 3.798 | 2.326 |
| | | | 6732 | 0.111 | 4.605 | 5.873 | 5.134 | 5.071 | 0.081 | 3.900 | 5.752 | 5.278 | 5.173 | 0.078 | 0.000 | 2.473 | 1.667 | 0.672 |
| 5 | αCGRP (8-18)-KKK-εK-UBITh1 | 128 | 6733 | 0.100 | 3.194 | 4.766 | 4.628 | 4.732 | 0.080 | 3.282 | 4.932 | 4.745 | 4.789 | 0.080 | 0.000 | 2.495 | 2.678 | 3.148 |
| | | | 6734 | 0.082 | 2.161 | 4.211 | 4.298 | 4.769 | 0.079 | 2.902 | 4.568 | 4.537 | 4.687 | 0.075 | 0.000 | 0.265 | 2.589 | 3.118 |
| | | | 6735 | 0.071 | 3.154 | 4.695 | 4.678 | 4.663 | 0.076 | 3.940 | 4.862 | 4.745 | 4.668 | 0.078 | 0.000 | 2.978 | 3.079 | 3.094 |
| 6 | UBITh1-εK-KKK-αCGRP (8-18) | 129 | 6736 | 0.126 | 4.674 | 5.250 | 5.012 | 4.940 | 0.086 | 4.682 | 5.324 | 5.095 | 4.934 | 0.080 | 2.269 | 4.540 | 4.462 | 4.348 |
| | | | 6737 | 0.079 | 4.623 | 5.149 | 4.755 | 4.593 | 0.095 | 4.492 | 5.164 | 4.815 | 4.597 | 0.068 | 3.558 | 5.178 | 4.927 | 4.820 |
| | | | 6738 | 0.106 | 4.574 | 5.552 | 5.181 | 5.040 | 0.084 | 4.847 | 6.082 | 5.531 | 5.220 | 0.062 | 1.824 | 4.486 | 4.552 | 4.549 |
| 7 | UBITh1- | 130 | 6739 | 0.117 | 10.681 | >10 | 8.478 | 7.453 | 0.087 | 0.000 | 1.433 | 2.655 | 3.040 | 0.070 | 0.000 | 0.000 | 0.000 | 0.000 |

TABLE 5-continued

Immunogenicity Assessment in Guinea Pigs of α-CGRP Peptide Immunogen Constructs

| Group # | Peptide immu- nogen descrip- tion | SEQ ID NO: | Ani- mal No | α-CGRP$_{11\text{-}37}$ (SEQ ID NO: 9) ELISA Log$_{10}$ Titer | | | | | α-CGRP$_{1\text{-}25}$ (SEQ ID NO: 13) ELISA Log$_{10}$ Titer | | | | | α-CGRP$_{8\text{-}18}$ (SEQ ID NO: 14) ELISA Log$_{10}$ Titer | | | | |
|---|---|---|---|---|---|---|---|---|---|---|---|---|---|---|---|---|---|---|
| | | | | 0 w | 3 w | 6 w | 9 w | 12 w | 0 w | 3 w | 6 w | 9 w | 12 w | 0 w | 3 w | 6 w | 9 w | 12 w |
| | εK- αCGRP (11-37) | | 6740 | 0.124 | >10 | >10 | >10 | >10 | 0.089 | 2.891 | 4.645 | 4.659 | 4.622 | 0.077 | 0.000 | 0.000 | 0.000 | 0.000 |
| | | | 6741 | 0.095 | >10 | >10 | >10 | >10 | 0.103 | 2.931 | 4.808 | 4.672 | 4.788 | 0.083 | 0.000 | 0.000 | 0.000 | 0.000 |

TABLE 6

Immunogenicity Assessment in Guinea Pigs of α-CGRP Peptide Immunogen Constructs

| Group # | Peptide immunogen description | SEQ ID NO: | Animal No | α-CGRP$_{11\text{-}35}$ (SEQ ID NO: 18) ELISA Log$_{10}$ Titer | | | | | α-CGRP$_{15\text{-}37}$ (SEQ ID NO: 19) ELISA Log$_{10}$ Titer | | | | |
|---|---|---|---|---|---|---|---|---|---|---|---|---|---|
| | | | | 0 w | 3 w | 6 w | 9 w | 12 w | 0 w | 3 w | 6 w | 9 w | 12 w |
| 1 | UBITh1-εK-KKK- αCGRP (11-25) | 131 | 6823 | 0.089 | 5.136 | >10 | 5.271 | 5.020 | 0.079 | 4.948 | >10 | 5.826 | 5.122 |
| | | | 6824 | 0.094 | 6.042 | >10 | 5.395 | 5.056 | 0.083 | 5.341 | >10 | 7.013 | 5.191 |
| | | | 6825 | 0.086 | 5.942 | 7.707 | 5.255 | 4.994 | 0.076 | 5.029 | 6.660 | 5.262 | 4.949 |
| 2 | UBITh1-εK-KKK- αCGRP (11-30) | 133 | 6826 | 0.088 | 5.397 | 5.668 | 5.051 | 4.879 | 0.095 | 5.169 | 5.634 | 5.231 | 5.025 |
| | | | 6827 | 0.074 | 5.202 | 5.633 | 5.057 | 4.893 | 0.108 | 4.907 | 5.409 | 5.150 | 5.106 |
| | | | 6828 | 0.073 | 5.425 | 5.729 | 5.091 | 4.917 | 0.079 | 5.194 | 5.405 | 5.267 | 5.106 |
| 3 | UBITh1-εK-KKK- αCGRP (11-33) | 135 | 6829 | 0.093 | 5.599 | 5.366 | 5.112 | 5.096 | 0.075 | 5.277 | 5.298 | 5.162 | 5.087 |
| | | | 6830 | 0.082 | 6.234 | >10 | 5.577 | 5.222 | 0.072 | 5.730 | 7.937 | 7.026 | 5.487 |
| | | | 6831 | 0.075 | 5.458 | 5.963 | 5.172 | 5.051 | 0.061 | 5.225 | 5.453 | 5.380 | 5.180 |
| 4 | UBITh1-εK-KKK- αCGRP (11-35) | 137 | 6832 | 0.08 | 10.05 | 8.83 | 7.364 | 5.819 | 0.082 | 8.101 | 6.224 | 5.453 | 5.036 |
| | | | 6833 | 0.075 | 10.06 | >10 | 7.443 | 6.106 | 0.067 | 7.523 | 7.232 | 5.896 | 5.313 |
| | | | 6834 | 0.08 | 7.833 | >10 | 8.988 | 5.759 | 0.086 | 5.424 | 5.567 | 5.780 | 5.221 |
| 5 | UBITh1-εK-kkk- αCGRP (15-37) | 139 | 6835 | 0.112 | 5.075 | 4.914 | 4.859 | 4.727 | 0.096 | >10 | 10.351 | >10 | 6.721 |
| | | | 6836 | 0.073 | 4.943 | 4.983 | 5.290 | 5.022 | 0.099 | 5.428 | 6.345 | 10.811 | 5.828 |
| | | | 6837 | 0.093 | 5.041 | 4.832 | 4.903 | 4.878 | 0.073 | >10 | 9.509 | 6.990 | 5.625 |

TABLE 7

Cross-Reactivities of Immune Sera with Full-Length CGRP

| CGRP peptide immunogen | SEQ ID NO: | Animal ID | α-CGRP$_{1\text{-}37}$ (SEQ ID NO: 1) ELISA Log$_{10}$ Titer | | |
|---|---|---|---|---|---|
| | | | 6 wpi | 9 wpi | 12 wpi |
| UBITh1-εK-KKK- αCGRP (1-10) | 116 | 6096 | 5.41 | 5.16 | 5.02 |
| | | 6097 | 5.29 | 5.40 | 5.65 |
| | | 6098 | 5.47 | 5.67 | 5.63 |
| αCGRP (1-10)- KKK-εK-UBITh1 | 117 | 6099 | 5.39 | 5.39 | 5.61 |
| | | 6100 | 5.61 | 7.11 | 7.43 |
| | | 6101 | 5.41 | 5.33 | 5.66 |
| UBITh1-εk-KKK- αCGRP (1-10)- KKK-εK-UBITh1 | 118 | 6102 | 8.21 | >10 | >10 |
| | | 6103 | 5.44 | 5.71 | 7.25 |
| | | 6104 | 5.71 | 6.34 | 7.92 |
| UBITh1-εK-KKK- αCGRP (31-37) | 119 | 6105 | >10 | >10 | >10 |
| | | 6106 | >10 | >10 | 10.50 |
| | | 6107 | >10 | >10 | >10 |
| UBITh1-εK-KKK- αCGRP (28-37) | 120 | 6108 | >10 | >10 | >10 |
| | | 6109 | >10 | >10 | >10 |
| | | 6110 | >10 | 10.84 | 11.63 |
| UBITh1-εK-KKK- αCGRP (25-37) | 121 | 6111 | >10 | 11.89 | 11.48 |
| | | 6112 | >10 | 8.97 | 7.12 |
| | | 6113 | >10 | >10 | >10 |
| UBITh1-εK-KKK- αCGRP (18-37) | 122 | 6114 | >10 | 9.88 | >10 |
| | | 6115 | >10 | 9.67 | >10 |
| | | 6116 | >10 | 11.23 | 10.42 |
| UBITh1-εK-KKK- αCGRP (11-37) | 123 | 6117 | >10 | >10 | 10.97 |
| | | 6118 | >10 | 9.48 | 7.09 |
| | | 6119 | >10 | >10 | >10 |

TABLE 7-continued

| | | | α-CGRP$_{1-37}$ (SEQ ID NO: 1) ELISA Log$_{10}$ Titer | | |
|---|---|---|---|---|---|
| CGRP peptide immunogen | SEQ ID NO: | Animal ID | 6 wpi | 9 wpi | 12 wpi |
| αCGRP (1-15)-KKK-εK-UBITh1 | 124 | 6721 | 5.39 | 5.39 | 5.61 |
| | | 6722 | 5.61 | 7.11 | 7.43 |
| | | 6723 | 5.41 | 5.33 | 5.66 |
| αCGRP (1-18)-KKK-εK-UBITh1 | 125 | 6724 | 8.21 | >10 | >10 |
| | | 6725 | 5.44 | 5.71 | 7.25 |
| | | 6726 | 5.71 | 6.34 | 7.92 |
| αCGRP (1-20)-KKK-εK-UBITh1 | 126 | 6727 | >10 | >10 | >10 |
| | | 6728 | >10 | >10 | 10.50 |
| | | 6729 | >10 | >10 | >10 |
| αCGRP (1-25)-KKK-εK-UBITh1 | 127 | 6730 | >10 | >10 | >10 |
| | | 6731 | >10 | >10 | >10 |
| | | 6732 | >10 | 10.84 | 11.63 |
| αCGRP (8-18)-KKK-εK-UBITh1 | 128 | 6733 | >10 | 11.89 | 11.48 |
| | | 6734 | >10 | 8.97 | 7.12 |
| | | 6735 | >10 | >10 | >10 |
| UBITh1-εK-KKK-αCGRP (8-18) | 129 | 6736 | >10 | 9.88 | >10 |
| | | 6737 | >10 | 9.67 | >10 |
| | | 6738 | >10 | 11.23 | 10.42 |
| UBITh1-εK-KKK- αCGRP (11-25) | 131 | 6823 | 6.400 | 5.414 | 5.239 |
| | | 6824 | 6.648 | 5.507 | 5.241 |
| | | 6825 | 6.305 | 5.116 | 5.038 |
| UBITh1-εK-KKK-αCGRP (11-30) | 133 | 6826 | 5.411 | 5.138 | 5.056 |
| | | 6827 | 5.357 | 5.078 | 4.994 |
| | | 6828 | 5.679 | 5.149 | 5.165 |
| UBITh1-εK-KKK-αCGRP (11-33) | 135 | 6829 | 5.153 | 5.147 | 5.348 |
| | | 6830 | 8.112 | 5.540 | 6.021 |
| | | 6831 | 5.487 | 5.301 | 5.673 |
| UBITh1-εK-KKK-αCGRP (11-35) | 137 | 6832 | 6.008 | 5.347 | 5.386 |
| | | 6833 | 8.078 | 5.649 | 5.482 |
| | | 6834 | 5.603 | 5.582 | 6.109 |
| UBITh1-εK-KKK-αCGRP (15-37) | 139 | 6835 | >10 | >10 | >10 |
| | | 6836 | 7.322 | 7.323 | 5.937 |
| | | 6837 | >10 | 8.384 | 9.439 |

TABLE 8

Lack of Endogenous Th Epitopes within the Selected CGRP B Epitope Sequences

| | | | α-CGRP$_{1-25}$ (SEQ ID NO: 13) ELISA Log$_{10}$ Titer | | | α-CGRP$_{11-37}$ (SEQ ID NO: 9) ELISA Log$_{10}$ Titer | | |
|---|---|---|---|---|---|---|---|---|
| Peptide description | SEQ ID NO: | Animal ID | 0 w | 3 w | 6 w | 0 w | 3 w | 6 w |
| α-CGRP (31-37) | 5 | 7174 | 0.073 | 0.000 | 0.000 | 0.067 | 0.000 | 0.000 |
| | | 7175 | 0.073 | 0.000 | 0.000 | 0.066 | 0.000 | 0.000 |
| | | 7176 | 0.079 | 0.000 | 0.000 | 0.064 | 0.000 | 0.000 |
| α-CGRP (28-37) | 6 | 7177 | 0.075 | 0.000 | 0.000 | 0.059 | 0.000 | 0.349 |
| | | 7178 | 0.075 | 0.000 | 0.000 | 0.079 | 0.000 | 0.000 |
| | | 7179 | 0.070 | 0.000 | 0.000 | 0.067 | 0.000 | 0.000 |
| α-CGRP (11-25) | 15 | 7195 | 0.067 | 0.000 | 0.000 | 0.054 | 0.000 | 0.000 |
| | | 7196 | 0.087 | 0.000 | 0.000 | 0.061 | 0.000 | 0.000 |
| | | 7197 | 0.096 | 0.000 | 0.000 | 0.085 | 0.000 | 0.000 |

TABLE 9

Immunogenicity Assessment in Guinea Pigs against the Th Epitope Portion of the selected CGRP Peptide Immunogen Constructs

| | | | α-CGRP$_{20-37}$ (SEQ ID NO: 20) ELISA Log$_{10}$ Titer | | | UBITh1 (SEQ ID NO: 98) ELISA Log$_{10}$ titer | | |
|---|---|---|---|---|---|---|---|---|
| Peptide immunogen description | SEQ ID NO: | Animal ID | 0 wpi | 3 wpi | 6 wpi | 0 wpi | 3 wpi | 6 wpi |
| UBITh1-εK-KKK-αCGRP (20-37) | 142 | 7282 | 0.092 | 5.511 | 5.323 | 0.127 | 0.000 | 0.000 |
| | | 7283 | 0.092 | 5.405 | 5.085 | 0.106 | 0.000 | 0.000 |
| | | 728 | 0.090 | 5.991 | 5.058 | 0.111 | 0.000 | 0.000 |
| UBITh1-εK-KKK-αCGRP (22-37) | 143 | 7285 | 0.104 | 5.823 | 5.811 | 0.114 | 0.000 | 0.000 |
| | | 7286 | 0.090 | 5.766 | 5.686 | 0.121 | 0.000 | 0.000 |
| | | 7287 | 0.095 | 6.087 | 5.151 | 0.107 | 0.000 | 0.000 |

TABLE 10

Mapping of α-CGRP Binding B epitopes with Immune Sera from α-CGRP Peptide Immunogen Constructs

| 10 mer peptide design for epitope mapping from 9 to 46 of α CGRP GSRIIAQKRACDTATCVTHRLAGLLSRSGGVVEKNNFVPTNVG-SKAFGRRRRDLQA | SEQ ID NO | | Seq-uence | A450nm ELISA of Immune Sera from α CGRP Peptide Immunogen Constructs SEQ ID NO | | | | | | | |
|---|---|---|---|---|---|---|---|---|---|---|---|
| | | | | 123 CGRP 11-37 | 122 CGRP 18-37 | 127 CGRP 1-25 | 129 CGRP 8-18 | 130 CGRP 11-37 | 132 CGRP 11-25 | 137 CGRP 11-35 | 139 CGRP 15-37 |
| | 181 | | | | | | | | | | |
| GSRIIAQKRA | 26 | 9 | 1 | 0.575 | 0.245 | 0.190 | 0.099 | 0.153 | 0.116 | 0.109 | 0.126 |
| SRIIAQKRAC | 27 | 8 | 2 | 0.564 | 0.203 | 0.140 | 0.102 | 0.141 | 0.118 | 0.110 | 0.124 |
| RIIAQKRACD | 28 | 7 | 3 | 0.476 | 0.191 | 0.136 | 0.102 | 0.147 | 0.110 | 0.101 | 0.134 |
| IIAQKRACDT | 29 | 6 | 4 | 0.489 | 0.203 | 0.129 | 0.091 | 0.136 | 0.113 | 0.094 | 0.103 |
| IAQKRACDTA | 30 | 5 | 5 | 0.472 | 0.186 | 0.142 | 0.097 | 0.120 | 0.103 | 0.099 | 0.125 |
| AQKRACDTAT | 31 | 4 | 6 | 0.448 | 0.249 | 0.112 | 0.086 | 0.108 | 0.093 | 0.087 | 0.099 |
| QKRACDTATC | 32 | 3 | 7 | 0.691 | 1.372 | 0.258 | 0.094 | 0.141 | 0.098 | 0.094 | 0.148 |
| KRACDTATCV | 33 | 2 | 8 | 0.660 | 1.071 | 2.378 | 0.180 | 0.129 | 0.102 | 0.094 | 0.116 |
| RACDTATCVT | 34 | 1 | 9 | 0.436 | 0.265 | 2.286 | 0.263 | 0.169 | 0.123 | 0.118 | 0.139 |
| ACDTATCVTH | 35 | 1 | 10 | 0.493 | 0.194 | 3.076 | 0.340 | 0.126 | 0.104 | 0.098 | 0.110 |
| CDTATCVTHR | 36 | 2 | 11 | 0.472 | 0.183 | 3.965 | 1.117 | 0.126 | 0.105 | 0.098 | 0.121 |
| DTATCVTHRL | 37 | 3 | 12 | 0.494 | 0.189 | 3.875 | 0.105 | 0.131 | 0.104 | 0.097 | 0.116 |
| TATCVTHRLA | 38 | 4 | 13 | 0.515 | 0.194 | 3.723 | 0.111 | 0.138 | 0.108 | 0.101 | 0.114 |
| ATCVTHRLAG | 39 | 5 | 14 | 0.514 | 0.199 | 0.636 | 0.109 | 0.136 | 0.113 | 0.108 | 0.107 |
| TCVTHRLAGL | 40 | 6 | 15 | 0.884 | 0.324 | 0.522 | 0.214 | 0.235 | 0.836 | 0.322 | 0.471 |
| CVTHRLAGLL | 41 | 7 | 16 | 0.950 | 0.524 | 0.708 | 0.733 | 0.489 | 0.479 | 0.477 | 0.426 |
| VTHRLAGLLS | 42 | 8 | 17 | 0.502 | 0.185 | 0.228 | 1.076 | 0.149 | 0.108 | 0.099 | 0.104 |
| THRLAGLLSR | 43 | 9 | 18 | 0.588 | 0.209 | 0.300 | 0.249 | 0.166 | 0.166 | 0.161 | 0.117 |
| HRLAGLLSRS | 44 | 10 | 19 | 0.552 | 0.203 | 0.297 | 0.171 | 0.137 | 0.134 | 0.130 | 0.101 |
| RLAGLLSRSG | 45 | 11 | 20 | 0.473 | 0.196 | 0.213 | 0.119 | 0.127 | 0.114 | 0.110 | 0.104 |
| LAGLLSRSGG | 46 | 12 | 21 | 0.462 | 0.210 | 0.228 | 0.109 | 0.122 | 0.100 | 0.089 | 0.108 |
| AGLLSRSGGV | 47 | 13 | 22 | 0.423 | 0.175 | 0.218 | 0.094 | 0.159 | 0.103 | 0.089 | 0.096 |
| GLLSRSGGVV | 48 | 14 | 23 | 0.399 | 0.179 | 0.928 | 0.115 | 0.565 | 0.266 | 0.108 | 0.100 |
| LLSRSGGVVK | 49 | 15 | 24 | 0.566 | 0.301 | 3.642 | 0.109 | 1.336 | 3.120 | 0.510 | 0.102 |
| LSRSGGVVEKN | 50 | 16 | 25 | 0.425 | 0.584 | 3.850 | 0.185 | 0.734 | 4.000 | 0.268 | 0.851 |
| SRSGGVVEKNN | 51 | 17 | 26 | 0.426 | 0.848 | 3.797 | 0.145 | 0.112 | 3.282 | 0.310 | 2.235 |
| RSGGVVKNNF | 52 | 18 | 27 | 0.584 | 0.537 | 1.972 | 0.130 | 0.203 | 0.295 | 0.176 | 0.661 |
| SGGVVEKNNFV | 53 | 19 | 28 | 0.423 | 0.281 | 0.192 | 0.101 | 0.158 | 0.100 | 0.100 | 0.178 |
| GGVVKNNFVP | 54 | 20 | 29 | 0.708 | 0.572 | 0.201 | 0.092 | 1.249 | 0.090 | 0.252 | 2.268 |
| GVVEKNNFVPT | 55 | 21 | 30 | 0.863 | 0.491 | 0.205 | 0.123 | 1.050 | 1.080 | 0.283 | 1.697 |
| VVEKNNFVPTN | 56 | 22 | 31 | 0.719 | 0.418 | 0.201 | 0.105 | 0.321 | 0.259 | 1.274 | 0.437 |
| VEKNNFVPTNV | 57 | 23 | 32 | 1.768 | 2.259 | 0.207 | 0.118 | 1.031 | 0.111 | 4.000 | 0.325 |
| KNNFVPTNVG | 58 | 24 | 33 | 1.285 | 3.381 | 0.210 | 0.102 | 0.878 | 0.103 | 4.000 | 0.777 |
| NNFVPTNVGS | 59 | 25 | 34 | 0.425 | 0.194 | 0.208 | 0.104 | 0.141 | 0.106 | 0.271 | 0.124 |
| NFVPTNVGSK | 60 | 26 | 35 | 0.705 | 0.542 | 0.205 | 0.106 | 1.697 | 0.106 | 4.000 | 0.248 |

TABLE 10-continued

Mapping of α-CGRP Binding B epitopes with Immune Sera from α-CGRP Peptide Immunogen Constructs

| 10 mer peptide design for epitope mapping from 9 to 46 of α CGRP | SEQ ID NO | Seq-uence | | A450nm ELISA of Immune Sera from α CGRP Peptide Immunogen Constructs SEQ ID NO | | | | | | | |
|---|---|---|---|---|---|---|---|---|---|---|---|
| | | start | end | 123 CGRP 11-37 | 122 CGRP 18-37 | 127 CGRP 1-25 | 129 CGRP 8-18 | 130 CGRP 11-37 | 132 CGRP 11-25 | 137 CGRP 11-35 | 139 CGRP 15-37 |
| GSRIIAQKRACDTATCVTHRLAGLLSRSGGVVEKNNFVPTNVG-SKAFGRRRRDLQA | 181 | | | | | | | | | | |
| FVPTNVGSKA | 61 | 27 | 36 | 0.535 | 0.407 | 0.232 | 0.115 | 1.255 | 0.120 | 3.238 | 0.189 |
| VPTNVGSKAF | 62 | 28 | 37 | 3.730 | 3.796 | 0.222 | 0.103 | 4.000 | 0.106 | 0.964 | 4.000 |
| PTNVGSKAFG | 63 | 29 | 38 | 3.537 | 2.160 | 0.132 | 0.090 | 2.709 | 0.095 | 0.478 | 1.299 |
| TNVGSKAFGR | 64 | 30 | 39 | 0.921 | 0.344 | 0.138 | 0.091 | 0.367 | 0.098 | 0.096 | 0.263 |
| NVGSKAFGRR | 65 | 31 | 40 | 0.660 | 0.223 | 0.142 | 0.096 | 0.155 | 0.097 | 0.083 | 0.125 |
| VGSKAFGRRR | 66 | 32 | 41 | 0.697 | 0.243 | 0.173 | 0.106 | 0.149 | 0.114 | 0.091 | 0.119 |
| GSKAFGRRRR | 67 | 33 | 42 | 0.570 | 0.229 | 0.164 | 0.105 | 0.134 | 0.120 | 0.096 | 0.114 |
| SKAFGRRRRD | 68 | 34 | 43 | 0.618 | 0.237 | 0.152 | 0.100 | 0.158 | 0.135 | 0.099 | 0.126 |
| KAFGRRRRDL | 69 | 35 | 44 | 0.699 | 0.252 | 0.176 | 0.113 | 0.210 | 0.121 | 0.121 | 0.134 |
| AFGRRRRDLQ | 70 | 36 | 45 | 0.606 | 0.233 | 0.177 | 0.128 | 0.163 | 0.139 | 0.120 | 0.137 |
| RLAGLLSRSGGVVKNNFVPTNVGSKAF | 8 | 11 | 37 | 3.759 | 3.814 | 2.080 | 0.348 | 3.708 | 1.693 | 2.274 | 3.788 |
| ACDTATCVTHRLAGLLSRSGGVVKN | 12 | 1 | 25 | 0.564 | 0.150 | 3.061 | 0.445 | 0.279 | 4.000 | 0.582 | 0.149 |
| ACDTATCVTHRLAGLLSRSGGVVKNNFVPTNVGSKAF | 1 | 1 | 37 | 3.774 | 3.862 | 3.441 | 0.495 | 3.885 | 1.914 | 2.944 | 3.813 |

---

The invention claimed is:

1. A calcitonin gene-related peptide (CGRP) peptide immunogen construct comprising the amino acid sequence of SEQ ID NO: 120.

2. A pharmaceutical composition comprising:

a. the CGRP peptide immunogen construct according to claim 1, wherein the CGRP peptide immunogen construct is mixed with an CpG oligodeoxynucleotide (ODN) to form a stabilized immunostimulatory complex; and b. a pharmaceutically acceptable delivery vehicle and/or adjuvant.

3. A pharmaceutical composition comprising: a CGRP peptide immunogen construct comprising the amino acid sequence of SEQ ID NO: 120, wherein the CGRP peptide immunogen construct is mixed with an CpG oligodeoxynucleotide (ODN) to form a stabilized immunostimulatory complex.

4. A method of generating antibodies against CGRP in a subject comprising administering the pharmaceutical composition according to claim 2 to the subject.

5. A method of preventing or treating migraine in a subject comprising administering the pharmaceutical composition of claim 2 to the subject.

6. The method of claim 5, which is a method of treating migraine.

7. The method of claim 5, which is a method of preventing migraine.

\*   \*   \*   \*   \*